US009469864B2

(12) United States Patent
Thorson et al.

(10) Patent No.: US 9,469,864 B2
(45) Date of Patent: Oct. 18, 2016

(54) REVERSIBLE NATURAL PRODUCT GLYCOSYLTRANSFERASE-CATALYZED REACTIONS, COMPOUNDS AND RELATED METHODS

(71) Applicant: Wisconsin Alumni Research Foundation, Madison, WI (US)

(72) Inventors: Jon S. Thorson, Middleton, WI (US); Changsheng Zhang, Madison, WI (US); Byron R. Griffith, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/335,067

(22) Filed: Jul. 18, 2014

(65) Prior Publication Data

US 2015/0141294 A1    May 21, 2015

Related U.S. Application Data

(62) Division of application No. 11/847,731, filed on Aug. 30, 2007, now Pat. No. 8,841,092.

(60) Provisional application No. 60/824,018, filed on Aug. 30, 2006.

(51) Int. Cl.

| C12P 19/62 | (2006.01) |
|---|---|
| C12P 19/00 | (2006.01) |
| C12P 19/18 | (2006.01) |
| C12P 19/38 | (2006.01) |
| C12P 19/60 | (2006.01) |
| C07H 15/203 | (2006.01) |
| C07H 17/08 | (2006.01) |
| C07H 19/01 | (2006.01) |
| C07K 9/00 | (2006.01) |
| C12P 19/44 | (2006.01) |

(52) U.S. Cl.
CPC .......... *C12P 19/623* (2013.01); *C07H 15/203* (2013.01); *C07H 17/08* (2013.01); *C07H 19/01* (2013.01); *C07K 9/008* (2013.01); *C12P 19/18* (2013.01); *C12P 19/44* (2013.01); *C12P 19/62* (2013.01)

(58) Field of Classification Search
CPC ......... C12P 19/62; C12P 19/18; C12P 19/44; C12N 15/52; C12N 15/1131; C07H 15/203
USPC ...................................... 506/26; 435/74, 76
See application file for complete search history.

(56) References Cited

U.S. PATENT DOCUMENTS 4,970,198 A    11/1990 Lee et al.

OTHER PUBLICATIONS

Zhang et al., "Expoliting the Reversibility of Natural Product Glycosyltransferase-Catalyzed Reactions", Science 20060901 US; vol. 313, No. 5719, Sep. 1, 2006; pp. 1291-1294.
PCT/US2007/077258 International Search Report, 2007.
Amann et al., Carbohydr. Res., 2001, 335, 23-32.
Ahlert et al., Science 2002, 297, 1173.
Blanchard et al., Curr. Opin. Chem. Biol., 2006, 10, 263.
Breton et al., Glycobiology, 2006, 16, 29R.
Bililign et al., ChemBioChem., 2002, 3, 1143.
Bradford, Anal. Biochem., 1976, 72, 248.
Barton et al., Proc. Natl. Acad. Sci. U.S.A., 2002, 99, 13397.
Cardini et al., J. Biol. Chem., 1955, 214, 149.
Devos et al., Proteins: Structure, Function and Genetics, 2000, vol. 41:98-107.
Doumith et al., Mol. Gen. Genet., 2000, 264, 477-485.
Dourmishev et al., Int. J. Dermatol., 2005, 44, 981-988.
Deangelis et al., J. Biol. Chem., 2003, 278, 35199.
Fu et al., Nat. Biotechnol., 2003, 21, 1467.
Griffith et al., Curr. Opin. Biotechnol., 2005, 16, 622.
Glaser et al., J. Biol. Chem., 1957, 228, 729.
Geary, Trends Parasitol, 2005, 21, 530-532.
Hitchcock et al., J. Am. Chem. Soc., 1995, 117, 5750.
Ikeda et al., Proc. Natl. Acad. Sci. U.S.A., 1999, 96, 9509-9514.
Ikeda et al., Chem. Rev., 1997, 97, 2591-2610.
Jiang et al., J. Am. Chem. Soc., 2000, 122, 6803.
Jiang et al., Angew. Chem. Int. Ed. Engl., 2001, 40, 1502.
Kim et al., J. Am. Chem. Soc., 1994, 116, 1766.
Koeller et al., Chem. Rev., 2000, 100, 4465.
Kieser et al., 2000, Practical Streptomyces Genetics, Norwich, England.
Kisselev L., Structure, 2002, vol. 10:8-9.
Losey et al., Biochemistry, 2001, 40, 4745.
Losey et al., Chem. Biol., 2002, 9, 1305.
Luzhetskyy et al., Chem. Biol., 2005, 12, 725-729.
Marumo et al., Eur. J. Biochem., 1992, 204, 539.
Minami et al., Tetrahedron Lett., 2005, 46, 6187.

(Continued)

*Primary Examiner* — Robert Mondesi
*Assistant Examiner* — Younus Meah
(74) *Attorney, Agent, or Firm* — Boyle Fredrickson, S.C.

(57) ABSTRACT

The present invention relates to methods of use of glycosyltransferases and related novel compounds. The invention exploits the reversibility of glycosyltransferases to generate new sugars, unnatural biomolecules and numerous one-pot reactions for generation of new biomolecules having varied backbones such as enediynes, vancomycins, bleomycins, anthracyclines, macrolides, pluramycins, aureolic acids, indolocarbazoles, aminglycosides, glycopeptides, polyenes, coumarins, benzoisochromanequinones, calicheamicins, erythromycin, avermectins, ivermectins, angucyclines, cardiac glycosides, steroids or flavinoids. In preferred embodiments, the invention specifically relates to biosynthesis of anticancer (the enediyne calicheamicin, CLM), anthelmintic agents (the macrolides avermectin, ivermectin and erythromycin) and antibiotic (the glycopeptide vancomycin, VCM) natural product-based drugs developed by reversible, bidirectional glycosyltransferase-catalyzed reactions.

9 Claims, 38 Drawing Sheets

(56) References Cited

OTHER PUBLICATIONS

Nagarajan et al., J. Chem. Soc., Chem. Comm., 1988, 1306.
Nicolaou et al., J. Am. Chem. Soc., 1993, 115, 7625.
Neufeld et al., Adv. Carb. Chem., 1963, 18, 309.
Omura et al., Nat. Rev. Microbiol., 2004, 2, 984-989.
Oberthur et al., Org. Lett., 2004, 6, 2873.
Pattathil et al., Planta, 2005, 221, 538.
Quiros et al., J. Biol. Chem., 2000, 275, 11713.
Rupprath et al., Curr. Med. Chem., 2005, 12, 1637.
Sousa et al. Microbiology, 2002, 148(Pt 5): 1291-1303.
Schulman et al., J. Biol. Chem., 1990, 265, 16965-16970.
Sears et al., Science, 2001, 291, 2344.
Wacker et al., Science, 2002, 298, 1790.
Walker et al., Proc. Natl. Acad. Sci. U.S.A., 1992, 89,4608.
Walsh et al., Biochem. Soc. Trans., 2003, 31, 487.
Whisstock et al., Quarterly Reviews of Biophysics 2003, vol. 36 (3): 307-340.
Witkowski et al., Biochemistry 38:11643-11650, 1999.
Wohlert et al., Chem. Biol., 2001, 8, 681-700.
Wei et al., Tetrahedron. Lett., 2004, 45, 6895-6898.
Yoon et al., Appl. Microbiol. Biotechol., 2004, 63, 626-634.
Zhao et al., J. Org. Chem., 1998, 63, 7568.

Fig. 1A-C
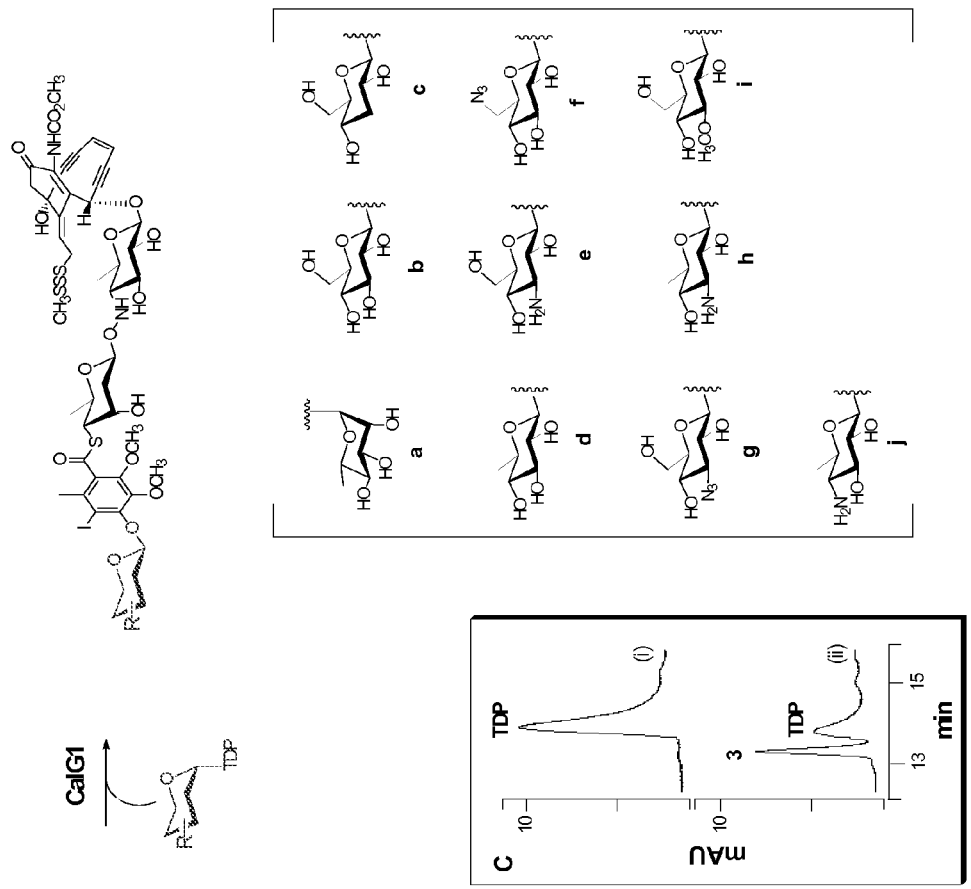
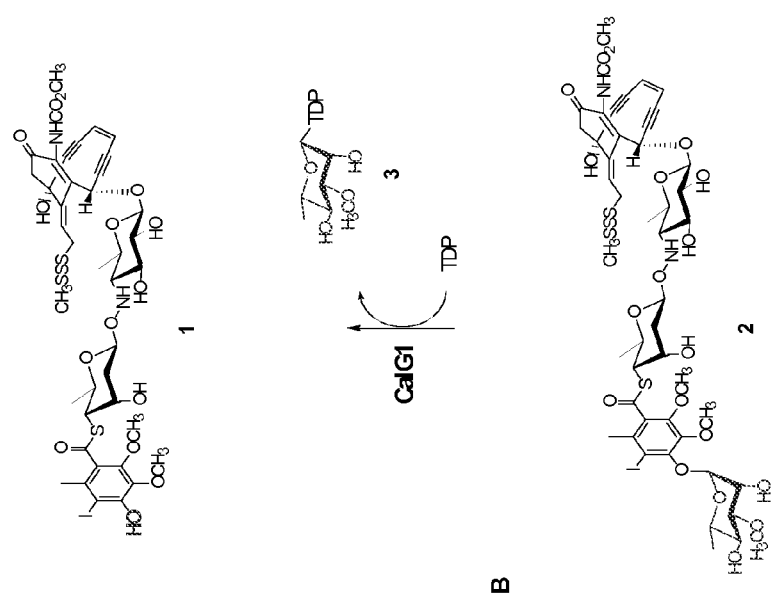

Fig. 12

Sugar Exchange (product, %conversion)

TDP-sugars →

Calicheamicins ↓

| | a | b | c | d | e | f | g | h | i | j |
|---|---|---|---|---|---|---|---|---|---|---|
| 2 | 2a 57% | 2b 43% | 2c 15% | 2d 21% | 2e 10% | 2f 40% | 2g 17% | 2h 27% | 2i 15% | 2j 18% |
| 4 | 4a 36% | 4b 67% | 4c 20% | 4d 25% | 4e 9.0% | 4f 34% | 4g 32% | 4h 18% | 4i 42% | 4j 3.5% |
| 5 | 5a 96% | 5b 98% | 5c 38% | 5d 49% | 5e 10% | 5f 79% | 5g 27% | 5h 88% | 5i 40% | 5j 4.5% |
| 6 | 6a 79% | 6b 67% | 6c 22% | 6d 35% | 6e 6.9% | 6f 68% | 6g 26% | 6h 36% | 6i 23% | 6j 7.5% |
| 7 | 7a 56% | 7b 46% | 7c 23% | 7d 32% | 7e 7.6% | 7f 42% | 7g 20% | 7h 18% | 7i 15% | 7j 24% |
| 8 | 8a 78% | 8b 76% | 8c 29% | 8d 29% | 8e 6.9% | 8f 47% | 8g 30% | 8h 51% | 8i 18% | 8j 23% |
| 9 | 9a 7.7% | 9b 26% | 9c 16% | 9d 15% | 9e 7.3% | 9f 14% | 9g 7.6% | 9h 6.0% | 9i 7.6% | 9j 9.6% |

SEQUENCE LISTING

```
<160> NUMBER OF SEQ ID NOS: 6

<210> SEQ ID NO 1
<211> LENGTH: 36
<212> TYPE: DNA
<213> ORGANISM: ARTIFICIAL SEQUENCE
<220> FEATURE:
<223> OTHER INFORMATION: PCR PRIMER

<400> SEQUENCE: 1
gccactgaag cttgacttac ccatatgcta gatatg                           36

<210> SEQ ID NO 2
<211> LENGTH: 21
<212> TYPE: DNA
<213> ORGANISM: ARTIFICIAL SEQUENCE
<220> FEATURE:
<223> OTHER INFORMATION: PCR PRIMER

<400> SEQUENCE: 2
gacggccaga tctgagcggt c                                           21

<210> SEQ ID NO 3
<211> LENGTH: 25
<212> TYPE: DNA
<213> ORGANISM: ARTIFICIAL SEQUENCE
<220> FEATURE:
<223> OTHER INFORMATION: PCR PRIMER

<400> SEQUENCE: 3
```

-continued

```
caccggagtg agcatatgcg ccagc                                              25

<210> SEQ ID NO 4
<211> LENGTH: 37
<212> TYPE: DNA
<213> ORGANISM: ARTIFICIAL SEQUENCE
<220> FEATURE:
<223> OTHER INFORMATION: PCR PRIMER

<400> SEQUENCE: 4
gtggacggca gggaatgatc aagatctggg cgcgacc                                 37

<210> SEQ ID NO 5
<211> LENGTH: 35
<212> TYPE: DNA
<213> ORGANISM: ARTIFICIAL SEQUENCE
<220> FEATURE:
<223> OTHER INFORMATION: PCR PRIMER

<400> SEQUENCE: 5
ctagacagtg acatatgtca gatcattttc tcttc                                   35

<210> SEQ ID NO 6
<211> LENGTH: 29
<212> TYPE: DNA
<213> ORGANISM: ARTIFICIAL SEQUENCE
<220> FEATURE:
<223> OTHER INFORMATION: PCR PRIMER

<400> SEQUENCE: 6
aaccctgtga gatctactca ccgcccggc                                          29
```

REVERSIBLE NATURAL PRODUCT GLYCOSYLTRANSFERASE-CATALYZED REACTIONS, COMPOUNDS AND RELATED METHODS

CROSS-REFERENCE TO RELATED APPLICATIONS

This application is a divisional of U.S. patent application Ser. No. 11/847,731 filed Aug. 30, 2007, which claims priority to U.S. Provisional Application No. 60/824,018, filed Aug. 30, 2006. Both of these applications are hereby incorporated by reference herein.

STATEMENT RELATED TO FEDERAL FUNDING

This invention was made with government support under AI052218, CA084374, GM070637 and CA113297 awarded by the National Institutes of Health. The government has certain rights in the invention.

FIELD OF THE INVENTION

The present invention generally relates to methods of using glycosyltransferases and related novel compounds. The invention specifically relates to biosynthesis of anticancer (the enediyne calicheamicin, CLM), anthelmintic agents (the macrolide avermectin, ivermectin and erythromycin) and antibiotic (the glycopeptide vancomycin, VCM) natural product-based drugs developed by reversible, bidirectional glycosyltransferase catalyzed reactions.

BACKGROUND OF THE INVENTION

Glycosyltransferases (GTs) constitute a superfamily of ubiquitous enzymes that attach carbohydrate moieties to biological molecules[1], and thus, play a role in the biosynthesis of oligosaccharides[2], glycosaminoglycans[3], glycopeptides[4], and glycosylated anticancer/anti-infective agents[5]. These enzymes are generally perceived as unidirectional catalysts that drive the formation of glycosidic bonds from nucleotide sugar (NDP-sugar) donors and aglycon acceptors[6].

In practice, these sugar-containing moieties include anticancer agents (the enediyne calicheamicin, CLM), anthelmintic agents (the macrolide avermectin, ivermectin and erythromycin) and antibiotic agents (the glycopeptide vancomycin, VCM) among other compounds. Typically these natural product-based drugs are synthesized by unidirectional GT-catalyzed reactions. However, based on the broad spectrum application of these compounds, a greater diversity and availability of combinatorial library of these compounds is desirable.

GTs are likely involved in the biosynthesis of anticancer (the enediyne calicheamicin, CLM), anthelmintic (the macrolide avermectin, AVR, ivermectin, and erythromycin) and antibiotic (the glycopeptide vancomycin, VCM) natural product-based drugs which catalyze reversible, bidirectional reactions.

Therefore, a need exists for mechanisms for introducing novel sugar moieties and conjugating these moieties with varied aglycons to generate biocombinatorial libraries of these compounds.

SUMMARY OF THE INVENTION

The present invention relates to methods of using glycosyltransferases and related novel compounds. Generally, the invention exploits the reversibility of glycosyltransferases to generate new sugars, unnatural biomolecules and numerous one-pot reactions to generate new biomolecules having varied backbones such as enediynes, vancomycins, bleomycins, anthracyclines, macrolides, pluramycins, aureolic acids, indolocarbazoles, aminglycosides, glycopeptides, polyenes, coumarins, benzoisochromanequinones, calicheamicins, erythromycins, avermectins, ivermectins, angucyclines, cardiac glycosides, steroids or flavinoids.

In one embodiment, the invention specifically relates to biosynthesis of anticancer agents (the enediyne calicheamicin, CLM), anthelmintic agents (the macrolide avermectin, ivermectin and erythromycin) and antibiotic (the glycopeptide vancomycin, VCM) natural product-based drugs developed by reversible, bidirectional, glycosyltransferase catalyzed reactions.

One exemplary embodiment of the present invention provides a method of synthesizing an independent sugar moiety A, in-situ, from a biomolecule having a sugar moiety A. This method comprises the steps of: (a) incubating the biomolecule having the sugar moiety A with a nucleotide diphosphate in the presence of a glycosyltransferase, wherein the sugar moiety A in the biomolecule is excised from the biomolecule, thereby generating the independent sugar moiety A and a biomolecule aglycon; and (b) isolating the independent sugar moiety A from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is preferably CalG1, CalG2, CalG3, CalG4, GtfD, GtfE, EryBV or AveBI. The biomolecule having the sugar moiety A is an enediyne, a vancomycin, a calicheamicin, an erythromycin, an avermectin or an ivermectin. Further, the sugar moiety is a NDP sugar and the sugar moiety A is a UDP sugar or a TDP sugar.

In one embodiment, the TDP sugar is selected from TDP-α-D-glucose, TDP-β-L-rham nose, TDP-O-methylrhamnose, TDP-6-azidoglucose, TDP-β-L-vancosamine, TDP-β-L-olendrose and TDP-β-L-mycarose. As described, this synthesis is reversible, whereby incubating the independent sugar moiety A and the biomolecule aglycon in the presence of a glycosyltransferase provides the biomolecule having the sugar moiety A.

Another exemplary embodiment of the present invention provides a method of exchanging a sugar moiety, in-situ, between (i) an independent sugar moiety B and (ii) a biomolecule having a sugar moiety A. This method comprises the steps of: (a) incubating the independent sugar moiety B with the biomolecule having sugar moiety A in the presence of a glycosyltransferase, wherein the sugar moiety A is excised from the biomolecule and the sugar moiety B is ligated in its place, thereby generating the independent sugar moiety A and a biomolecule having sugar B; and (b) isolating the independent sugar moiety A and the biomolecule having sugar moiety B from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is preferably CalG1, CalG2, CalG3, CalG4, GtfD, GtfE, EryBV or AveBI. Further, the biomolecule is an enediyne, a vancomycin, a calicheamicin, an erythromycin, an avermectin or an ivermectin and the sugar moiety A or B is independently selected from:

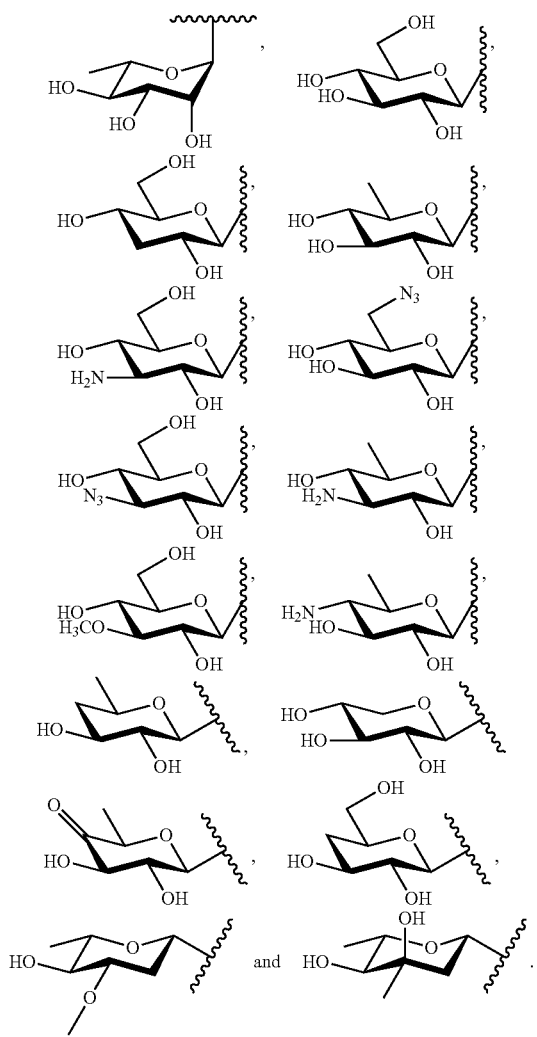

As described here, the sugar exchange is reversible, whereby incubating the independent sugar moiety A and the biomolecule having sugar moiety B in the presence of a glycosyltransferase results in the independent sugar moiety B and the biomolecule having a sugar moiety A.

Yet another exemplary embodiment of the present invention provides a method of generating a biomolecule A having a sugar moiety A from a biomolecule B having the sugar moiety A, in situ. This method comprises the steps of: (a) incubating the biomolecule A, biomolecule B having the sugar moiety A and a nucleotide diphosphate in the presence of a glycosyltransferase wherein (i) the sugar moiety A of the biomolecule B is excised from the biomolecule B, thereby generating an independent sugar moiety A and a biomolecule aglycon B; and (ii) the independent sugar moiety A and the biomolecule A are ligated, thereby generating the biomolecule A having the sugar moiety A; and (b) isolating the biomolecule A having sugar moiety A from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method the glycosyltransferase is CalG1, CalG2, CalG3, CalG4, GtfD, GtfE, EryBV or AveBI. The biomolecule A or biomolecule B is an enediyne, a vancomycin, a calicheamicin, an erythromycin, an avermectin, an ivermectin or combinations thereof.

As described here, the method of generating biomolecule A having the sugar moiety A from the biomolecule B having the sugar moiety A is reversible, such that incubating the biomolecule A having the sugar moiety A and the biomolecule aglycon B in the presence of a glycosyltransferase results in the biomolecule B having the sugar moiety A.

Another exemplary embodiment of the present invention provides a method of generating a biomolecule A having a sugar moiety A and a biomolecule B having a sugar moiety B from a biomolecule B having the sugar moiety A and a biomolecule A having the sugar moiety B. This method comprises the steps of: (a) incubating the biomolecule A having the sugar moiety B, biomolecule B having the sugar moiety A and a nucleotide diphosphate in the presence of a glycosyltransferase wherein (i) the sugar moiety A of the biomolecule B is excised from the biomolecule B, thereby generating an independent sugar moiety A and a biomolecule aglycon B; (ii) the sugar moiety B of the biomolecule A is excised from the biomolecule A, thereby generating an independent sugar moiety B and a biomolecule aglycon A; and (iii) the independent sugar moiety A and the biomolecule A are ligated, the independent sugar moiety B and the biomolecule B are ligated, thereby generating the biomolecule A having the sugar moiety A and biomolecule B having the sugar moiety B; and (b) isolating the biomolecule A having the sugar moiety A and the biomolecule B having from the sugar moiety B from step (a)(iii), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is preferably CalG1, CalG2, CalG3, CalG4, GtfD, GtfE, EryBV or AveBI. The biomolecule A or biomolecule B is an enediyne, a vancomycin, a calicheamicin, an erythromycin, an avermectin, an ivermectin or combinations thereof. As described, this method of generating the biomolecule A having the sugar moiety A and the biomolecule B having the sugar moiety B is reversible, such that incubating the biomolecule A having the sugar moiety A and the biomolecule B having the sugar moiety B in the presence of a glycosyltransferase results in the biomolecule B having the sugar moiety A and the biomolecule A having the sugar moiety B.

In yet another exemplary embodiment, the present invention provides a method of generating a library of isolated glycosylated biomolecules comprising transferring a sugar moiety from a first biomolecule backbone to a second biomolecule backbone in the presence of a glycosyltransferase wherein the sugar moiety is transferred from the first biomolecule backbone to the second biomolecule backbone thereby generating a non-naturally occurring glycosylated biomolecule, wherein the biomolecule backbone is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the first and the second glycosylated biomolecule backbones are independently selected from an enediyne, a vancomycin, a calicheamicin, an avermectin, an ivermectin, an erythromycin and combinations thereof. The sugar moiety is selected from:
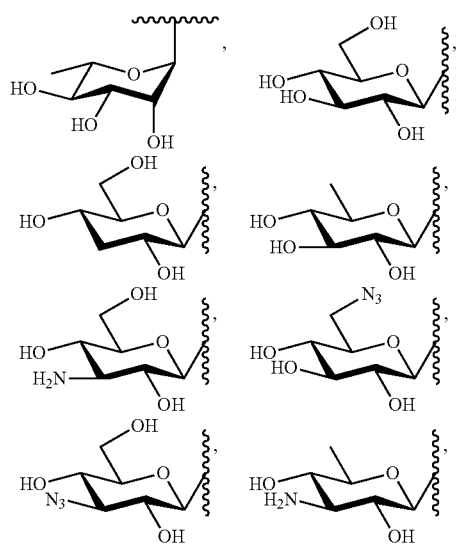
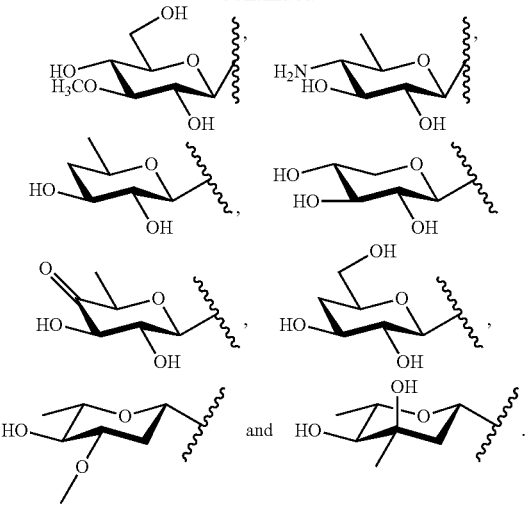
Another embodiment of the present invention provides a glycoside analog of Formula I through XIV having a non-native sugar moiety, wherein the glycoside analog is selected from:
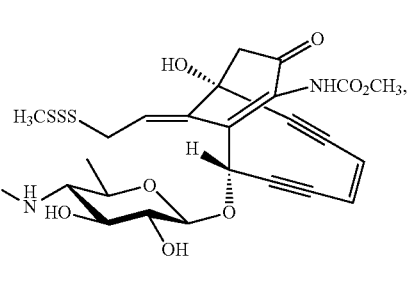
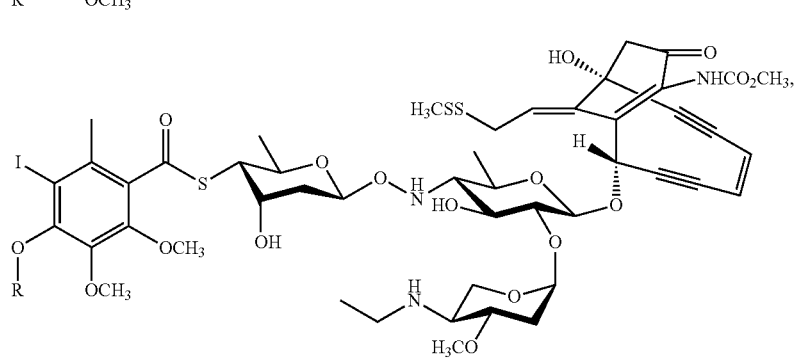
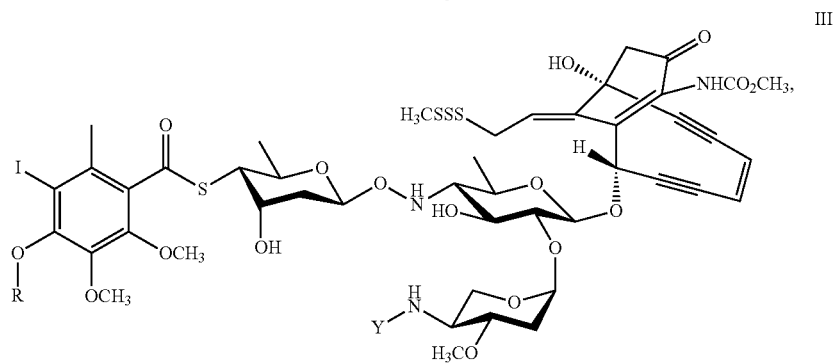

-continued
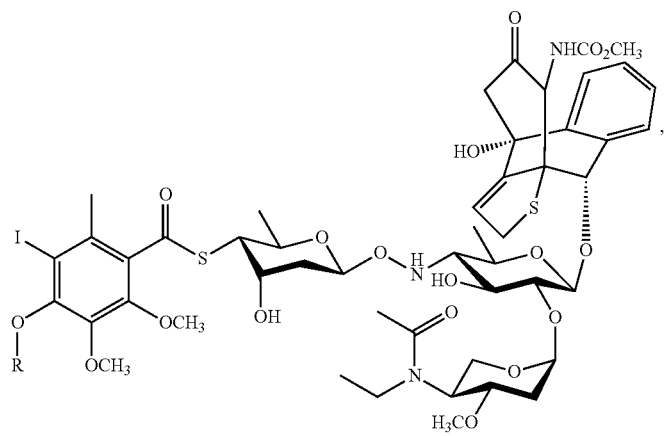
IV
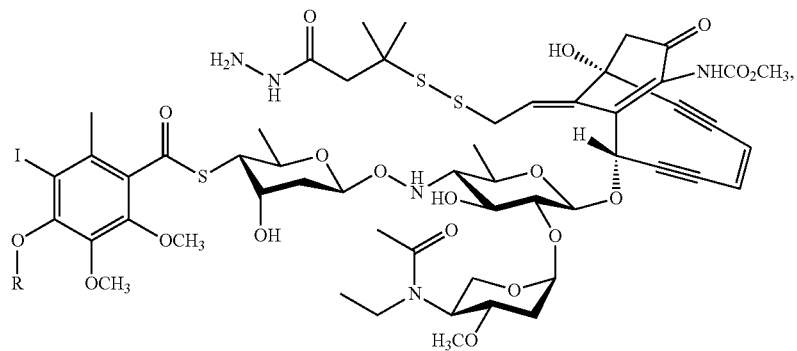
V
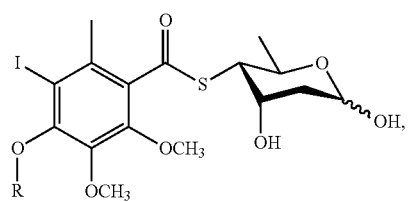
VI
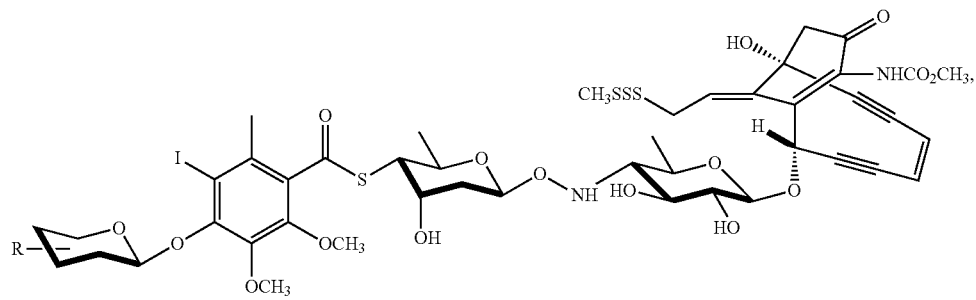
VII

VIII
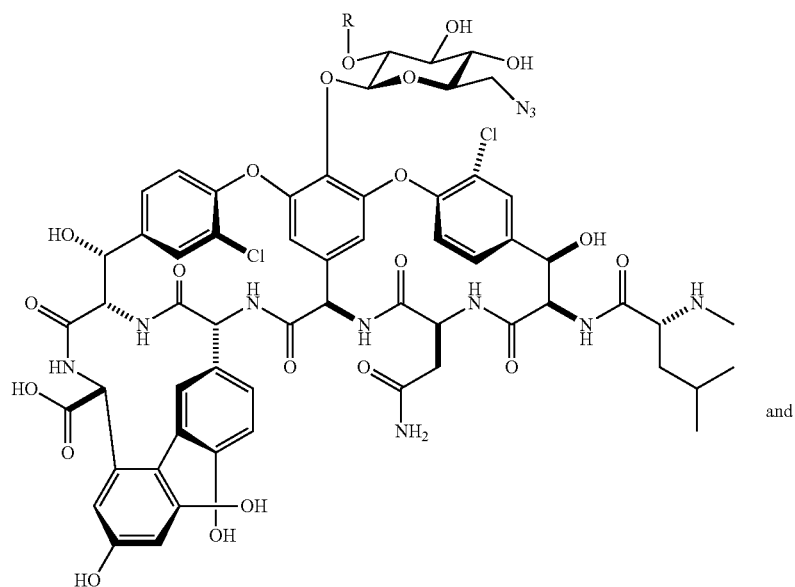
and
IX
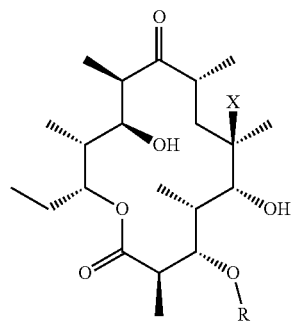
X
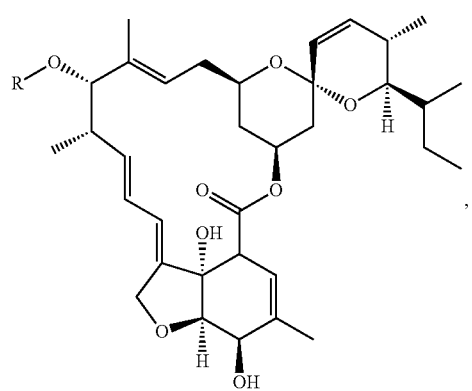

XI
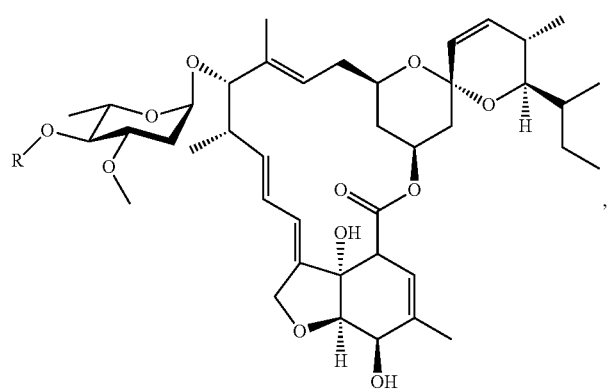
XII
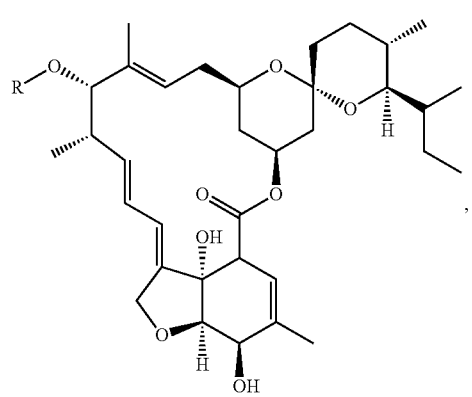
XIII
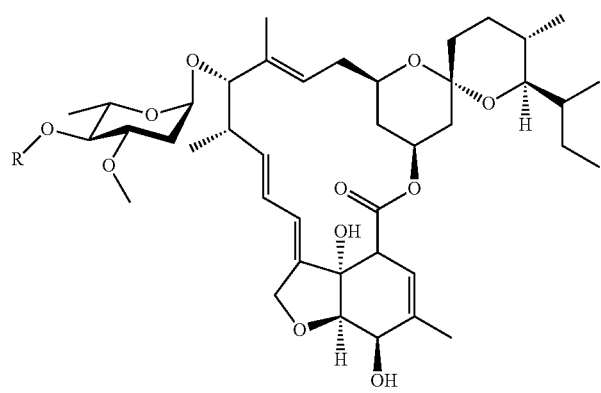
and
XIV
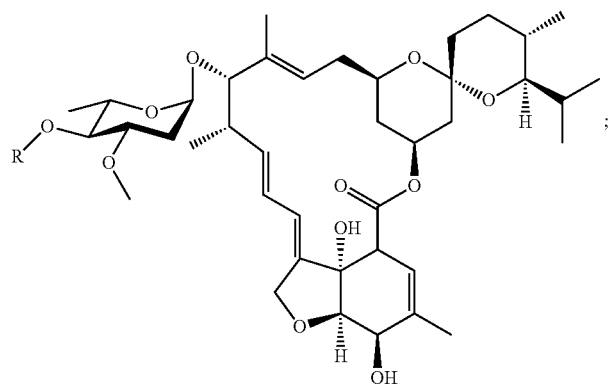
;
(b) optionally wherein the glycoside analog of Formula II, III, IV or V further includes a 3'-O-methylrhamnose moiety; (c) wherein Y is independently selected from $CH(CH_3)_2$, $CH_2(CH_3)_2$, $CH_2CH_3$ or $CH_3$; (d) wherein X is independently selected from H or OH; and (e) wherein, R is independently selected from a sugar moiety selected from:

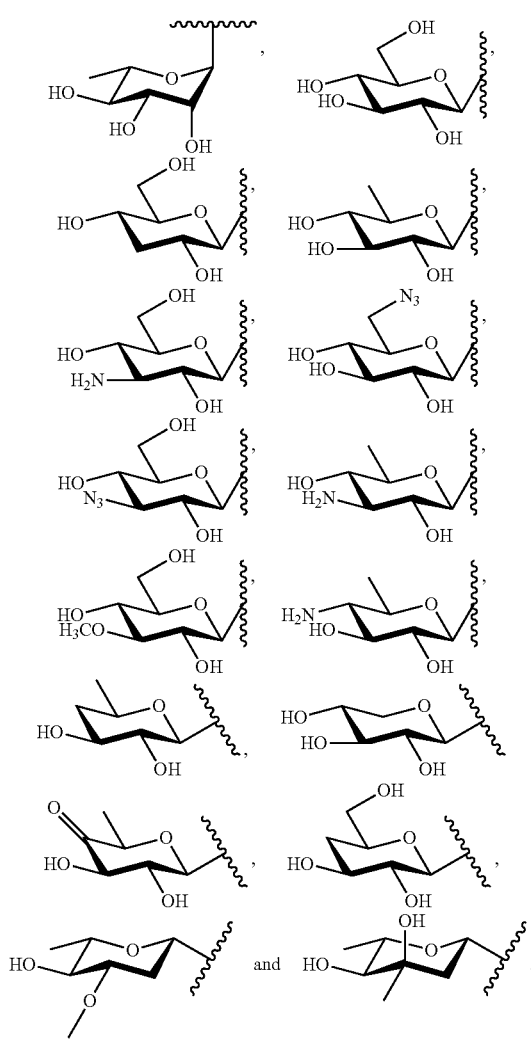

Other objects, features and advantages of the present invention will become apparent after review of the specification, claims and drawings.

BRIEF DESCRIPTION OF THE DRAWINGS

FIG. 12. Efficiency of CalG1-catalyzed 'sugar exchange' reactions. The sugar exchange reactions were carried out by co-incubating 50 µM CLM (2, 4-9) with 300 of TDP-sugar (FIG. 6A) in the presence of 10 µM CalG1 at 30° C. for 3 hrs. The reactions were analyzed by RP-HPLC as described in the Materials and Methods. The percent conversion for the resultant sugar-exchanged product was calculated from the corresponding HPLC traces by dividing the integrated area of glycosylated product by the sum of the integrated area of the product and remaining CLM substrate. The slight decrease in sugar exchange efficiency for glycosides c-j is most likely due to a higher concentration of TDP in these reactions. TDP is a by-product of the nucleotidylyltransferase ($E_p$) reaction by which these NDP-sugars were generated. Higher concentrations of TDP favor the "substrate" side of the equilibrium and disfavor products, thereby lowering sugar exchange efficiency. The following derivatives were confirmed by LC-MS: 4f, calc. 1408.3, [M+H]$^+$ 1409.3; 5c, calc. 1353.3, [M+H]+ 1354.3; 5f, calc. 1394.3, [M+H]$^+$ 1395.3; 5j, calc. 1352.3, [M+H]$^+$ 1353.3; 6f, calc. 1380.2, [M+H]$^+$ 1381.3; 8f, calc. 1362.3, [M+H]$^+$ 1363.3; 7f, calc. 1504.4, [M+H]+ 1505.4; 9f, calc. 1360.3, [M+H]$^+$ 1361.3.

Figure 7:
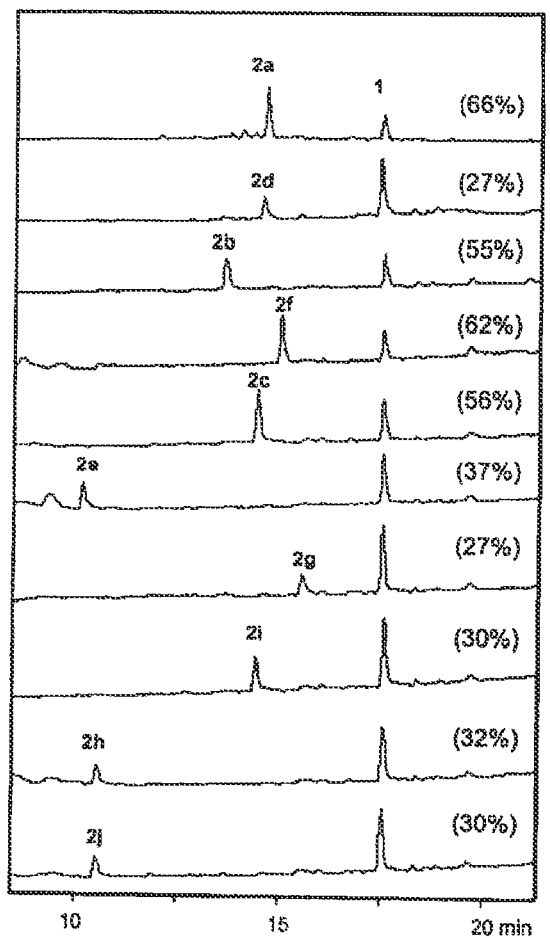
FIG. 7. The sugar substrate flexibility of CalG1. RP-HPLC analysis of CalG1-catalyzed reactions in the forward direction using PsAg (1) as an acceptor and a pool of TDP-sugar donors (FIG. 6) revealed 10 CalG1 substrates. Percent conversions are given in parentheses. The assays were carried out in a total volume of 100 µl of buffer (10 mM Tris-HCl, pH7.5, 1 mM MgCl$_2$) containing 50 µN aglycon, 300 µM TDP-sugar, 10 µM CalG1, and were incubated at 30° C. for 12 hrs. Products were confirmed by LC-MS: 1, calc. 1050.1, [M+H] 1051.1; 2a, calc. 1196.2, [M+H]$^+$ 1197.2; 2b, calc. 1212.1, [M+H]$^+$ 1213.2; 2c, calc. 1196.2, [M+H]$^+$ 1197.2; 2d, calc. 1196.2, [M+H]$^+$ 1197.2; 2e, calc. 1211.2, [M+H]$^+$ 1212.1; 2f, calc. 1237.2, [M+H]$^+$ 1238.2; 2g, calc. 1237.2, [M+H]$^+$ 1238.2; 2h, calc. 1195.2, [M+H]$^+$ 1196.3; 2i, calc. 1226.2, [M+H]$^+$ 1 227.3; 2j, calc. 1195.2, [M+H]$^+$ 1196.4.
Figure 8:
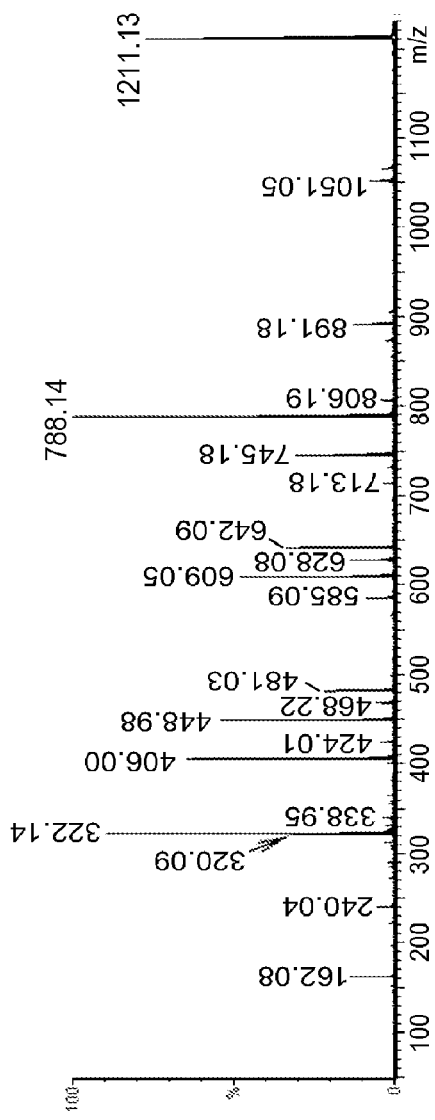
FIG. 8. MS/MS analysis of the regiospecificity of CalG1-catalyzed reactions. Panels A to D show the MS/MS fragmentation of protonated compounds 2 (calicheamicin $\alpha_3^I$, 1211.13$^+$, 16.0 eV), 2b (1213.16$^+$, 16.0 eV), 2d (1197.17$^+$, 16.0 eV), and 5 (calicheamicin $\gamma_1^I$, 1368.12$^+$, 16.0 eV), respectively. In panel D, the abundance of the ions between m/z 200-1300 was magnified by 10 fold. The identities of the major fragment ions produced by glycosidic cleavages are labeled in the scheme below each MS/MS spectrum.
Figure 8:
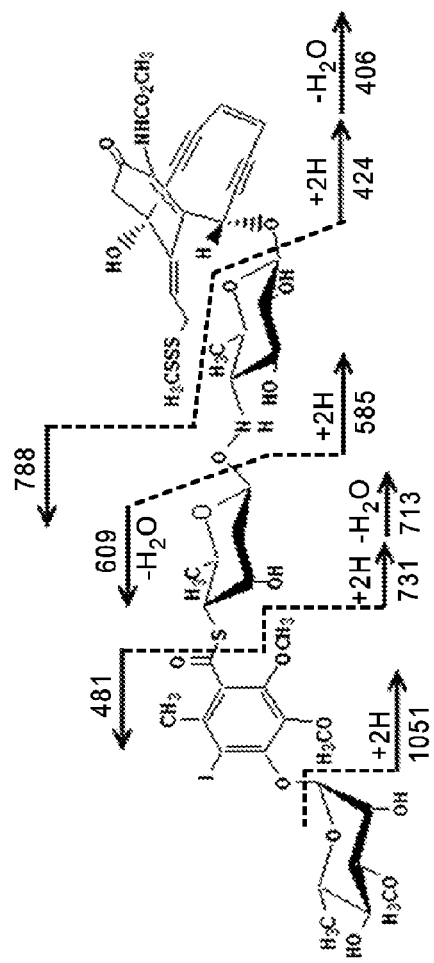
Figure 8:
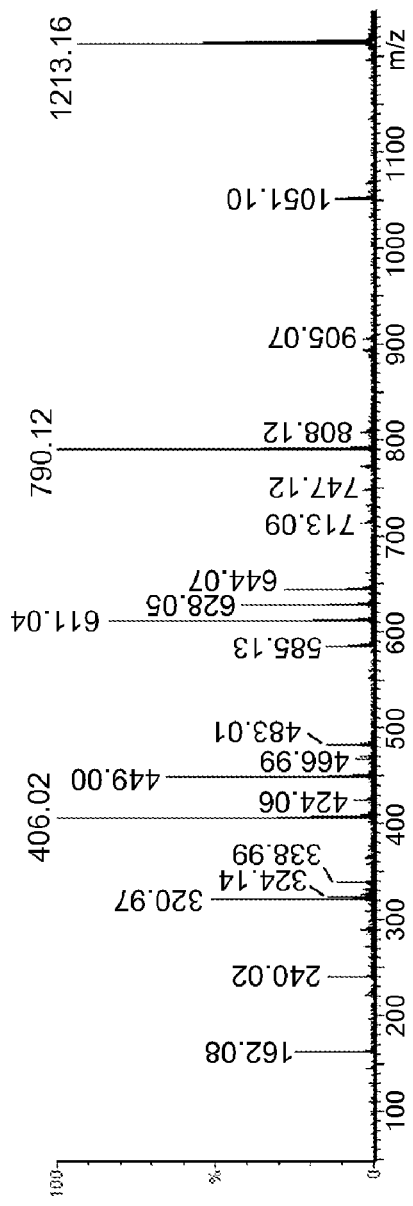
Figure 8:
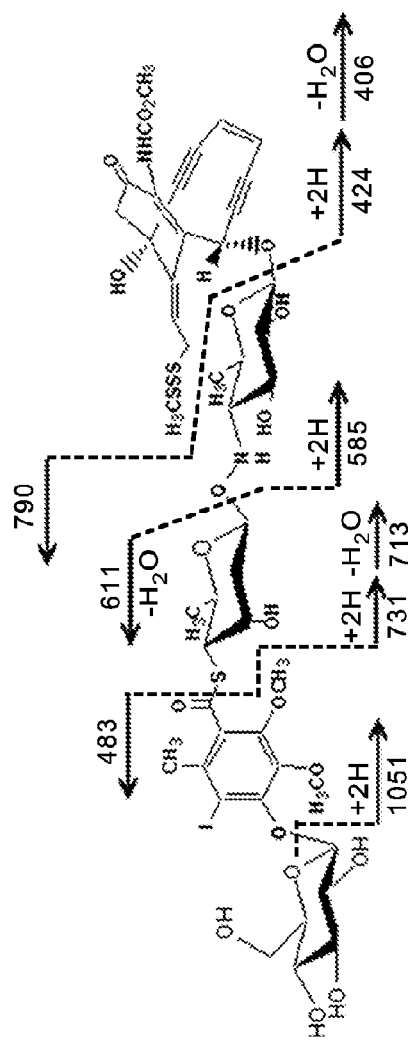
Figure 8:
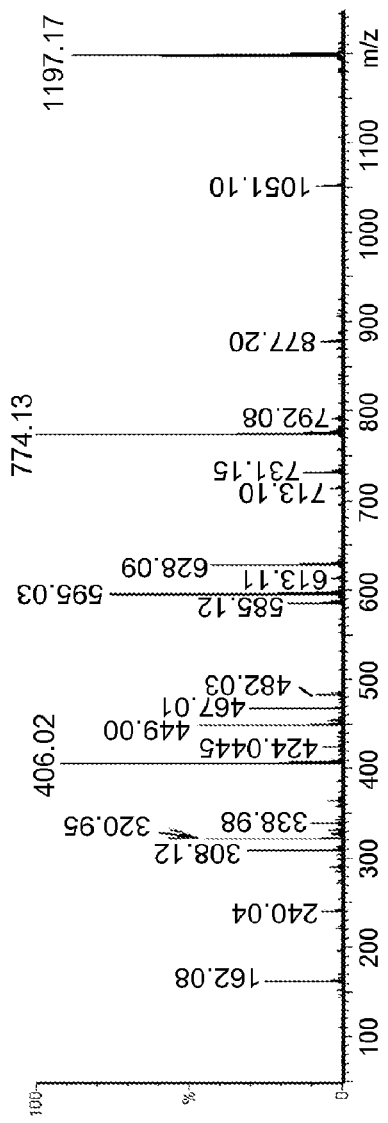
Figure 8:
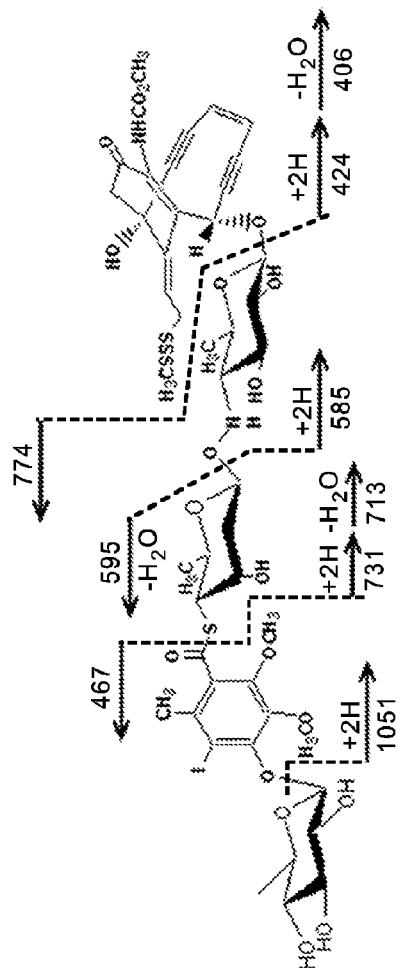
Figure 8:
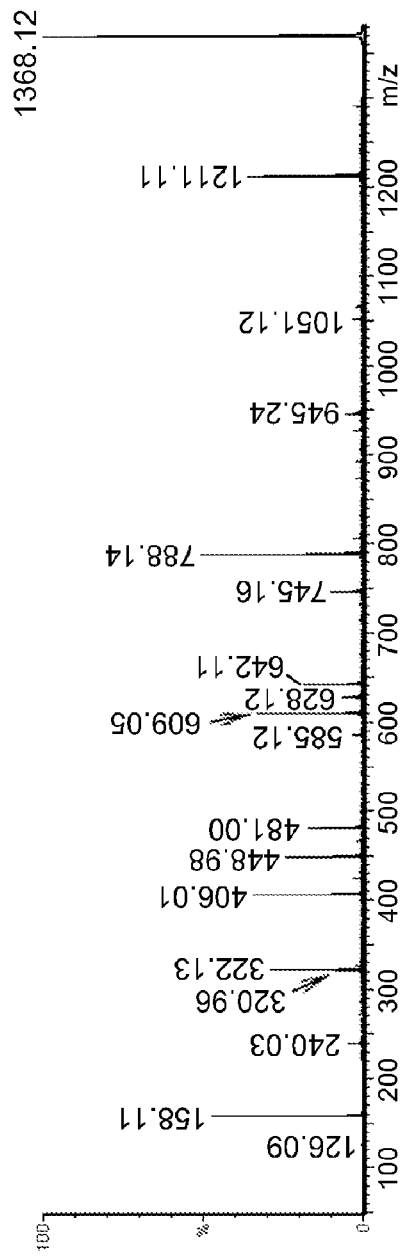
Figure 8:
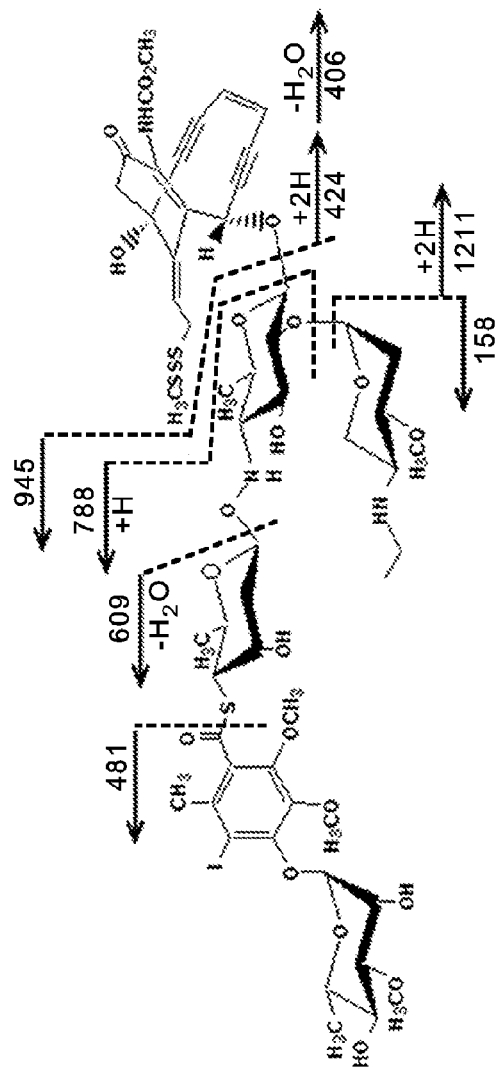
Figure 10:
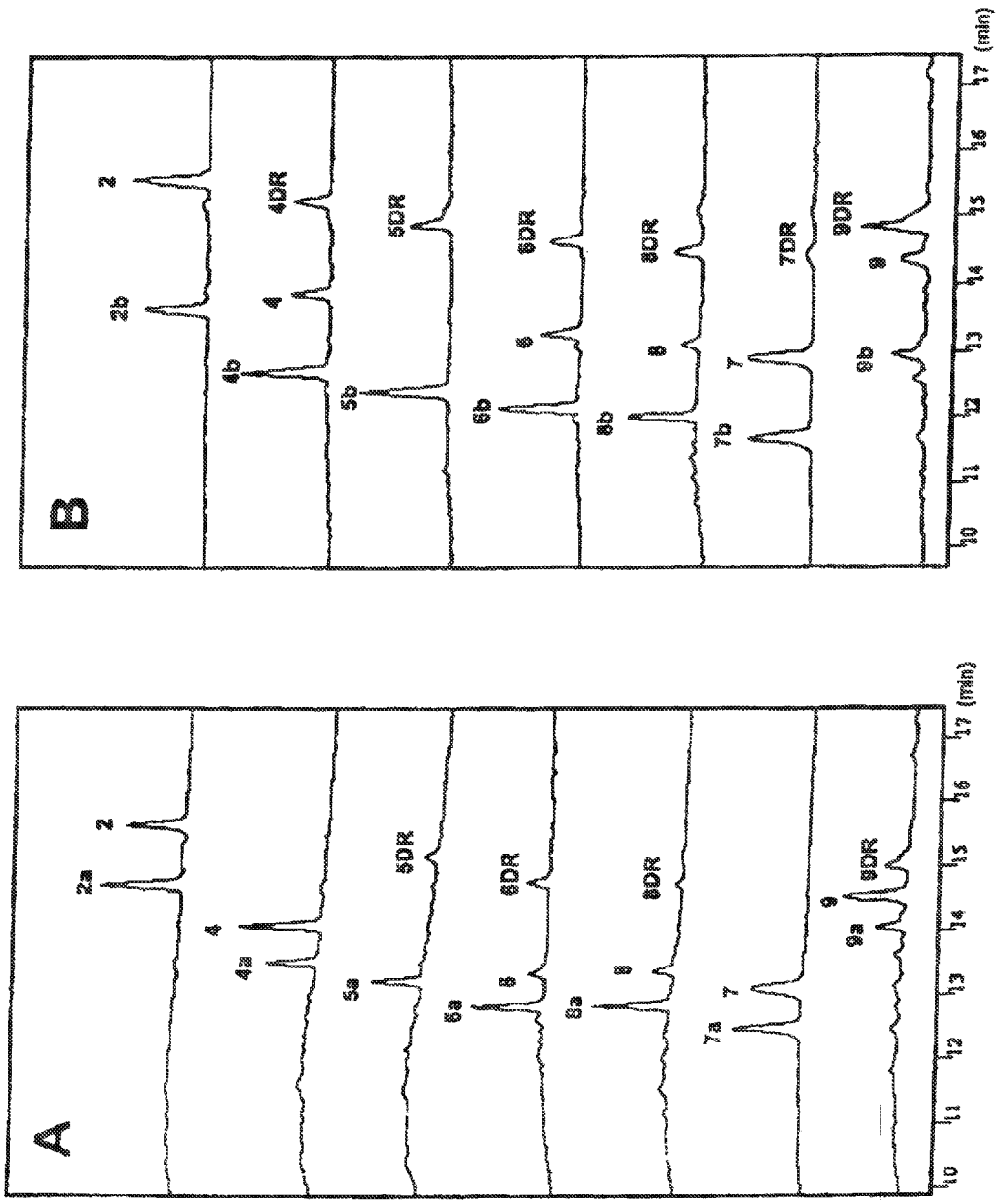
FIG. 10. Representative CalG1-catalyzed 'sugar exchange' reactions. RP-HPLC analysis of CalG1-catalyzed reactions with 7 parent CLM derivatives—$\alpha_3^I$ (2), $\beta_1^I$ (4), $\gamma_1^I$ (5), $\delta_1^I$ (6), DMH Nac $\gamma_1^I$ (7), $\gamma_2^I$ (8) and Nac $\epsilon_1^I$ (9) with TDP-β-L-rhamnose (A) or TDP-α-D-glucose (B). The "DR" designation stands for "derhamnosylated" (meaning removal of the 3'-O-methylrhamnose unit). Structures of "DR" derivatives are available in FIG. 11. The following compounds were confirmed by LC-MS: 4, calc. 1381.3, [M+H]$^+$ 1382.3; 4DR, calc. 1221.2, [M+H]$^+$ 1222.2; 4a, calc. 1367.3, [M+H]$^+$ 1368.3; 4b, calc. 1383.3, 5, calc. 1367.3, [M+H]$^+$ 1368.3; 5DR, calc. 1207.3, [M+H]$^+$ 1208.3; 5a, calc. 1353.3, [M+H]$^+$ 1354.3; 5b, calc. 1369.3, [M+H]$^+$ 1370.3; [M+H]$^+$ 1384.3; 6, calc. 1353.3, [M+H]$^+$ 1354.3; 6DR, calc. 1193.3, [M+H]$^+$ 1194.3; 6a, calc. 1339.3, [M+H]$^+$ 1340.3; 6b, calc. 1355.3, [M+H]$^+$ 1356.3; 7, calc. 1477.3, [M+H]$^+$ 1478.3, [M+Na]+, 1499.3; 7DR, calc. 1317.3, [M+Na]+1340.4; 7a, calc. 1463.4, [M+H]+1464.3; 7b, calc. 1479.3, [M+H]$^+$ 1480.3; 8, calc. 1335.3, [M+H]$^+$ 1336.3; 8DR, calc. 1175.2, [M+H]$^+$ 1176.2; 8a, calc. 1321.3, [M+H]$^+$ 1322.3; 8b, calc. 1337.3, [M+H]+1338.3; 9, calc. 1333.3, [M+H]$^+$ 1334.3; 9a, calc. 1319.3, [M+H]$^+$ 1320.3; 9b, calc. 1335.3, [M+H]$^+$ 1336.3.

were confirmed by LC-MS to give mass values consistent with those previously determined (FIGS. 7, 8 and 10).

Figure 14:
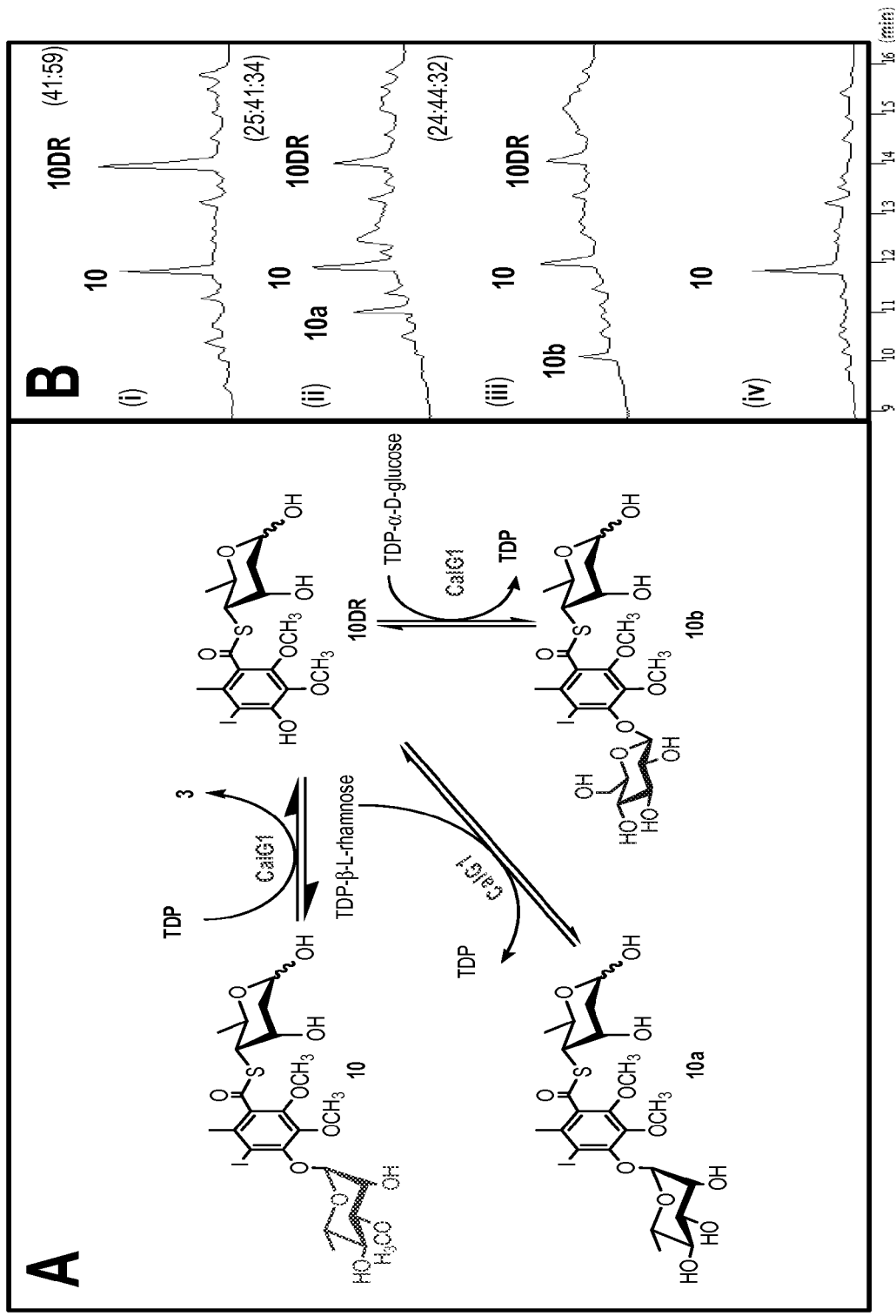

FIG. 14. CalG1-catalyzed reverse glycosyltransfer and sugar exchange reactions on a minimal substrate. (A) Scheme for the transformation of 10 to 10DR, 10a and 10d. (B) RP-HPLC analysis of CalG1-catalyzed reactions. (i) Co-incubation of 20 μM 10 and 2 mM TDP with 10 μM CalG1 led to the formation of 10DR. (ii) Co-incubation of 20 μM 10, 300 μM TDP-β-L-rhamnose and 0.1 mM TDP with 10 μM CalG1 led to the formation of product 10a and by-product 10DR. (iii) Co-incubation of 20 μM 10, 300 μM TDP-α-D-glucose and 0.1 mM TDP with 10 μM CalG1 led to the formation of product 10b and by-product 10DR. (iv) Co-incubation of 20 μM 10 and 2 mM TDP in the absence of CalG1 resulted in no reaction. The "DR" designation stands for "derhamnosylated" (meaning removal of the 3'-O-methylrhamnose unit). Compound distributions are indicated in parentheses. The following derivatives were confirmed by LC-MS: 10, calc. 644.1, [M+H]+ 645.1; 10DR, calc. 484.0, [M+H]+ 485.0; 10a, calc. 630.1, [M+H]+ 631.1; 10b, calc. 646.1, [M+H]+ 647.1.

Figure 15:
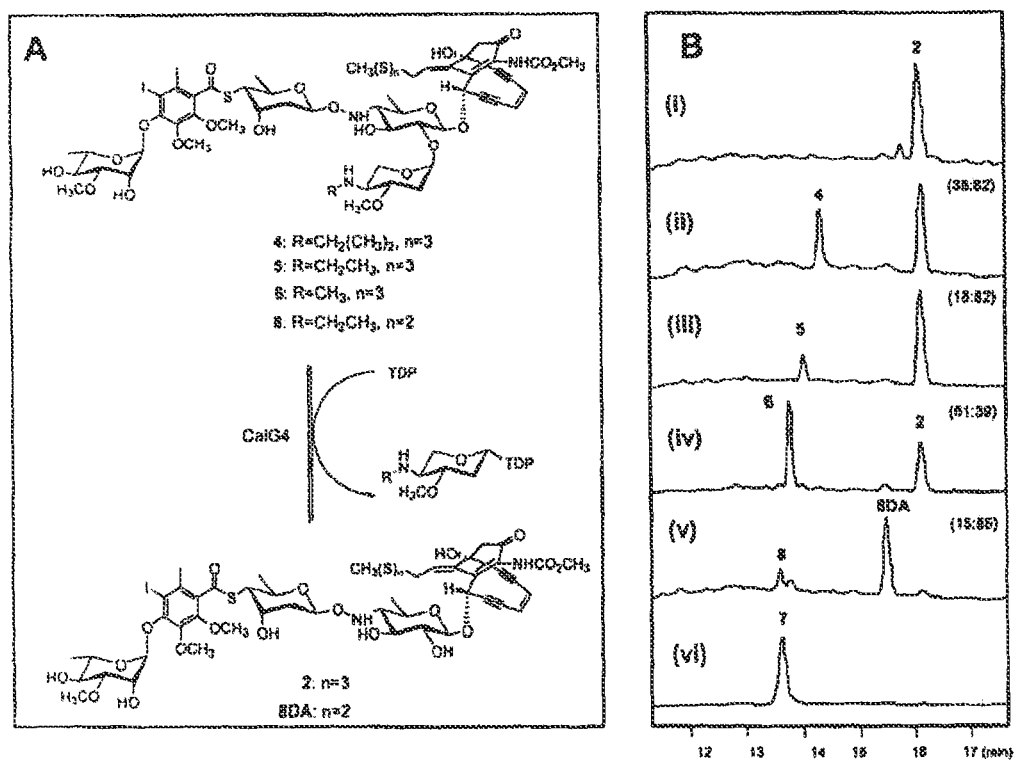

FIG. 15. CalG4-catalyzed reverse glycosyltransfer. (A) Scheme for CalG4-catalyzed reverse reactions. (B) RP-HPLC analysis of TDP-dependent reverse CalG4 catalysis. (i) Co-incubation of 2 and TDP with CalG4 resulted in no reaction, demonstrating that CalG4 did not remove the 3'-O-methyl-rhamnose moiety from 2. Co-incubation of TDP and 4 (ii), 5 (iii), or 6 (iv) with CalG4 led to the formation of the same reverse glycosyltransfer product 2, demonstrating that CalG4 was specific for the aminopentose moiety in CLMs. (v) Co-incubation of TDP and 8 with CalG4 led to the formation of product 8DA. The "DA" designation stands for "de-aminopentosylated", meaning the removal of the aminopentose unit. (vi) Co-incubation of TDP and 7 with CalG4 resulted in no reaction, demonstrating the incompatibility of the N-acetyl group with CalG4. These reactions were performed with 2 mM TDP, 50 μN CLMs, and in the presence or absence of 10 μM CalG4. Co-incubation of UDP (or ADP, CDP, GDP) and CLMs (2, 4-8) with CalG4 resulted in no reaction. Compound distributions are indicated in parentheses. The product in (v) was confirmed by LC-MS: 8DA, calc. 1178.2, [M+H]+ 1179.2. The formation of 2 in (ii), (iii) and (iv) was confirmed by LC-MS in all cases: calc., 1210.1, [M+H]+ 1211.1.

Figure 16:
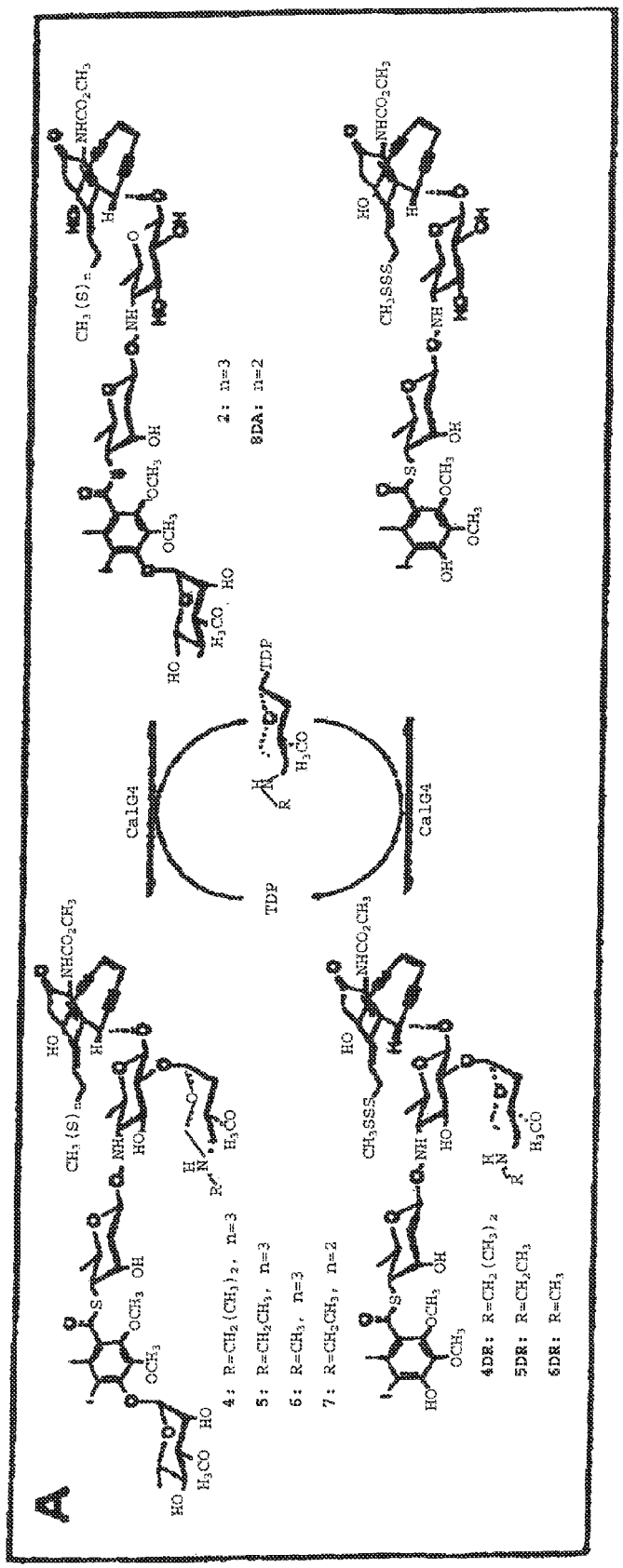
Figure 16:
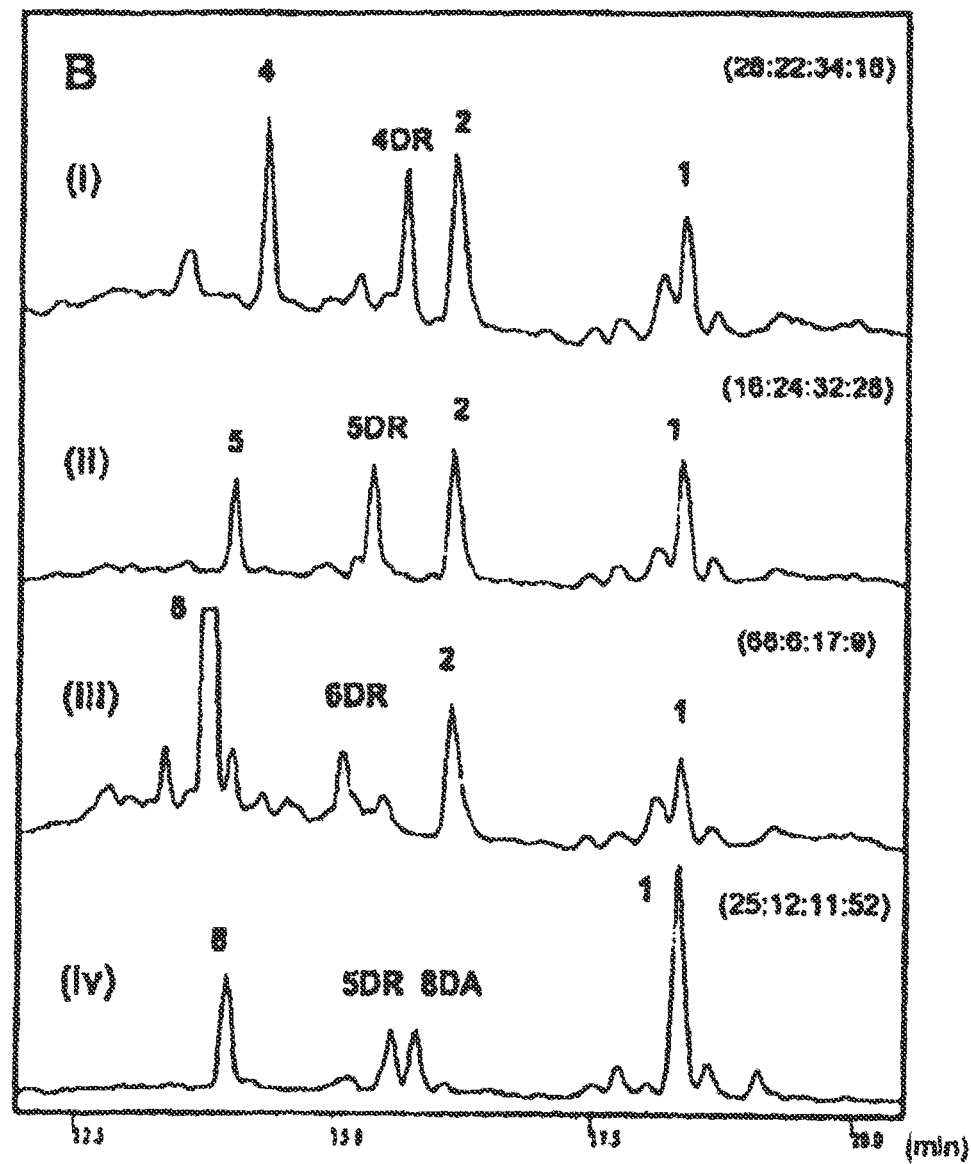

FIG. 16. CalG4-catalyzed aglycon exchange reactions. (A) Scheme for CalG4-catalyzed aglycon exchange reactions. (B) RP-HPLC analysis of CalG4-catalyzed aglycon exchange reactions. (i) Co-incubation of 4, 1, and TDP with CalG4 led to the formation of product 4DR and by-product 2. (ii) Co-incubation of 5, 1, and TDP with CalG4 led to the formation of product 5DR and by-product 2. (iii) Co-incubation of 6, 1, and TDP with CalG4 led to the formation of product 6DR and by-product 2. (iv) Co-incubation of 8, 1, and TDP with CalG4 led to the formation of products 5DR and by-product 8DA. These reactions were performed using 200 μM TDP, 50 μM CLMs (except for 100 μM 6), in the presence of 10 μM CalG4. The "DR" designation stands for "de-rhamnosylated", meaning the removal of the 3'-O-methylrhamnose unit. The "DA" designation stands for "de-aminopentosylated", meaning the removal of the aminopentose unit. Compound distributions are indicated in parentheses. All compounds were confirmed by LC-MS analysis to mass values consistent with those previously determined (FIGS. 10 and 15).

Figure 17:
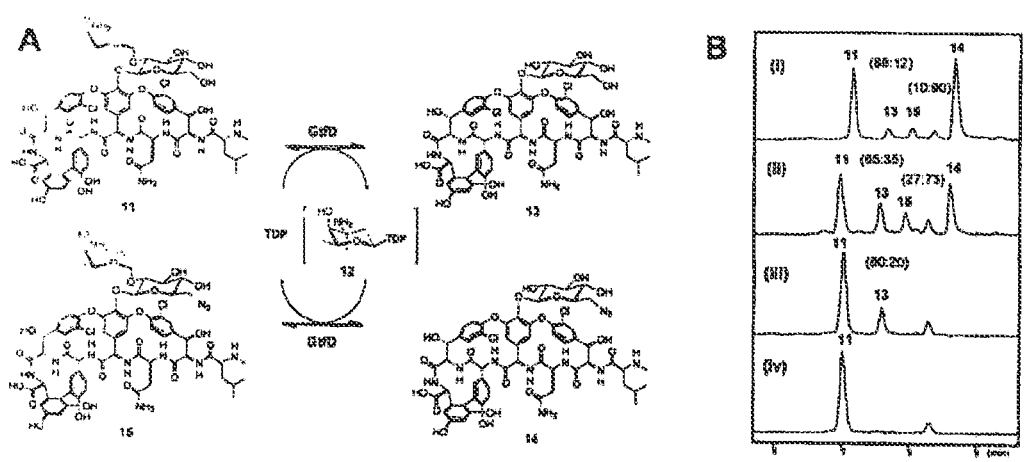

FIG. 17. GtfD-catalyzed aglycon exchange. (A) Scheme for a representative GtfD-catalyzed aglycon exchange reaction. (B) RP-HPLC analysis of GtfD-catalyzed reactions. (i) Co-incubation of 100 μM 11, 100 μM 14, and 0.1 mM TDP with 12 μM GtfD led to the formation of product 15 and by-product 13. Percent conversion (10%) was calculated using the integration areas of peaks 14 and 15. (ii) Co-incubation of 100 μM 11, 100 μM 14, and 1 mM TDP with 12 μM GtfD led to the formation of product 15 and by-product 13. Percent conversion (27%) was calculated using the integration areas of peaks 14 and 15, revealing a higher conversion upon increasing [TDP]. (iii) Co-incubation of 100 μM 11 and 1 mM TDP with 12 μM GtfD led to the formation of 13. (iv) Co-incubation of 100 μM 11 and 1 mM TDP in the absence of GtfD resulted in no reaction. Compound distributions are indicated in parentheses. All products were confirmed by LC-MS: 11, calc. 1447.4, [M+H]+ 1448.4; 13, calc. 1304.3, [M+H]+ 1305.2; 14, calc. 1329.3, [M+H]+ 1 330.3; 15, calc. 1472.4, [M+H]+ 1473.3.

Figure 18:
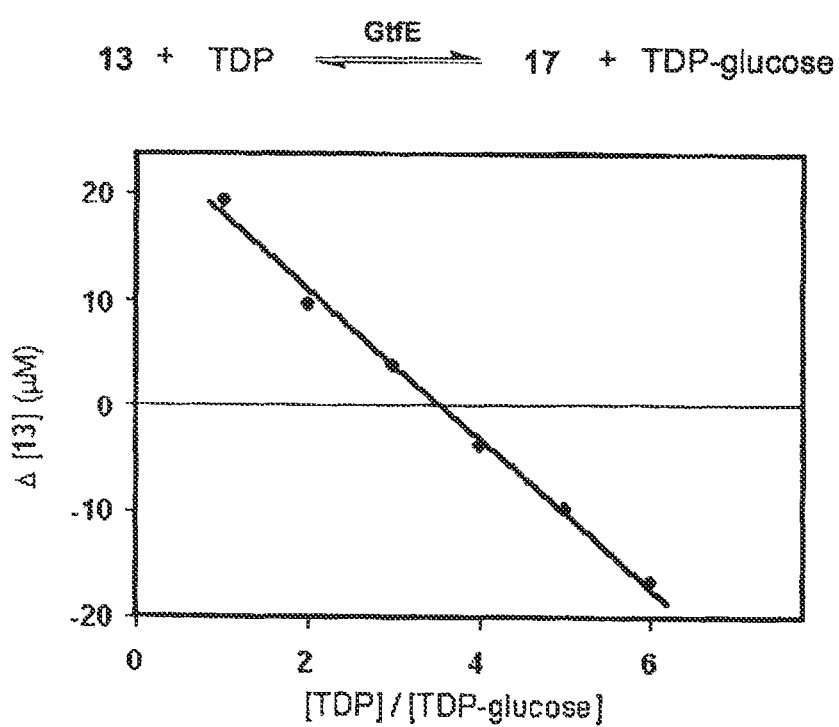

FIG. 18. Determination of the equilibrium constant ($K_{eq}$) for the native GtfE-catalyzed reaction. The $K_{eq}$ was measured in duplicate via a series of reactions under saturation conditions in which the ratio of [TDP]/[TDP-glucose] was varied from 1 to 6 while the initial ratio of [13]/[17] was fixed at 56/44. The change in [13] after a 6 h incubation at 37° C. was determined by RP-HPLC and plotted against [TDP]/[TDP-glucose]. The value of the abscissa axis that corresponds to the 0-value intercept of the ordinate axis is the uncorrected $K_{eq}$, which was corrected by multiplying by the initial [13]/[17], as this ratio was not exactly 1 (i.e. $K_{eq}$ was determined using the equation $K_{eq}=([TDP]/[TDP\text{-glucose}]\times[13]/[17])$).

Figure 19:
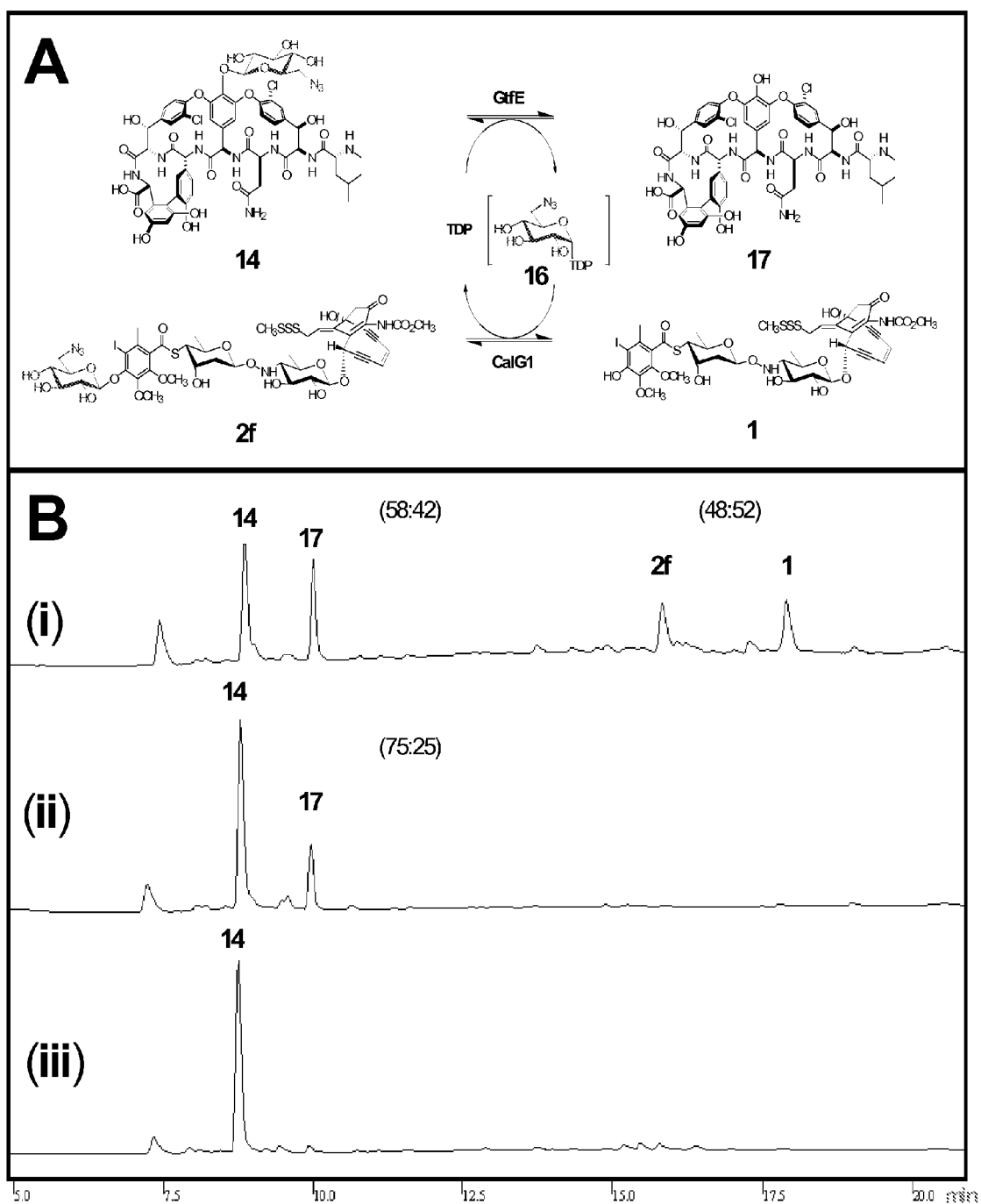

FIG. 19. Tandem two-GT-catalyzed aglycon exchange. (A) Scheme for the GtfE/CalG1-catalyzed transformation of 1 to 2f. (B) RP-HPLC analysis of a tandem two-GT-catalyzed reaction. (i) Co-incubation of 100 μM 14, 50 μM 1, and 0.1 mM TDP with 10 μM GtfE and 10 μM CalG1 led to the formation of 2f and by-product 17. The percent conversion is indicated in parentheses. (ii) Co-incubation of 100 μN 14 and 0.1 mM TDP with 10 μM GtfE led to the formation of 17 (25%). (iii) Co-incubation of 100 μM 14 and 1 mM TDP in the absence of GtfE resulted in no reaction. Products were confirmed by LC-MS to give values consistent with those previously determined (FIG. 7 and reference 76).

Figure 20:
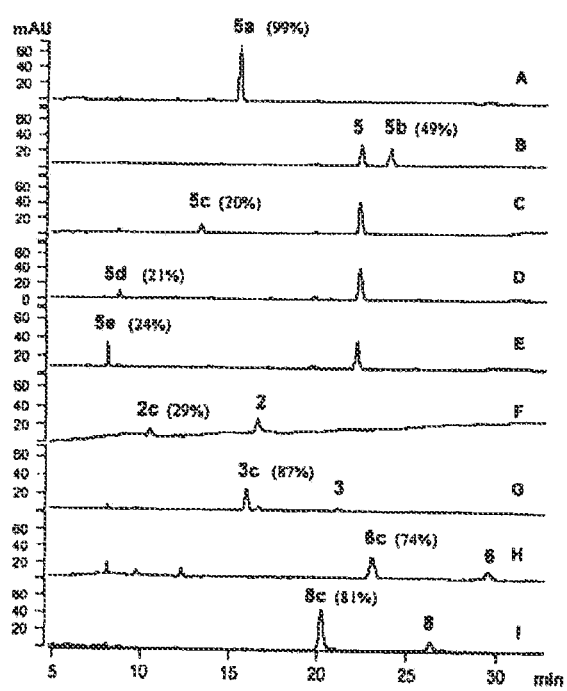

FIG. 20. RP-HPLC analysis of representative AveBI reactions. Panels A-E depicted the formation of glycosides of 105a-105e in AveBI reactions with 105 as an acceptor. Panels F-I represented the attachment of xylose to aglycons 102, 103, 105 and 108 to form 102c, 103c, 105c and 108c by AveBI, respectively. Conversion rates for each reaction were indicated in parentheses. Assay and HPLC conditions are available in following sections.

Figure 21:
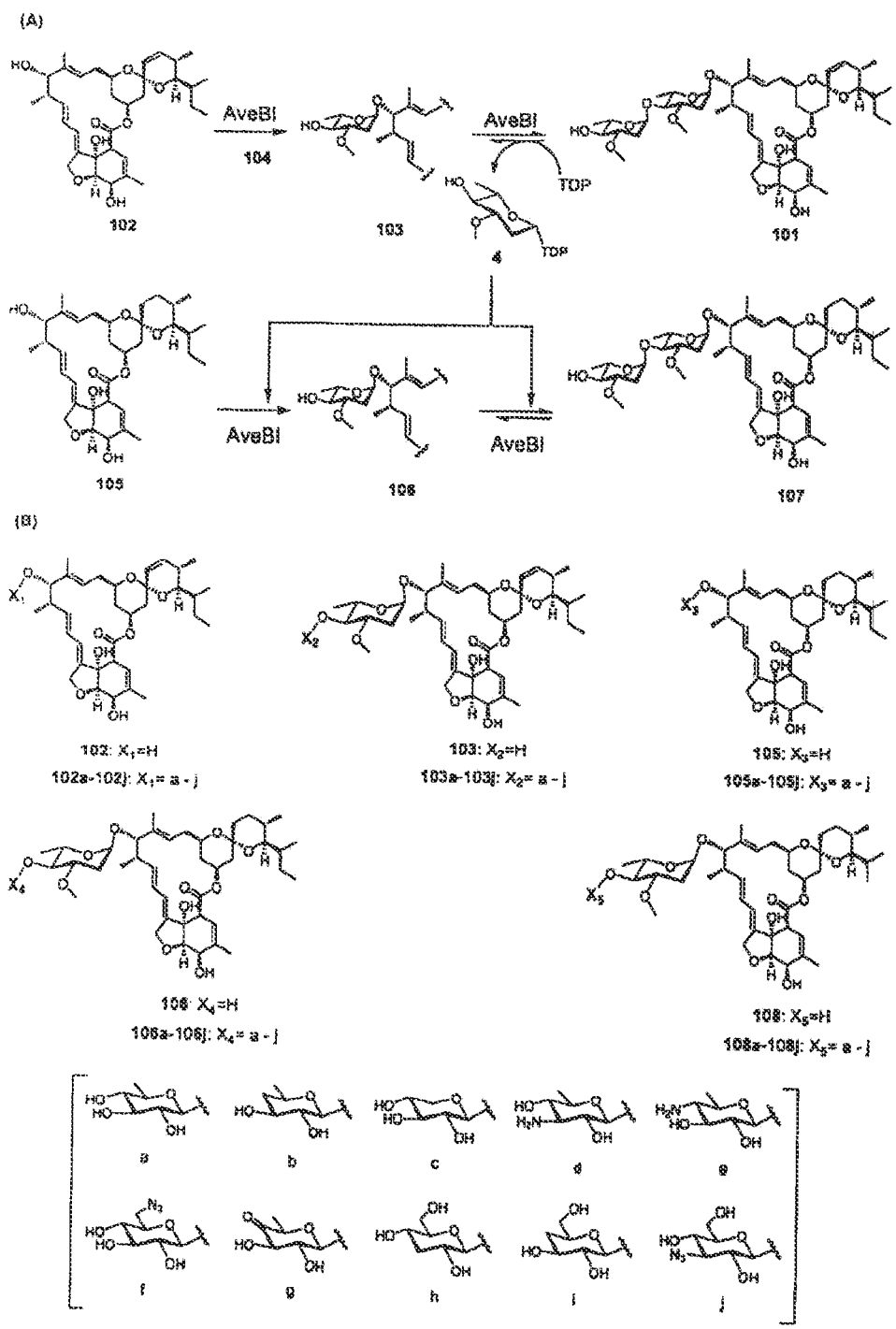

FIG. 21. (A) Tandem Sugar-Assembly by AveBI-catalyzed aglycon-exchange reaction. (B) A library of AVM analogs constructed via AveBI-catalyzed glycorandomization.

Figure 22:
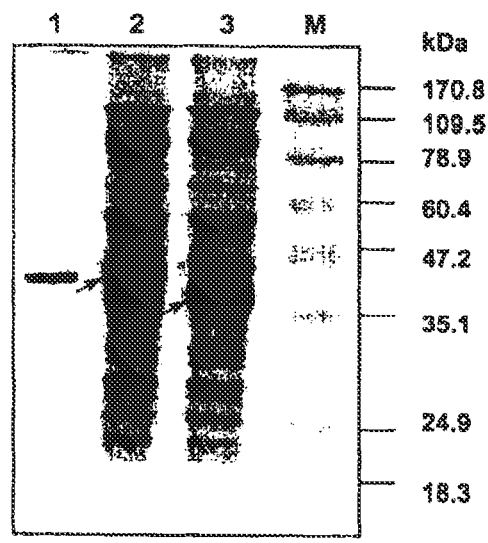

FIG. 22. SDS-PAGE analysis of the overexpression and purification of AveBI from Streptomyces lividans TK64. Lane 1, purified N-His6-tagged AveBI protein from S. lividans TK64 pCAM4.10; lane 2, soluble fractions from crude extracts of S. lividans TK64 pCAM4.10 expressing N-His6-tagged AveBI; 2, soluble fractions from crude extracts of S. lividans TK64 pCAM4.11 expressing native AveBI; lane M, protein molecular weight standard markers from Invitrogen (Carlsbad, Calif.). The expressed proteins are marked with arrows and molecular weights are indicated on the right column.

Figure 23:
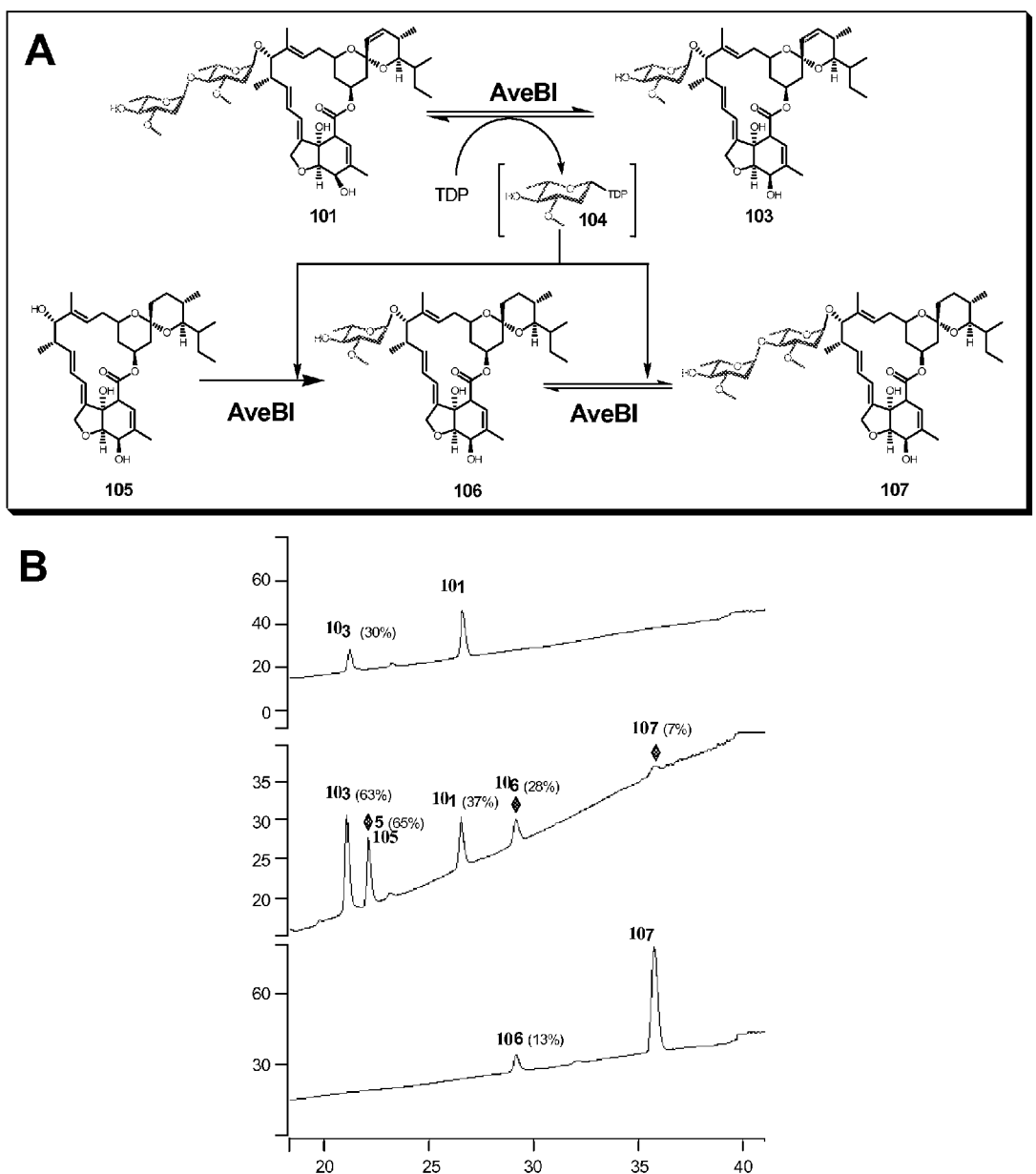

FIG. 23. AveBI-catalyzed aglycon exchange reactions. (A) Scheme for a AveBI-catalyzed aglycon exchange reaction. In this reaction, TDP-olendrose (104) was excised from 101 by AveBI and subsequently transferred to 105, to produce 106 and 107 in a stepwise, tandem manner. (B) RP-HPLC analysis of AveBI-catalyzed reverse and aglycon exchange reactions. (i) Co-incubation of 100 μM AVM B1a (101, M+Na 895.2) and 2 mM TDP in the presence of 12 μM of AveBI yielded 3 (30%, M+Na 751.0). (ii) Co-incubation of 100 μM AVM B1a (101), 100 μM 105 and 2 mM TDP in the presence of 12 μM of AveBI yielded 103 (63%) from 101, and subsequently, TDP-oleandrose produced in situ was transferred consecutively to 105 to yield 106 (28%) and 7 (7%). (iii) Co-incubation of 100 μM IVM (107) and 2 mM TDP in the presence of 12 μM AveBI yielded 106 (13%).

Figure 24:
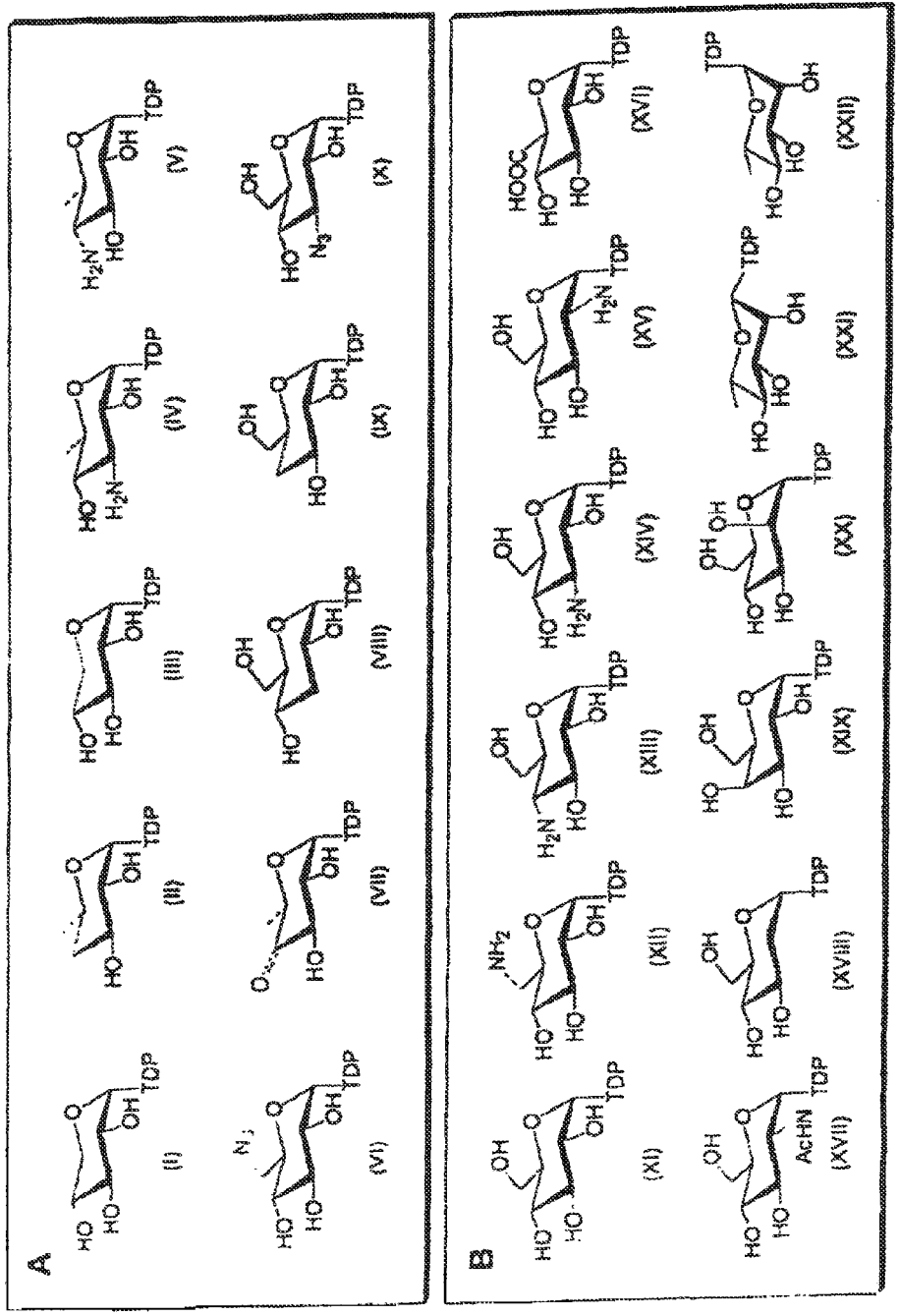

FIG. 24. Structures of TDP-sugars tested in this work. The sugar donors in (A) were AveBI substrates while those in (B) were not. Highlighted parts (red or blue) indicate the structural differences from TDP-α-D-glucose (XI).

Figure 25:
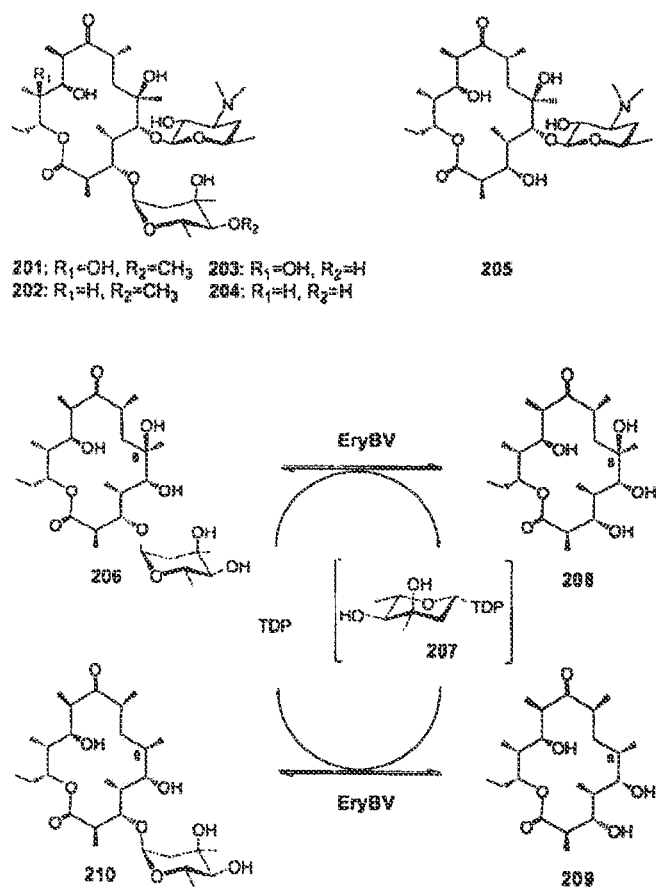

FIG. 25. The reversibility of EryBV-catalyzed reactions.

Figure 26:
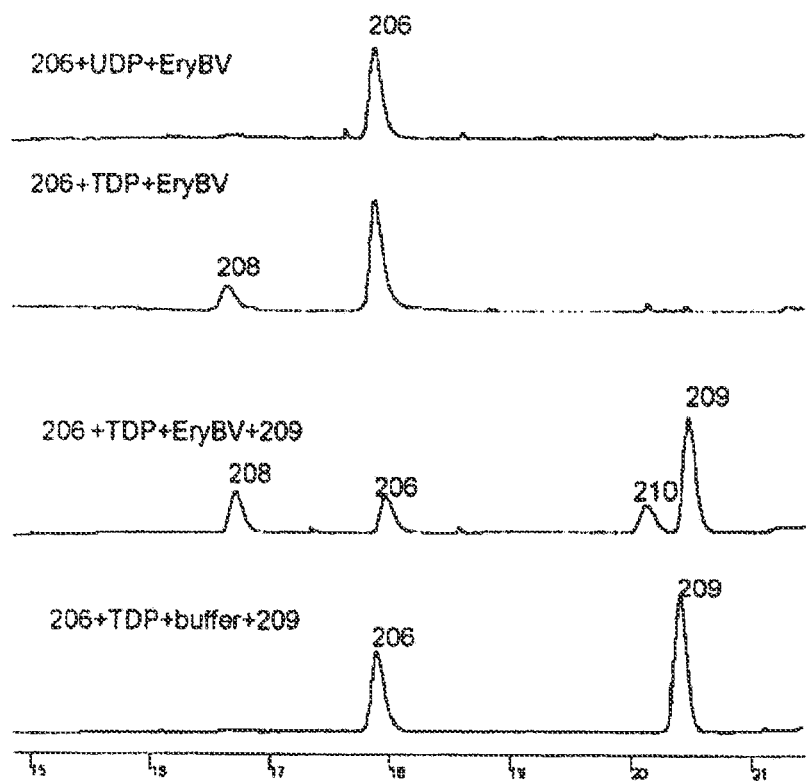

FIG. 26. RP-HPLC analysis of the exchange reaction of FIG. 25.

FIG. 27. (A) TDP mediated the AveBI reverse catalysis and (B). TDP mediated the EryBV reverse catalysis.

Figure 28:
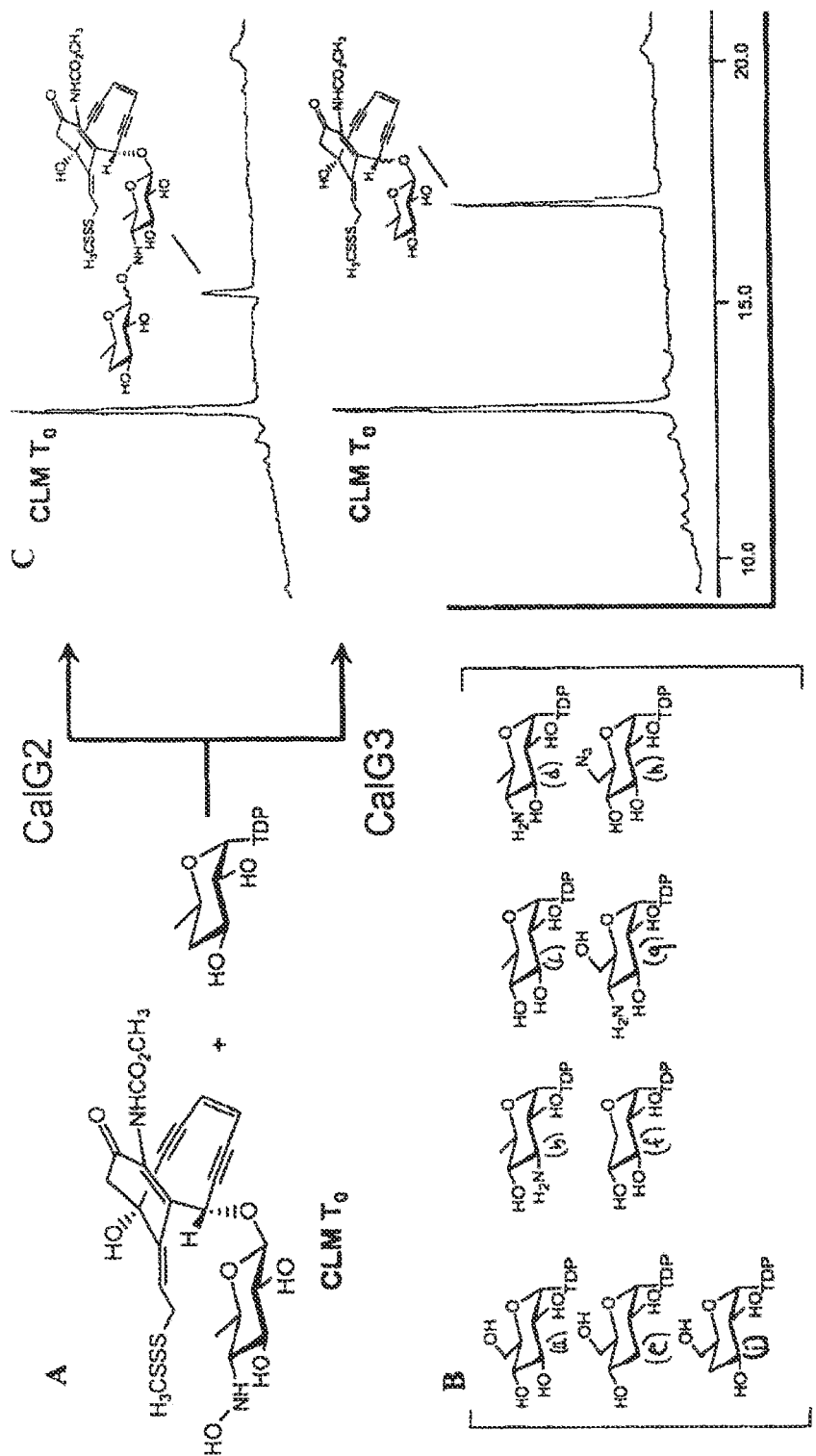

FIG. 28. CalG2 and CalG3 glycorandomization. (A) synthesis directed by CalG2 and CalG3; (B) The CalG2/G3-catalyzed transfer of unnatural sugars 28a-I; (C) RP-HPLC of CalG2/G3-catalyzed reactions.

Figure 29:
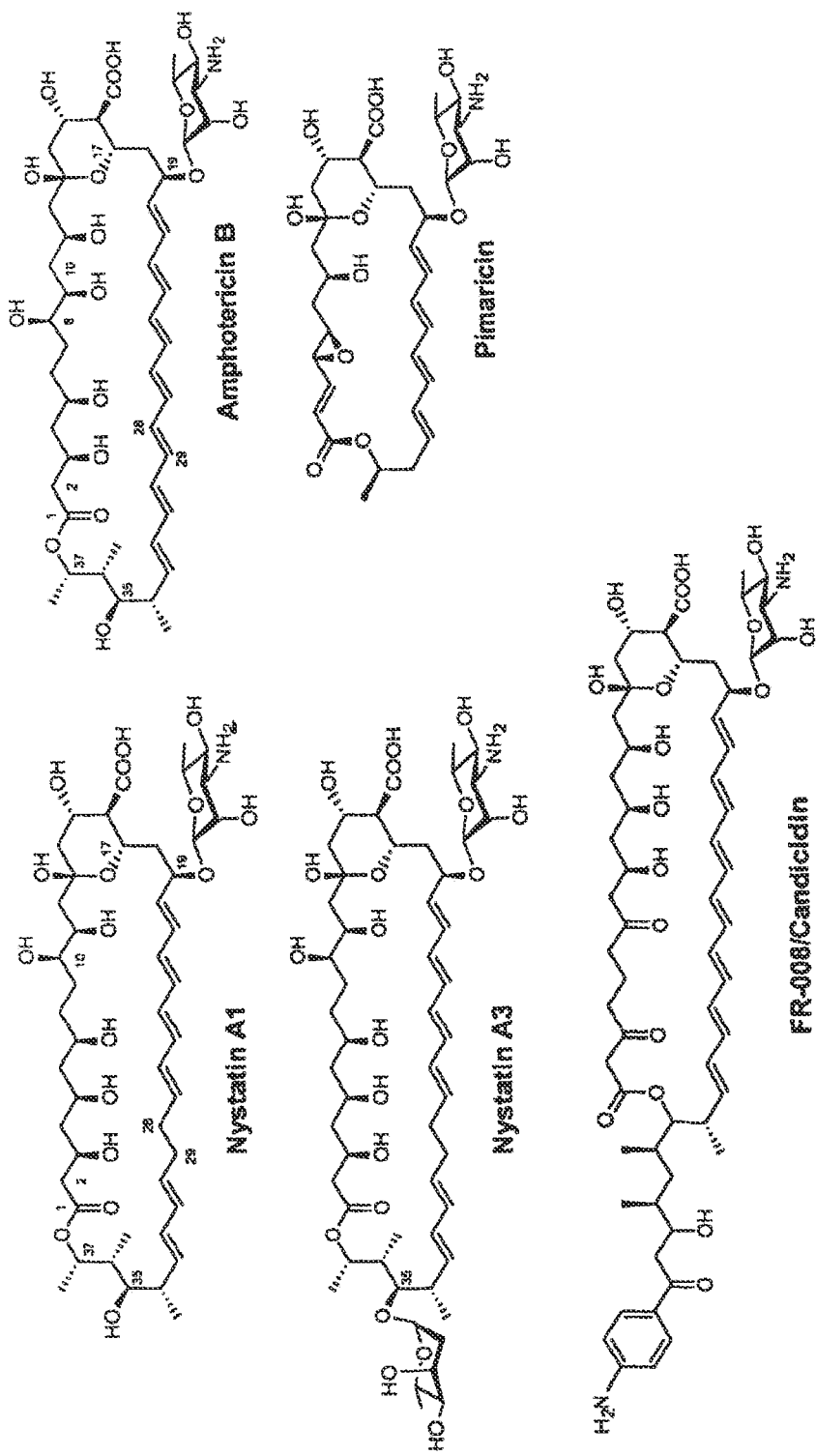

FIG. 29. Representative polyene antibiotics suitable for manipulating reversible glycosyltransferase reactions according to the present invention.

Figure 30A:
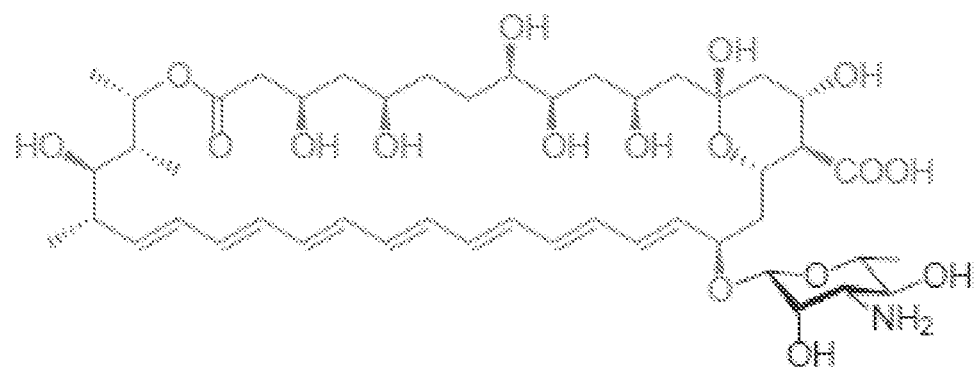
Figure 30B:
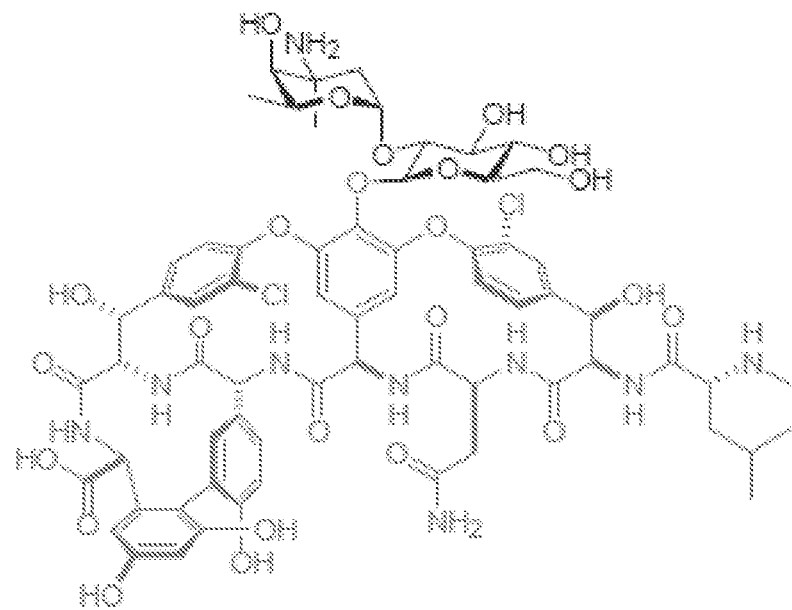
Figure 30C:
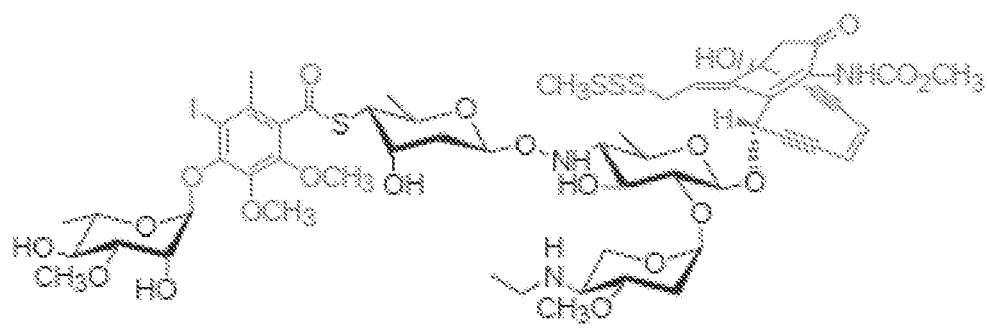
Figure 30D:
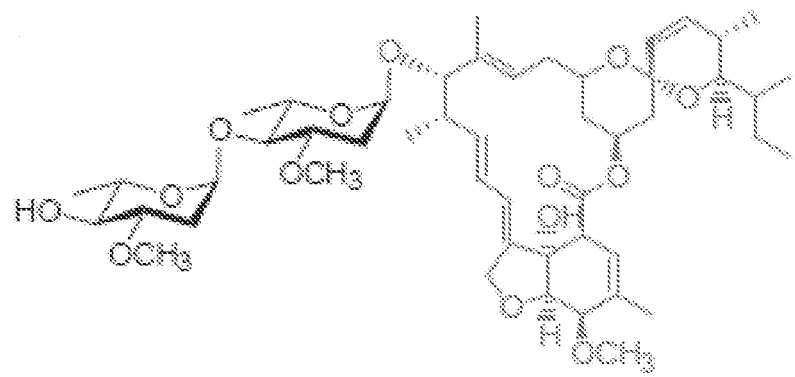
Figure 30E:
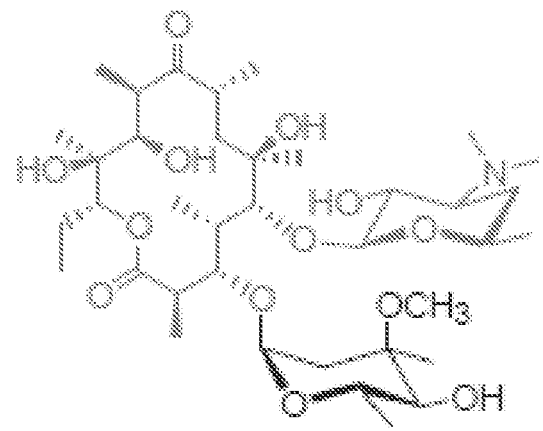

FIG. 30A-E. Representative biomolecules and reversible glycosyltransferases acting thereupon. Substrate specificity in indicated for each specific glycosyltransferase. FIG. 30A: NysD (5 aglycons, 8 NDP sugars), FIG. 30B: GtfE (31 NDP sugars), FIG. 30C: CalG1 (8 aglycons, 10 NDP sugars), FIG. 30D: AVrB (5 aglycons, 10 NDP sugars), and FIG. 30E: EryBV (5 aglycons, 10 NDP sugars).

DETAILED DESCRIPTION OF THE PREFERRED EMBODIMENTS

I. in General

This invention is not limited to the particular methodology, protocols, and reagents described, as these may vary. One of ordinary skill in the art may change the methodology, synthetic protocols and reagents as necessary. Further, the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

As used herein and in the appended claims, the singular forms "a", "an", and "the" include plural reference unless the context clearly dictates otherwise. Thus, for example, reference to "a sugar" includes a plurality of such sugars and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Although any methods and materials similar or equivalent to those described herein can be used in the practice or testing of the present invention, exemplary methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

II. Exemplary Embodiments of the Present Invention

The present invention relates to methods using glycosyltransferases and related novel compounds. Generally, the invention exploits the reversibility of glycosyltransferases to generate new sugars, unnatural biomolecules and numerous one-pot reactions for generation of new biomolecules having varied backbones such as enediynes, vancomycins, bleomycins, anthracyclines, macrolides, pluramycins, aureolic acids, indolocarbazoles, aminglycosides, glycopeptides, polyenes, coumarins, benzoisochromanequinones, calicheamicins, erythromycins, avermectins, ivermectins, angucyclines, cardiac glycosides, steroids or flavinoids.

In exemplary embodiments, the invention specifically relates to biosynthesis of anticancer (the enediyne calicheamicin, CLM), anthelmintic agents (the macrolide avermectin and ivermectin) and antibiotic (the glycopeptide vancomycin, VCM) natural product-based drugs developed by reversible, bidirectional glycosyltransferase catalyzed reactions.

One exemplary embodiment of the present invention provides a method of synthesizing an independent sugar moiety A, in-situ, from a biomolecule having a sugar moiety A. This method comprises the steps of: (a) incubating the biomolecule having the sugar moiety A with a nucleotide diphosphate in the presence of a glycosyltransferase wherein the sugar moiety A in the biomolecule is excised from the biomolecule, thereby generating the independent sugar moiety A and a biomolecule aglycon; and (b) isolating the independent sugar moiety A from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is preferably CalG1, CalG2, CalG3, CalG4, GtfD, GtfE, EryBV or AveBI. The biomolecule having the sugar moiety A is an enediyne, a vancomycin, a calicheamicin, an erythromycin, an avermectin or an ivermectin. Further, the sugar moiety is a NDP sugar and the sugar moiety A is a UDP sugar or a TDP sugar.

In one embodiment, the TDP sugar is selected from TDP-α-D-glucose, TDP-β-L-rham nose, TDP-O-methylrhamnose, TDP-6-azidoglucose, TDP-β-L-vancosamine, TDP-β-L-olendrose and TDP-β-L-mycarose. As described, this synthesis is reversible, whereby incubating the independent sugar moiety A and the biomolecule aglycon in the presence of a glycosyltransferase provides the biomolecule having the sugar moiety A.

Another exemplary embodiment of the present invention provides a method of exchanging a sugar moiety, in-situ, between (i) an independent sugar moiety B and (ii) a biomolecule having a sugar moiety A. This method comprises the steps of: (a) incubating the independent sugar moiety B with the biomolecule having sugar moiety A in the presence of a glycosyltransferase, wherein the sugar moiety A is excised from the biomolecule and the sugar moiety B is ligated in its place, thereby generating the independent sugar moiety A and a biomolecule having sugar B; and (b) isolating the independent sugar moiety A and the biomolecule having sugar moiety B from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is preferably CalG1, CalG2, CalG3, CalG4, GtfD, GtfE, EryBV or AveBI. Further, the biomolecule is an enediyne, a vancomycin, a calicheamicin, an erythromycin, an avermectin or an ivermectin. Further still, the sugar moiety A or B is independently selected from:

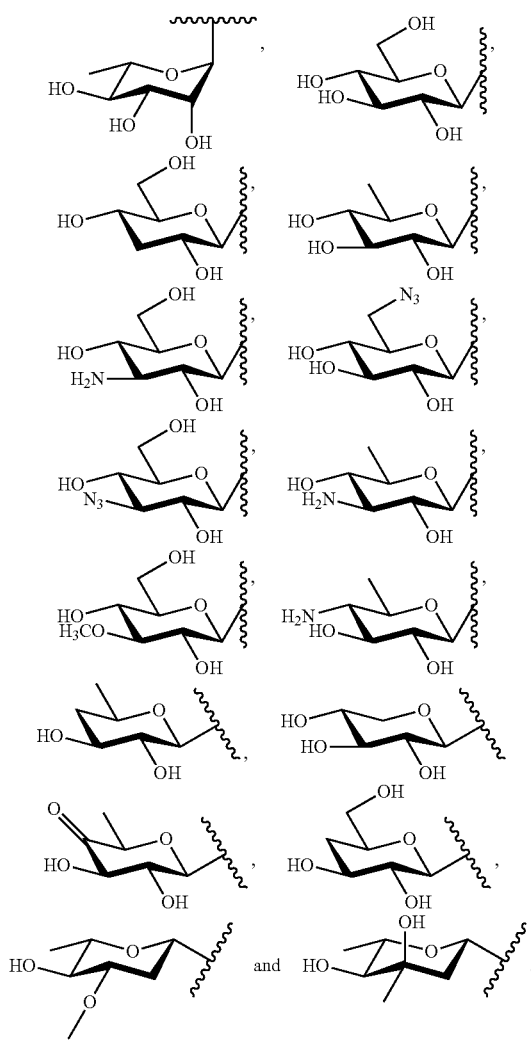

As described here, the sugar exchange is reversible, whereby incubating the independent sugar moiety A and the biomolecule having sugar moiety B in the presence of a glycosyltransferase results in the independent sugar moiety B and the biomolecule having a sugar moiety A.

Yet another exemplary embodiment of the present invention provides a method of generating a biomolecule A having a sugar moiety A from a biomolecule B having the sugar moiety A, in situ. This method comprises the steps of: (a) incubating the biomolecule A, biomolecule B having the sugar moiety A and a nucleotide diphosphate in the presence of a glycosyltransferase wherein (i) the sugar moiety A of the biomolecule B is excised from the biomolecule B, thereby generating an independent sugar moiety A and a biomolecule aglycon B; and (ii) the independent sugar moiety A and the biomolecule A are ligated, thereby generating the biomolecule A having the sugar moiety A; and (b) isolating the biomolecule A having sugar moiety A from step (a), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method the glycosyltransferase is preferably CalG1, CalG2, CalG3, CalG4, GtfD, GtfE, EryBV or AveBI. Also, the biomolecule A or biomolecule B is an enediyne, a vancomycin, a calicheamicin, an erythromycin, an avermectin, an ivermectin or combinations thereof.

As described here, the method of generating biomolecule A having the sugar moiety A from the biomolecule B having the sugar moiety A is reversible, such that incubating the biomolecule A having the sugar moiety A and the biomolecule aglycon B in the presence of a glycosyltransferase results in the biomolecule B having the sugar moiety A.

Another exemplary embodiment of the present invention provides a method of generating a biomolecule A having a sugar moiety A and a biomolecule B having a sugar moiety B from a biomolecule B having the sugar moiety A and a biomolecule A having the sugar moiety B. This method comprises the steps of: (a) incubating the biomolecule A having the sugar moiety B, biomolecule B having the sugar moiety A and a nucleotide diphosphate in the presence of a glycosyltransferase wherein (i) the sugar moiety A of the biomolecule B is excised from the biomolecule B, thereby generating an independent sugar moiety A and a biomolecule aglycon B; (ii) the sugar moiety B of the biomolecule A is excised from the biomolecule A, thereby generating an independent sugar moiety B and a biomolecule aglycon A; and (iii) the independent sugar moiety A and the biomolecule A are ligated, the independent sugar moiety B and the biomolecule B are ligated, thereby generating the biomolecule A having the sugar moiety A and biomolecule B having the sugar moiety B; and (b) isolating the biomolecule A having the sugar moiety A and the biomolecule B having from the sugar moiety B from step (a)(iii), wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the glycosyltransferase is CalG1, CalG2, CalG3, CalG4, GtfD, GtfE, EryBV or AveBI. The biomolecule A or biomolecule B is an enediyne, a vancomycin, a calicheamicin, an erythromycin, an avermectin, an ivermectin or combinations thereof.

As described this method of generating the biomolecule A having the sugar moiety A and the biomolecule B having the sugar moiety B is reversible, such that incubating the biomolecule A having the sugar moiety A and the biomolecule B having the sugar moiety B in the presence of a glycosyltransferase results in the biomolecule B having the sugar moiety A and the biomolecule A having the sugar moiety B.

In yet another exemplary embodiment, the present invention provides a method of generating a library of isolated glycosylated biomolecules comprising transferring a sugar moiety from a first biomolecule backbone to a second biomolecule backbone in the presence of a glycosyltransferase wherein the sugar moiety is transferred from the first biomolecule backbone to the second biomolecule backbone thereby generating a non-naturally occurring glycosylated biomolecule, wherein the biomolecule backbone is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an angucycline, a cardiac glycoside, a steroid or a flavinoid.

In this method, the first and the second glycosylated biomolecule backbones are independently selected from: an enediyne, a vancomycin, a calicheamicin, an avermectin, an ivermectin, an erythromycin and combinations thereof. The sugar moiety is selected from:

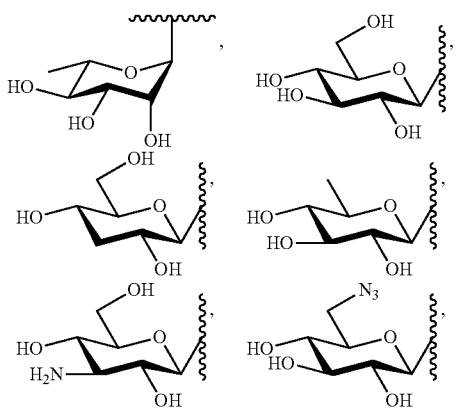

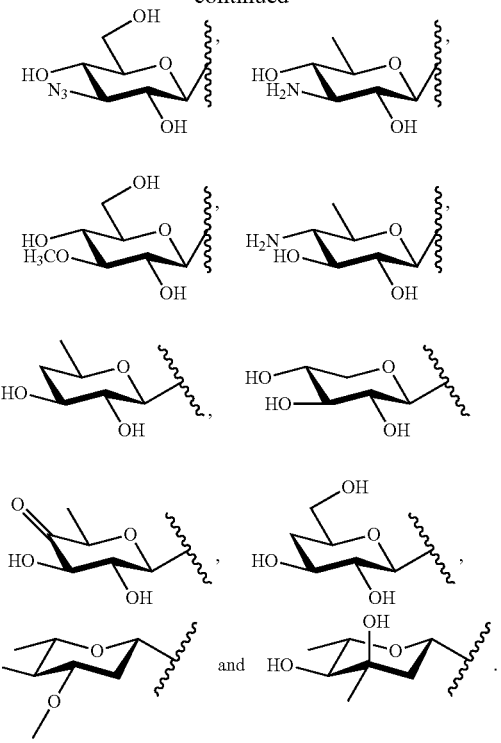

Another embodiment of the present invention provides a glycoside analog of Formula I through XIV having a non-native sugar moiety, (a) wherein the glycoside analog is selected from:

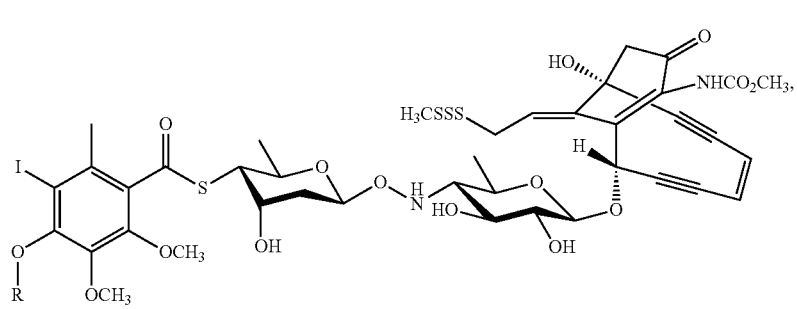

I

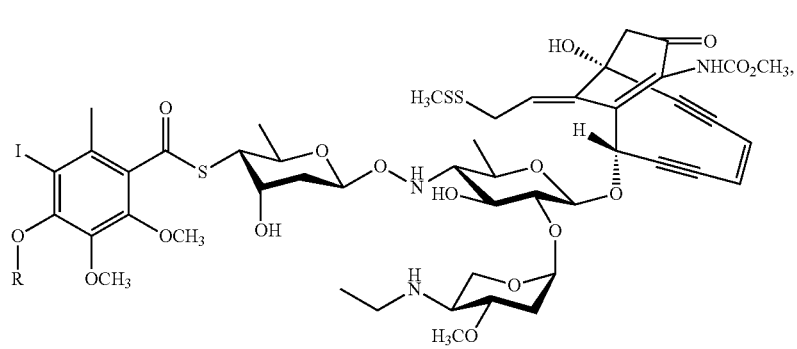

II

-continued
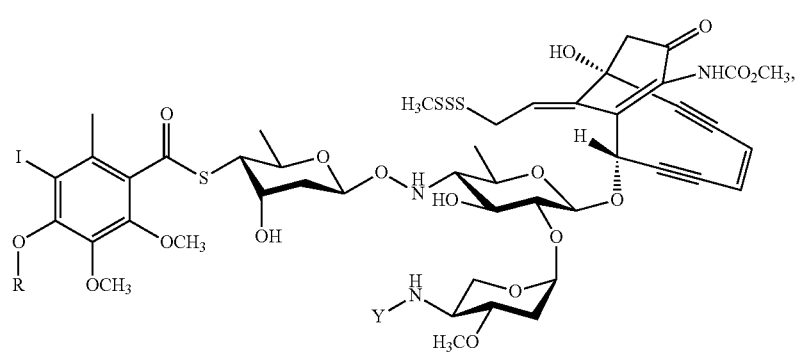
III
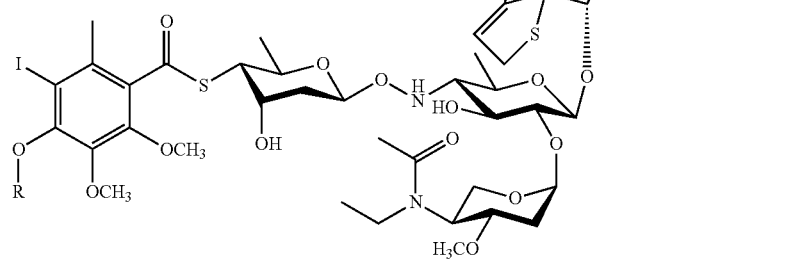
IV
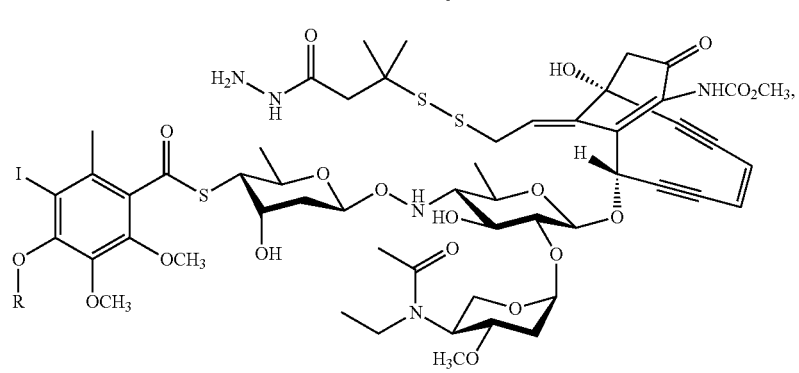
V
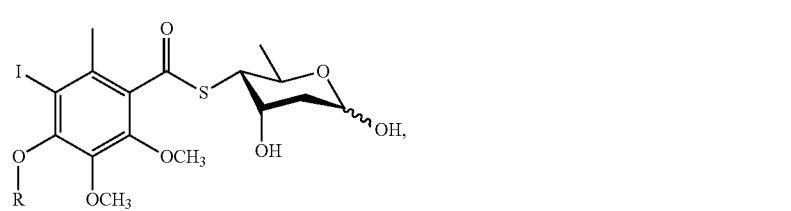
VI
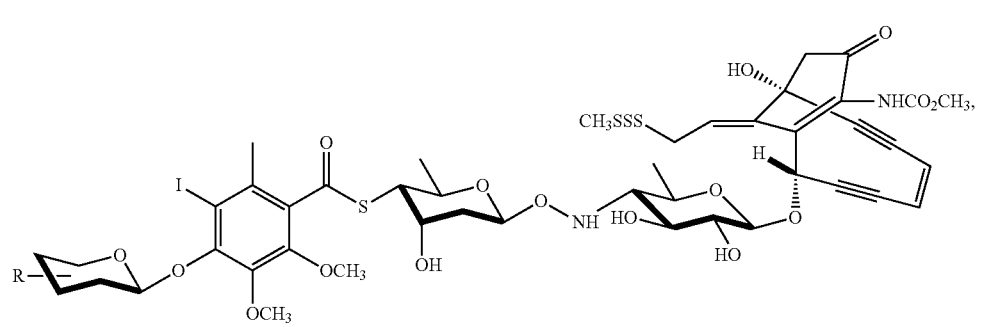
VII -continued
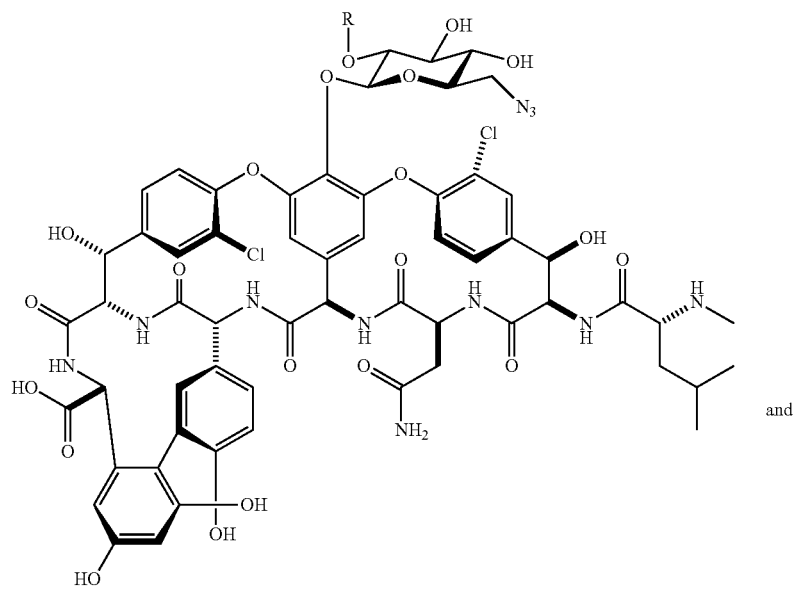
VIII
and
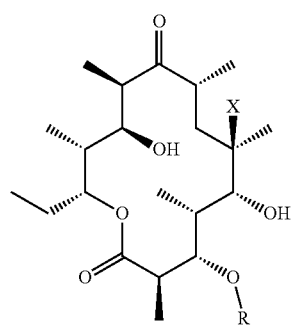
IX
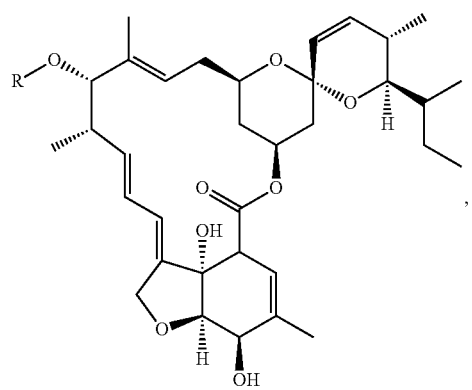
X XI
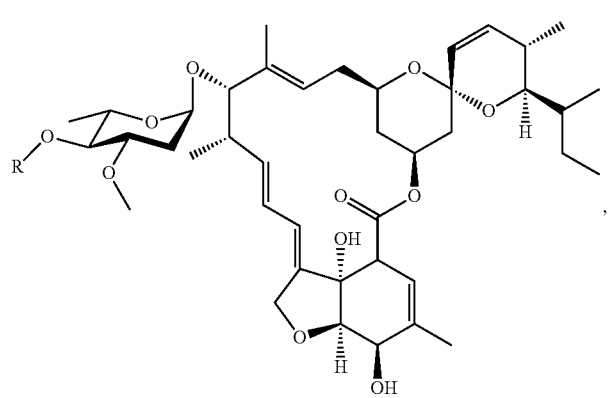,
XII
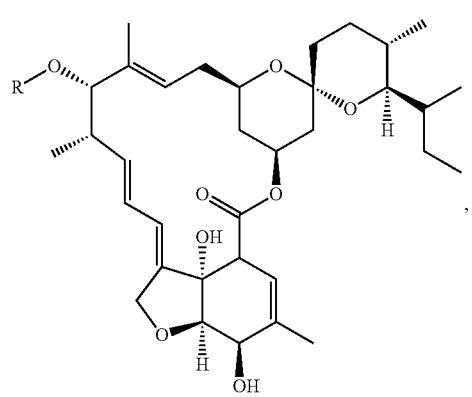,
XIII
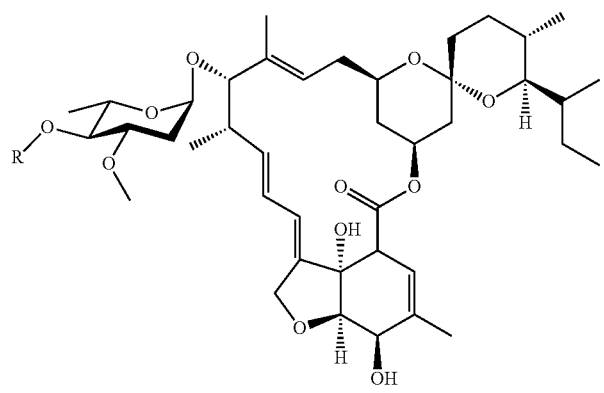 and
XIV
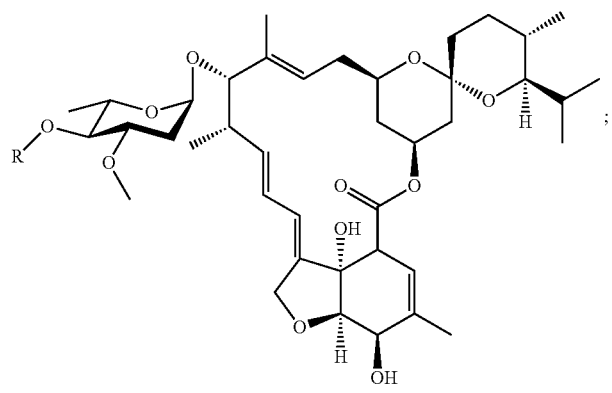;
(b) optionally wherein the glycoside analog of Formula II, III, IV or V further includes a 3'-O-methylrhamnose moiety; (c) wherein Y is independently selected from $CH(CH_3)_2$, $CH_2(CH_3)_2$, $CH_2CH_3$ or $CH_3$; (d) wherein X is independently selected from H or OH; and (e) wherein, R is independently selected from a sugar moiety selected from:

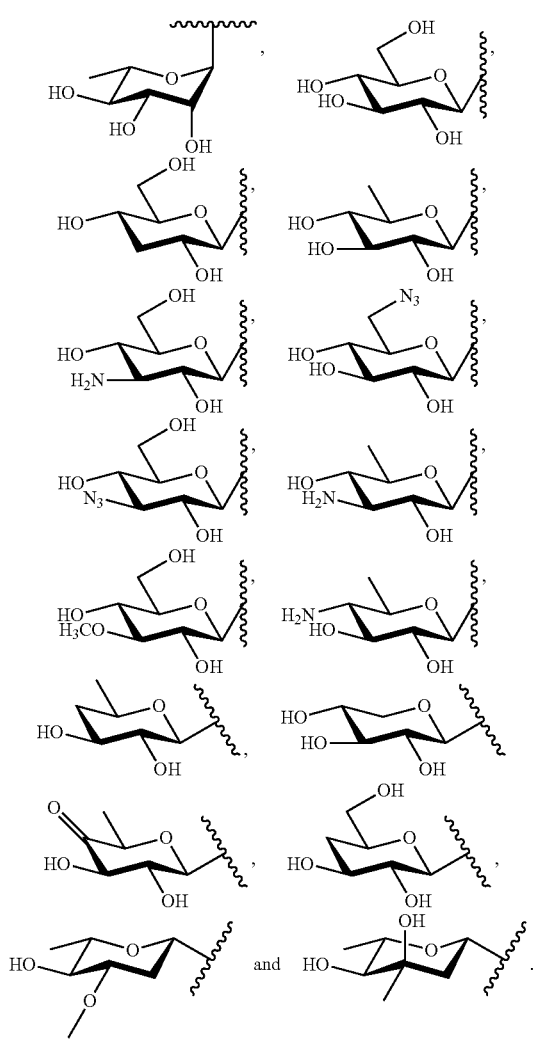

Glycosyltransferases (GTs), an essential class of ubiquitous enzymes, are generally perceived as unidirectional catalysts. However, the present invention teaches that four GTs from two distinct natural product biosynthetic pathways—calicheamicin and vancomycin—catalyze readily reversible reactions, allowing sugars and aglycons to be exchanged with ease. As proof of the broader applicability of these new reactions, more than seventy differentially glycosylated calicheamicin and vancomycin variants are reported. Thus, the reversibility of GT-catalyzed reactions may be general and useful for exotic nucleotide sugar generation, establishing in vitro GT activity in complex systems, and enhancing natural product diversity.

Provided below are certain exemplary examples of the preferred embodiment of the invention. These examples are provided for illustrative purposes only and should not be deemed to limit the scope of the invention.

EXAMPLE I

Exploiting the Reversibility of Natural Product Glycosyltransferase-Catalyzed Reactions Specifically, the GTs tested (CLM CalG1/G2/G3/G4 and VCM GtfD/E) were found to catalyze three new reactions—i) the synthesis of exotic NDP-sugars from glycosylated natural products, ii) the exchange of native natural product glycosides with exogenous carbohydrates supplied as NDP-sugars, and iii) the transfer of a sugar from one natural product backbone to a distinct natural product scaffold. As proof of the broader applicability of these new reactions, the GT-catalyzed production of more than seventy differentially glycosylated CLM variants and a VCM analog bearing a handle for chemical diversification and a rare amino sugar are also reported.

Figure 5:
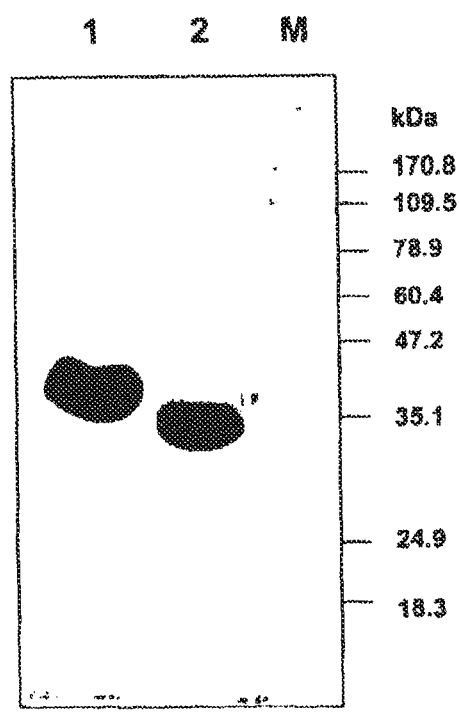
FIG. 5. SDS-PAGE analysis of the purified CLM GTs. Lane 1, CalG4; lane 2, CalG1; lane M, standard protein molecular weight markers. CalG1 and CalG4 were overproduced in *E. coli* BL21 (DE3) and purified as N-(His)$_{10}$-tagged proteins as described in the Materials and Methods, with overall yields of 10-15 mg per liter of culture.

The calG1 gene was amplified from the genomic DNA of the CLM-producer, *Micromonospora echinospora*, overexpressed in *E. coli*, and the recombinant CalG1 was purified to homogeneity (FIG. 5)[7]. Analysis of the CLM $\gamma_1^I$ biosynthetic gene cluster revealed four putative GT-encoded genes, calG1, calG2, calG3 and calG4, implicating a distinct GT for each sugar attachment[7]. The calG1-G4 genes were expressed and purified to near homogeneity (FIG. 5), with overall yields of 10-15 mg per liter of culture Incubation of the aglycon (1) with the surrogate substrate TDP-β-L-rhamnose (FIG. 1A) in the presence of CalG1 led to the formation of a new product (FIG. 1D, panel i), characterized as product (2a) by LC-MS.

Consistent with CalG1 as the requisite rhamnosyltransferase in CLM biosynthesis, no product was observed when CalG1 was replaced with other GTs in this assay. Also, substitution of TDP-α-L-rhamnose for TDP-β-L-rhamnose in the CalG1 assay yielded no product, consistent with CalG1 functioning as a stereospecific inverting GT.

Figure 1D:
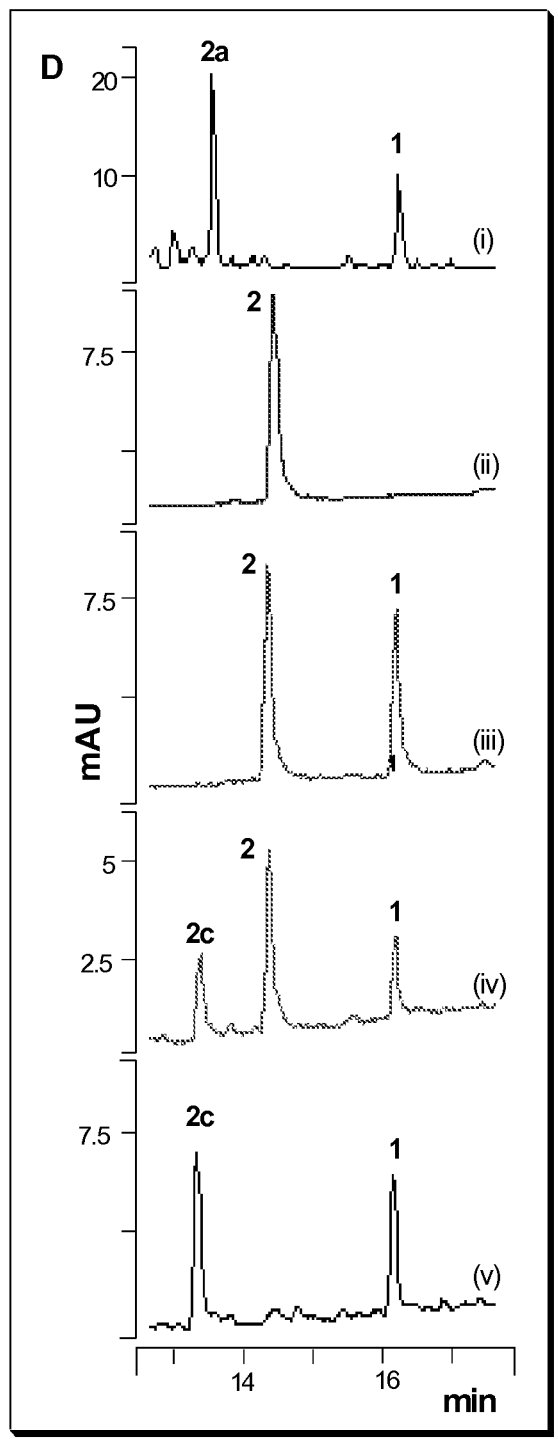
FIG. 1. In vitro CalG1-catalyzed reactions. (A) The CalG1-catalyzed transfer of unnatural sugars to the acceptor (1). The TDP-sugars corresponding to glycosides 2c-2j were enzymatically generated as previously described, TDP-β-L-rhamnose (for 2a) was prepared via chemical synthesis and TDP-α-D-glucose (for 2b) was obtained from a commercial source. (B) CalG1-catalyzed reverse glycosyltransfer and sugar exchange reactions. In the first step, the terminal 3'-O-methylrhamnose unit of 2 (CLM $\alpha_3^1$, one of ten CLMs produced by M. echinospora) was transferred to TDP, yielding (1) and TDP-3-O-methyl-β-L-rhamose (3, see also FIGS. 1C and 1D). The subsequent sugar exchange involved the transfer of unnatural sugars (from exogenous NDP-sugars) to (1) to give compounds 2a-2j. (C) Anion exchange HPLC of CalG1-catalyzed 3 formation: i) control with 50 μN 2 and 100 μM TDP (see also FIG. 1D, panel ii); ii) 50 μM 2, 100 μM TDP and CalG1 (see also FIG. 1D, panel iii). The new peak at 13 min. was isolated and identified as 3 by MS/MS (FIG. 9). (D) RP-HPLC of CalG1-catalyzed reactions: i) 50 μM (1), 300 μM TDP-β-L-rhamnose and CalG1; if) reverse glycosyltransfer control with 50 μM 2 and 100 μM TDP (see also FIG. 1C, panel i); iii) 50 μM 2, 100 μM TDP and CalG1 (see also FIG. 1C, panel ii); iv) 50 μM 2, 300 μM TDP-3-deoxy-α-D-glucose and CalG1 (sugar exchange); v) 50 μM (1), 300 μM TDP-3-deoxy-α-D-glucose and CalG1. All CalG1 assays were performed in a total volume of 100 in Tris-HCl buffer (10 mM, pH 7.5) containing 1 mM of $MgCl_2$ and 10 μM CalG1 with incubation at 30° C. for 3-12 h. HPLC parameters are described in the following sections FIG. 2. Strategy for the construction of a CLM library by CalG1-catalyzed sugar exchange. The general strategy involved the CalG1-mediated exchange of the natural 3'-O-methylrhamnose (highlighted in red) in CLMs $\alpha_3^1$ (2), $\beta_1^1$ (4), $\gamma_1^1$ (5), $\delta_1^1$ (6), DMH Nac γ (7), $\gamma_2^1$ (8), and Nac ε (9) with sugars supplied via the 10 established CalG1 NDP-sugar substrates (FIG. 6A). In addition, fragment III (10) was also converted to the rhamnoside and glucoside to cumulatively provide 72 diversely functionalized CLM derivatives. For this study, CLMs 2 and 4-6 are natural metabolites while 7-10 are chemically modified CLM derivatives. A typical CalG1 sugar exchange reaction contained 50 μN aglycon (2, 4-10), 300 μM NDP-sugar and 10 μM CalG1 in a total volume of 100 μL in Tris-HCl buffer (10 mM, pH 7.5) containing 1 mM of $MgCl_2$ at 30° C. for 3 h. HPLC parameters are provided in the following sections; chromatograms for representative reactions are provided in FIG. 10. The structures of all library members are illustrated in FIG. 11 and conversion rates are provided in FIGS. 12 and 14. It should also be noted that CalG4 can excise the aminopentosyl units (highlighted in blue) from 4-6 and 8 for sugar/aglycon exchange.
Figure 2:
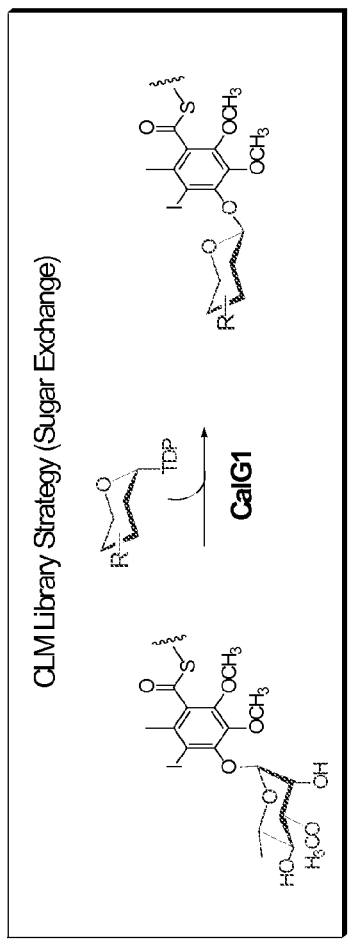
Figure 2:
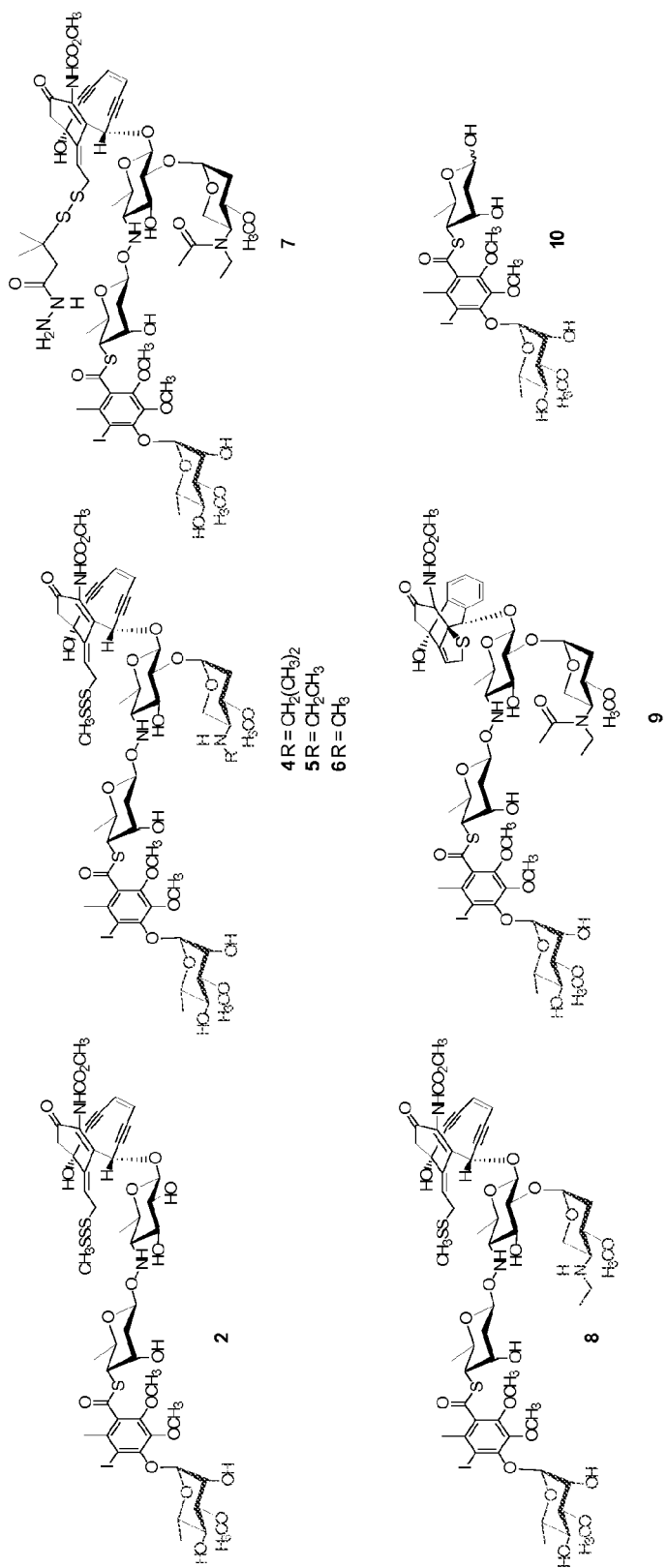
Figure 6:
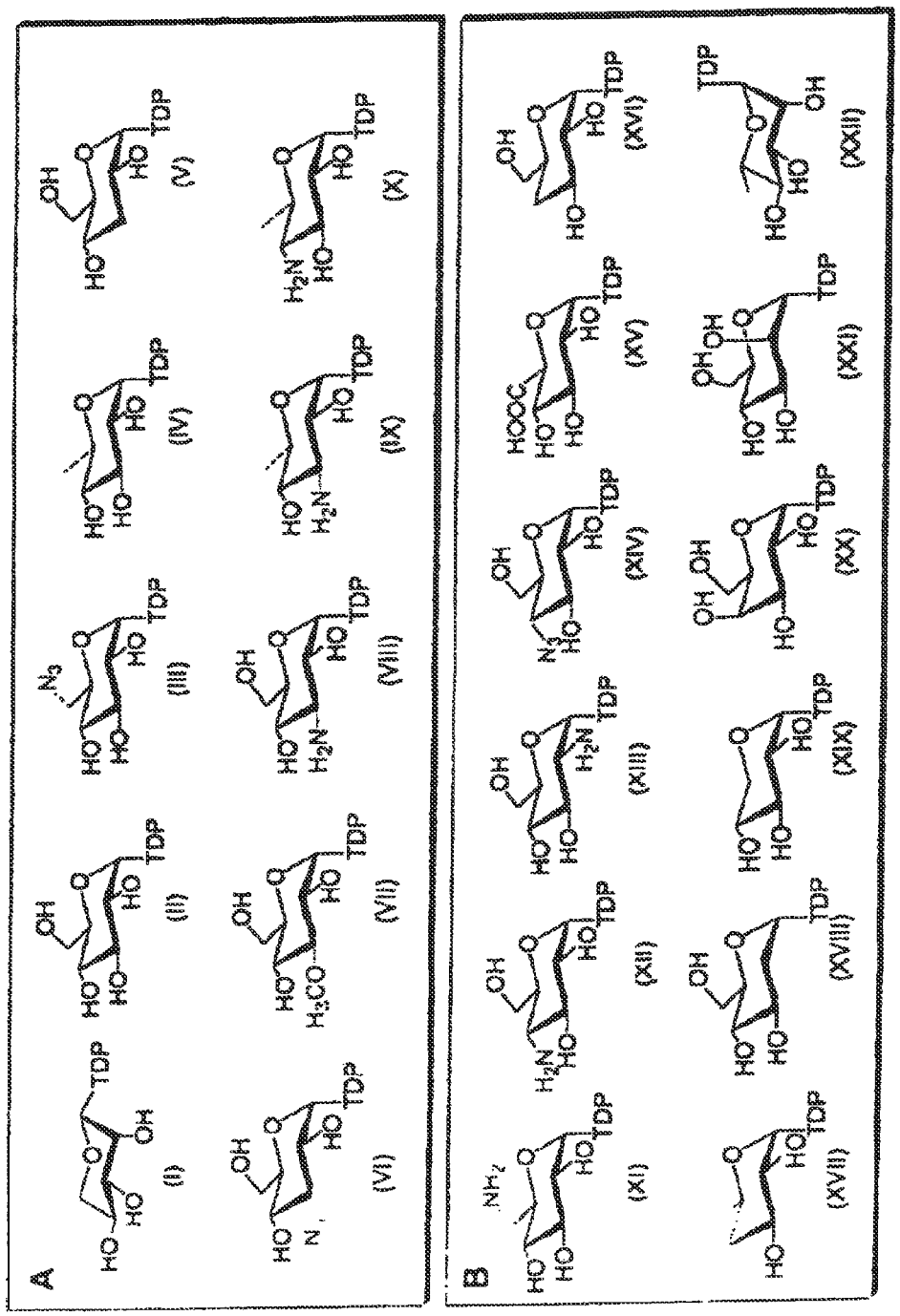
FIG. 6. Structures of TDP-sugars tested in this work. The sugar donors in (A) were CalG1 substrates while those in (B) were not. Highlighted parts (red or blue) indicate the structural differences from TDP-α-D-glucose (II). CalG1 shows the most relaxed specificity to sugar C3-substitution (e.g. V-IX). CalG1 can tolerate neutral modifications at C'6 (I, III, IV, IX, X) but not charged substitutions (XI and XV). With one exception (X), modifications at C4 (XII, XIV, XVI, XVII) and C2 (XIII, XVIII and XXI) were not tolerated by CalG1. The generation of TDP-sugars (III-XXI) was described in "Materials and Methods", according to literature procedures (37-33).

A diverse library of twenty-two TDP-sugars (Materials and Methods) was used to probe the NDP-sugar specificity of CalG1 (FIG. 1A and FIG. 6). Nine additional TDP-sugar substrates were converted to their corresponding CLM glycosides 2b-2j (FIG. 1A) in percent conversions of 27%-62% (FIG. 7). LC-MS/MS of products 2b and 2d revealed fragmentation patterns consistent with attachment of the sugar to the aromatic ring of the substrate and were highly consistent with the fragmentation of naturally occurring standard CLMs $\alpha_3^I$ (2) and $\gamma_1^I$ (5) (FIGS. 2 and 8). Cumulatively, these studies designated CalG1 as the CLM rhamnosyltransferase, capable of flexibility toward diverse TDP-D- and TDP-L-sugar donors.

Figure 3:
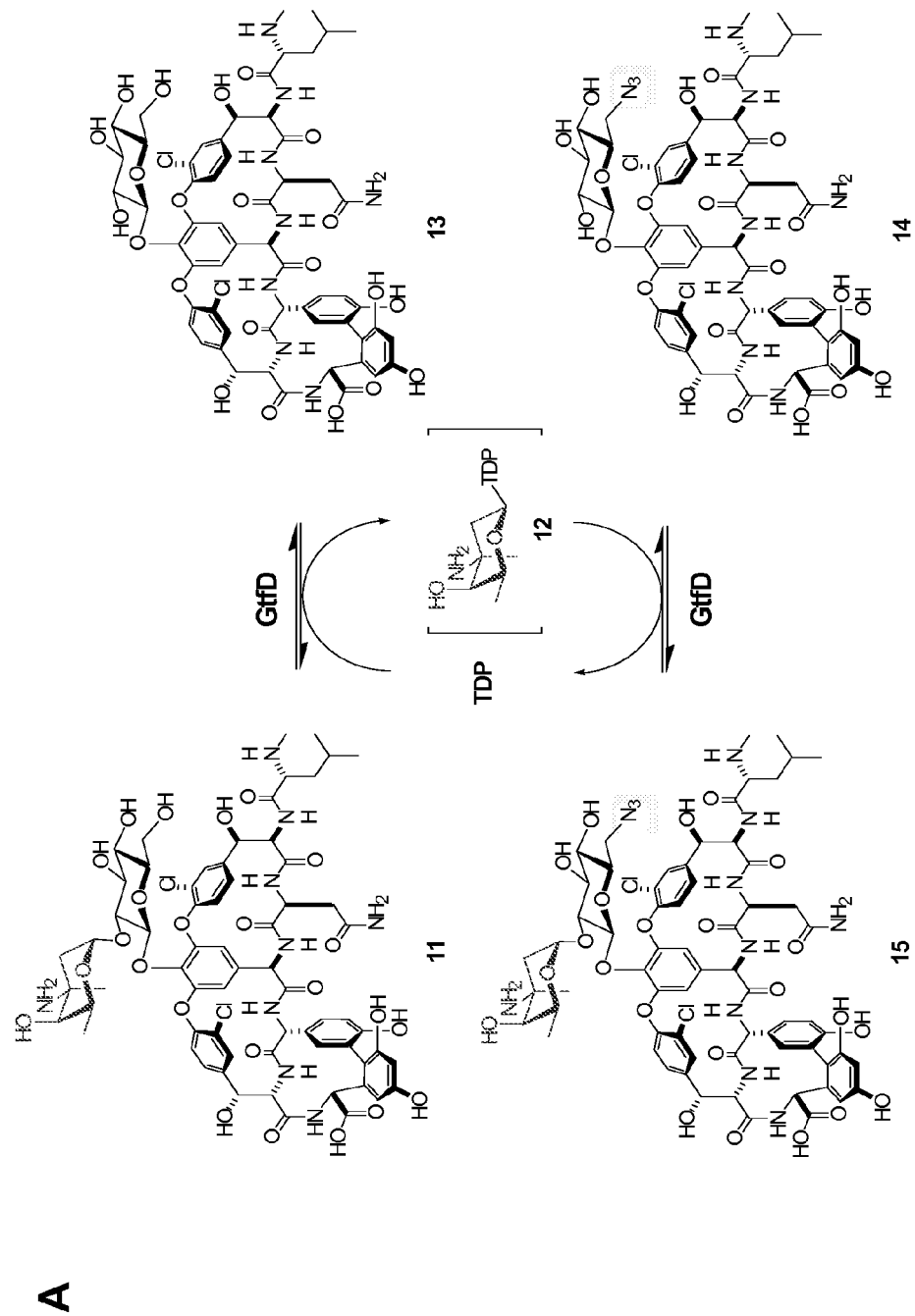
FIG. 3. VCM GT-catalyzed reverse and aglycon exchange reactions. (A) GtfD-catalyzed aglycon exchange reaction to provide 2'-vancosaminyl-6'-azidoglucosyl-VCM (15). The TDP-β-L-vancosamine (12) for this reaction was generated in situ by a GtfD-catalyzed reverse glycosyltransfer and subsequently transferred to the unnatural 6-azidoglucose-containing derivative 14 to give compound 15 in 27% conversion (FIG. 17). The reaction was performed in a total volume of 100 μL in Tricine-NaOH buffer (75 mM Tricine, pH 9.0, 2.5 mM $MgCl_2$, 2.5 mM TCEP and 1 mg/mL BSA) containing 100 μM 11, 100 μM 14, 1 mM TDP and 12 μM GtfD. (B) A two component GT-catalyzed aglycon exchange reaction using two diverse natural product scaffolds. In this one-pot reaction, TDP-6-azidoglucose (16, provided by GtfE-catalyzed reverse glycosyltransfer from sugar donor 14) served as the NDP-sugar donor for the CalG1-mediated attachment of 6-azidoglucose to CLM 1, yielding 2f in 48% conversion (FIG. 18). A typical reaction contained 100 μN 14, 50 μM 1, 100 μM TDP, 10 μM GtfE and 10 μM CalG1 in a total volume of 100 μL in Tris-HCl buffer (10 mM, pH 7.5) containing 1 mM of $MgCl_2$ at 30° C. for 3 h. For FIG. 3, detailed assay and HPLC parameters and chromatograms are provided in the following sections.
Figure 3:
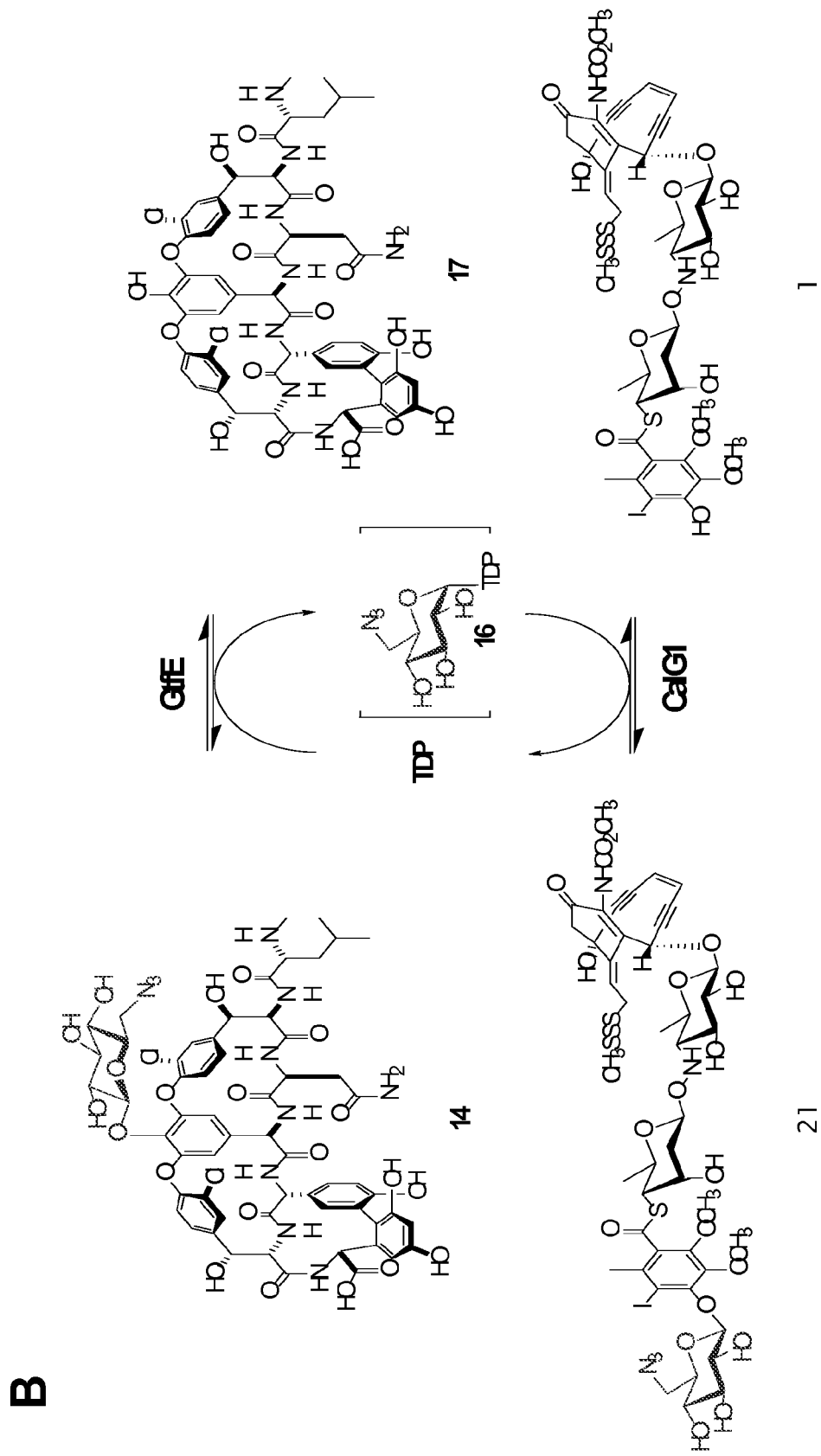
Figure 9:
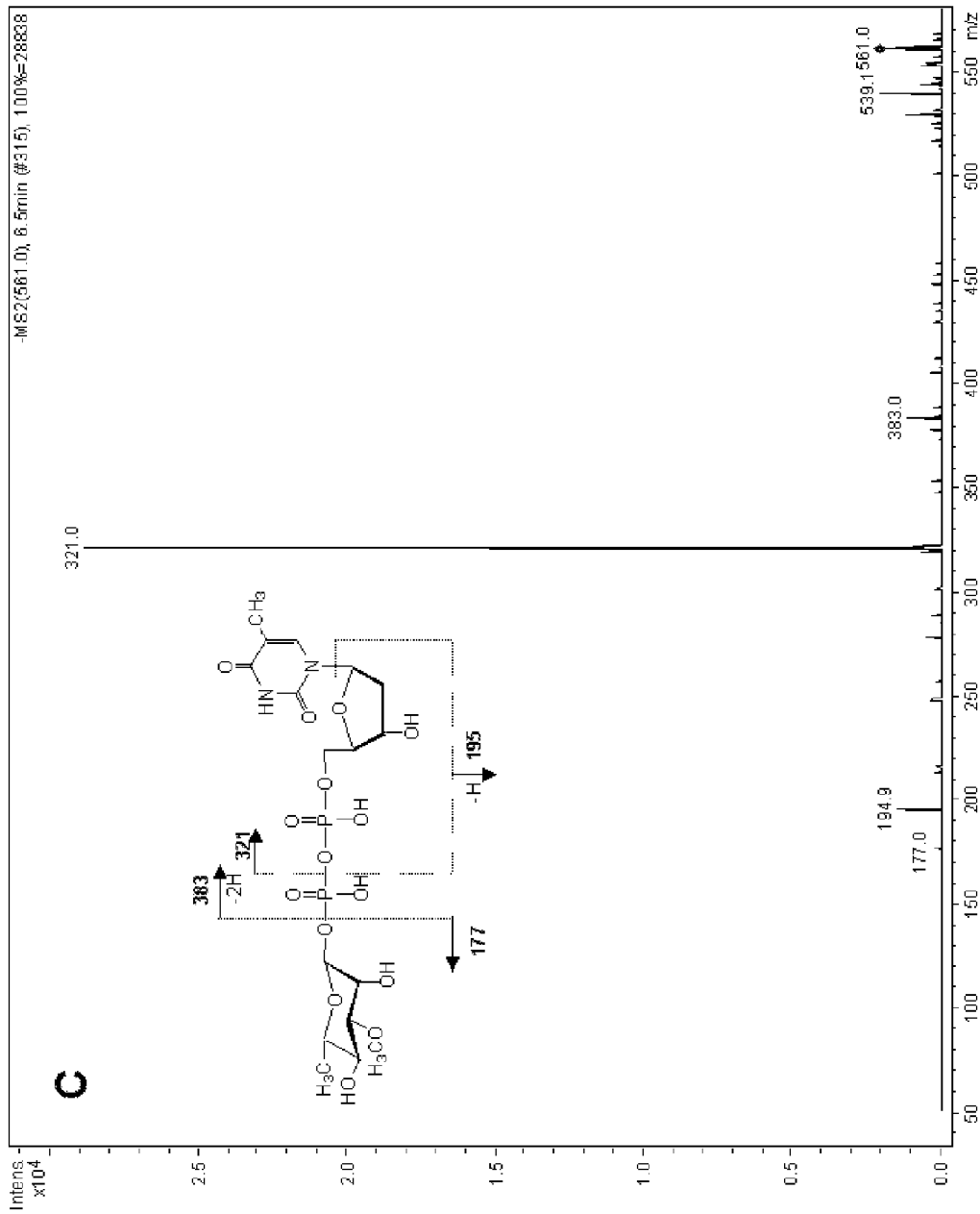
FIG. 9. TDP-dependent CalG1-catalyzed reverse glycosyltransfer. (A) RP-HPLC analysis of the TDP-dependence of CalG1-catalyzed reaction reversibility. TDP mediated the conversion of 2 to 1 (panels iii and iv), with higher [TDP] (2 mM) resulting in a higher conversion (70%) compared to reactions containing lower [TDP] (0.2 mM, 40%). Other NDPs failed to promote the reverse reaction (e.g. UDP, panel ii). No reaction was observed in the absence of CalG1 (panel i) or in the presence of a different CLM GT (e.g. CalG4, panel v). These control reactions demonstrated that the reverse catalysis was specific for TDP and CalG1. (B) Anion exchange HPLC analysis of TDP-sugar formation required for CalG1-catalyzed reverse glycosyltransfer. TDP-3-O-methyl-β-L-rhamnose (3) was observed in CalG1-catalyzed reverse reactions with CLM derivatives 4 (panel vii), 5 (panel viii) and 6 (panel ix). 3 was separable from TDP (panel vi, standard) and was absent in a control reaction performed in the absence of CalG1 (panel x). Reactions were carried out by co-incubating 50 µM CLMs (2, 4-6) and 100 µM TDP in the presence or absence of 10 µM CalG1. (C) Characterization of TDP-3-O-methyl-β-L-rhamnose (3) by MS/MS spectrometry. 3: calc. 562.1, [M–H] 561.0. The MS/MS fragmentation pattern of 3 exhibits several peaks indicative of a TDP-sugar and is illustrated as an inset.
Figure 11:
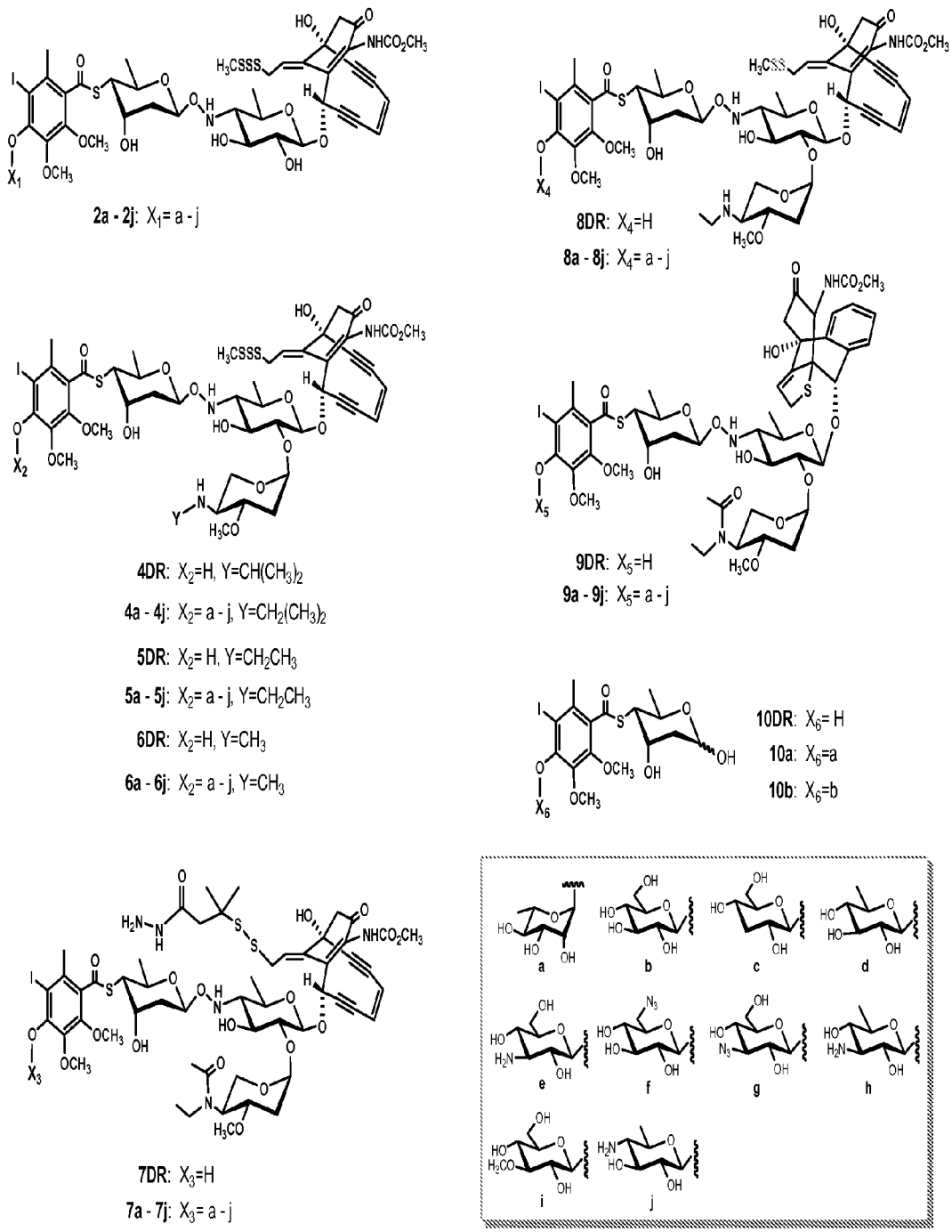
FIG. 11. The library of CLM analogs. The "DR" designation stands for "derhamnosylated" (meaning removal of the 3'-O-methylrhamnose unit).

In an experiment designed to further verify the regiospecificity of CalG1, CLM $\alpha_3^I$ (2, FIG. 1B) and TDP-3-deoxy-glucose were co-incubated with CalG1 under standard conditions. Since the CalG1 glycosylation site in (2) is occupied by 3'-O-methylrhamnose (FIG. 1B, 3), no reaction was expected. However, two new products were observed, subsequently identified by LC-MS as (1) and the corresponding 3-deoxyglucoside (2c) (FIG. 1D, panels iv and v). Analysis of control reactions led to the conclusion that this transformation involved a TDP-dependent reverse glycosyltransfer. Specifically, co-incubation of (2) with TDP yielded (1) only in the presence of CalG1 (FIG. 1D, panels ii and iii; FIG. 9A) and analysis of the same 'reverse' reaction by anion exchange HPLC (FIG. 1C) unveiled the production of TDP-3-O-methyl-β-L-rhamnose (3, FIG. 1B, FIG. 9) in substantial quantity, which was absent in the control assay. Thus, CalG1 efficiently excised the native CLM 3'-O-methylrhamnosyl unit in the presence of TDP (to provide (1) and TDP-sugar (3)) and, in the presence of a slight excess of exogenous TDP-3-deoxyglucose, ultimately catalyzed the formation of (2c). Such CalG1-catalyzed in situ 'sugar exchange' might offer an expeditious method for substituting the CLM 3'-O-methylrhamnose with other natural or unnatural sugars. To test this idea, CLM derivatives (FIG. 2) $\alpha_3^I$ (2), $\beta_1^I$ (4), $\gamma_1^I$ (5), $\delta_1^I$ (6), DMH Nac γ (7), $\gamma_2^I$ (8), Nac ε (9) and "fragment III" (10)[9] were assayed in CalG1- catalyzed reactions with the ten established CalG1 TDP-sugar substrates. In every case, the desired sugar-exchanged product was observed by HPLC (FIGS. 10 and 14) with an average sugar exchange conversion of 60% for the eight CLM aglycons in the presence of purified TDP-α-D-glucose or TDP-β-L-rhamnose. Notably, these simple assays led to the CalG1-catalyzed production of a CLM library exceeding 70 members (2a-2j, 4a-4j, 5a-5j, 6a-6j, 7a-7j, 8a-8j, 9a-9j, 10a and 10b, FIGS. 11 and 12), and thereby highlights the combinatorial power of GT-catalyzed 'sugar exchange'.

Given that GT-catalyzed 'sugar exchange' activity proceeds via established NDP-sugar intermediates, GTs may also be used to harvest an exotic sugar from one natural product scaffold and transfer it to a different aglycon in a single reaction. This permutation of GT catalysis avoids the often complex synthesis of highly functionalized NDP-sugars[10]. The assays contained CalG1, a putative 3'-O-methylrhamnose donor—4, 5, 6, 7, 8 or 10 (FIG. 2)—TDP, and the representative acceptor (1).

Figure 13:
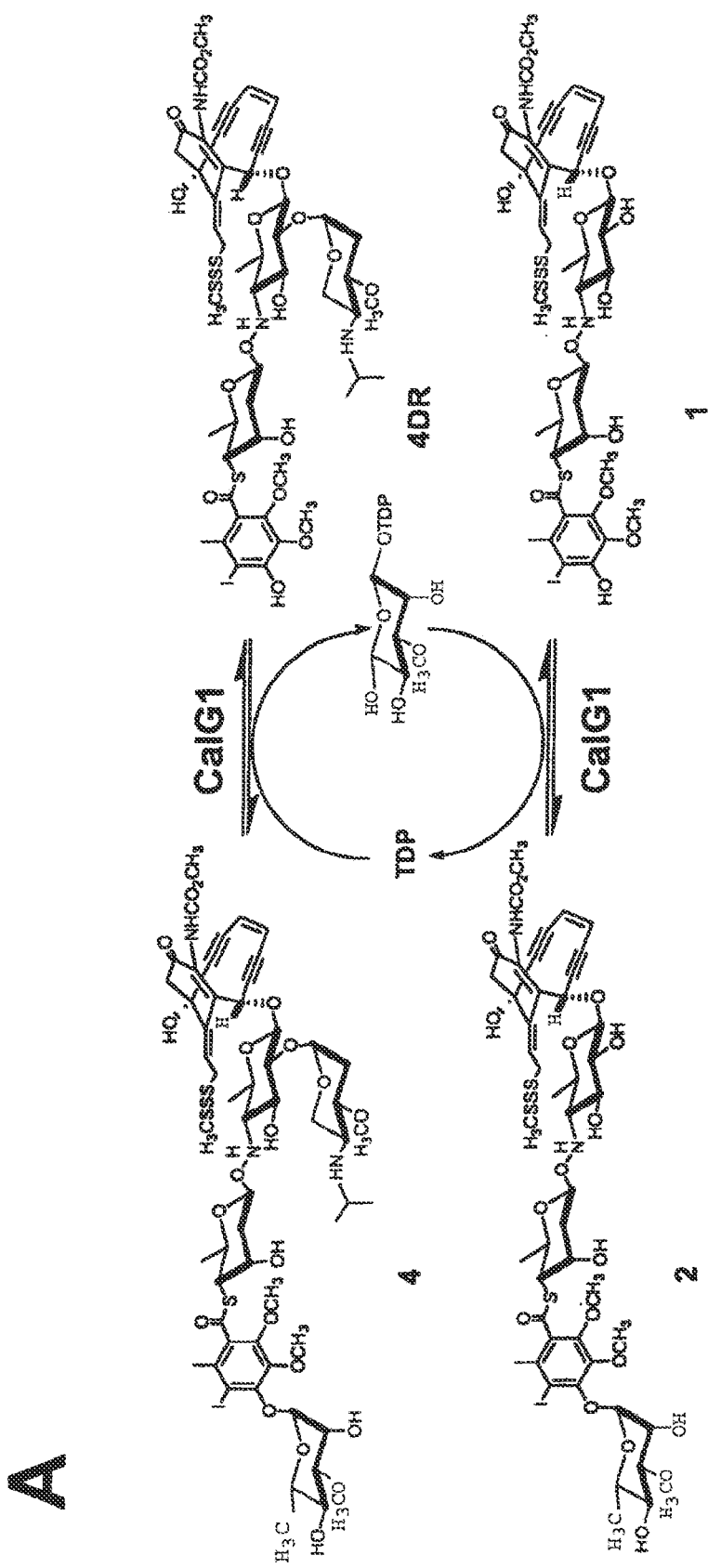
FIG. 13. A representative CalG1-catalyzed aglycon exchange reaction. (A) Scheme for a representative CalG1-catalyzed aglycon exchange. (B) RP-HPLC analysis of CalG1-mediated transformations. (i) Co-incubation of 100 µM 4, 50 µM 1 and 0.1 mM TDP in the presence of 10 µM CalG1 led to the formation of 4DR and 2. (ii) Co-incubation of 100 µM 4 and 0.1 mM TDP in the presence of 10 µM CalG1 led to the production of 4DR. (iii) Co-incubation of 100 µM 2 and 2 mM TDP in the absence of CalG1 resulted in no reaction. (iv) Co-incubation of 100 µM 4 and 2 mM TDP in the absence of CalG1 resulted in no reaction. The "DR" designation stands for "derhamnosylated" (meaning removal of the 3'-O-methylrhamnose unit). Compound distributions are indicated in parentheses. All products in (i)

In each case, the simultaneous excision and in situ transfer of 3'-O-methylrhamnose from four to eight or ten to one was observed, yielding the expected 3'-O-methylrhamnosylated product (2) (FIG. 13). In comparison, controls lacking either CalG1 or TDP gave only starting materials. Thus, in situ 'aglycon exchange' reactions can extend the potential diversity accessible by CalG1.

The reversibility of the CalG1-catalyzed 'sugar exchange' and 'aglycon exchange' transformations described above raised the question as to whether other GT systems would exhibit similar behavior. Thus, three additional GT-catalyzed reactions were examined for reversibility—those of CalG4 (the putative CLM aminopentosyltransferase), GtfD and GtfE (the VCM vancosaminyl- and glucosyltransferase, respectively)[7, 11-13]. Christopher T. Walsh (Harvard Medical School, Boston, Mass., USA) provided GtfD and GtfE expression clones. CalG4 was produced in a similar fashion as CalG1 (FIG. 5)[7]. In the presence of TDP, CalG4 catalyzed the excision of the aminopentose sugar moiety (FIG. 2) from sugar donor CLM derivatives 4, 5, 6, and 8 (FIG. 15). Wyeth Research provided some of these CLM analogs.

CalG4 also catalyzed in situ 'aglycon exchange', transferring the excised aminopentoses from donors 4-6 and 8 to the exogenous aglycon acceptor (1) in the presence of TDP with conversions ranging from 19-69% (FIG. 16). In comparison, controls lacking TDP (even in the presence of alternative NDPs) or CalG4 gave only starting materials. Besides identifying CalG4 as the aminopentosyltransferase involved in CLM biosynthesis, these results confirm that, in contrast to the previously proposed UDP-sugar pathways[14], CLM aminopentose biosynthesis proceeds via a TDP-sugar pathway. Additionally, this demonstrates that the reversibility of GT catalysis is not unique to the CalG1 reaction.

To extend these studies beyond enediyne scaffolds, the VCM GTs GtfD and GtfE were overexpressed and purified as previously described[11]. Similar to the CLM GTs, GtfD catalyzed the excision of L-vancosamine from the parent sugar donor VCM (11) to form pseudoaglycon 13 (FIG. 3A). In a separate aglycon exchange reaction, GtfD catalyzed the transfer of L-vancosamine from (11) to the unnatural acceptor (14)[13] to give (15), a VCM analog containing both a sugar-appended azido handle for chemoselective ligation and a vancosaminyl moiety (27% conversion, FIG. 3A and FIG. 17). Likewise, the glucosyltransferase GtfE could also catalyze sugar excision from both (13) and the unnatural sugar donor (14). Consistent with an equilibrium only moderately favoring the glycoside product in the GtfE-catalyzed reaction, the $K_{eq}$ was determined to be 4.5 (FIG. 18). GtfE could also participate in aglycon exchange, as revealed by the GtfE-catalyzed generation of unnatural NDP-sugar (16) for CalG1-catalyzed glycosyltransfer to the enediyne acceptor (1) in a tandem, one-pot, GtfE/CalG1-catalyzed aglycon exchange reaction (FIG. 3B). With an overall conversion of 48%, this transformation highlights the potential of two-GT systems to mediate aglycon exchange between compounds from different natural product classes (FIG. 19).

The exploitation of GT-catalyzed reaction reversibility may facilitate the use of glycosylation as a tool to modulate the activity of therapeutically important natural products[5]. For example, prior to this work, only two methods for differentially glycosylating CLMs were available—pathway engineering and total synthesis. While the former has proven to be a powerful derivatization tool for certain natural products[15], the stringent genetic limitations of the CLM-producing M. echinospora has rendered this approach impractical[7]. Alternatively, reworking previously reported CLM syntheses to provide efficient divergent routes to the >70 CLM analogs reported herein is also likely impracticable[17-18]. Nicolaou et al. achieved the enantioselective synthesis of CLM $\gamma_1^I$ in twenty nine steps with an overall yield of 0.63%[17] while Danishefsky and coworkers achieved CLM $\gamma_1^I$ in seventeen steps with an overall yield of 0.67%[18]. With respect to rare NDP-sugars, the demonstrated in situ generation of TDP-β-L-vancosamine (12, FIG. 3A) herein is a significant advance over reported synthetic methods that required seven linear steps to achieve an overall yield of less than 7%, originating from the same starting material, VCM[10]. The CLM-derived TDP-3-O-methyl-β-L-rhamnose (3, FIG. 1B) and the three TDP-N-alkylaminopentoses (derived from donors 4-6 and 8, FIG. 2 and FIG. 15) have not been previously synthesized, and therefore, direct comparisons to other synthetic routes are not possible[20-22]. Advanced synthetic intermediates related to these NDP-sugars have been reported. As a point of comparison, the simpler substrate TDP-β-L-rhamnose has been prepared by a five-step chemical synthesis with an overall yield of 27%[20] or a two-step enzymatic method in 62% yield[21]. The most advanced intermediate corresponding to the aminopentoses found in the CLMs required eleven linear steps and provided an overall yield of <12%[22].

Figure 4:
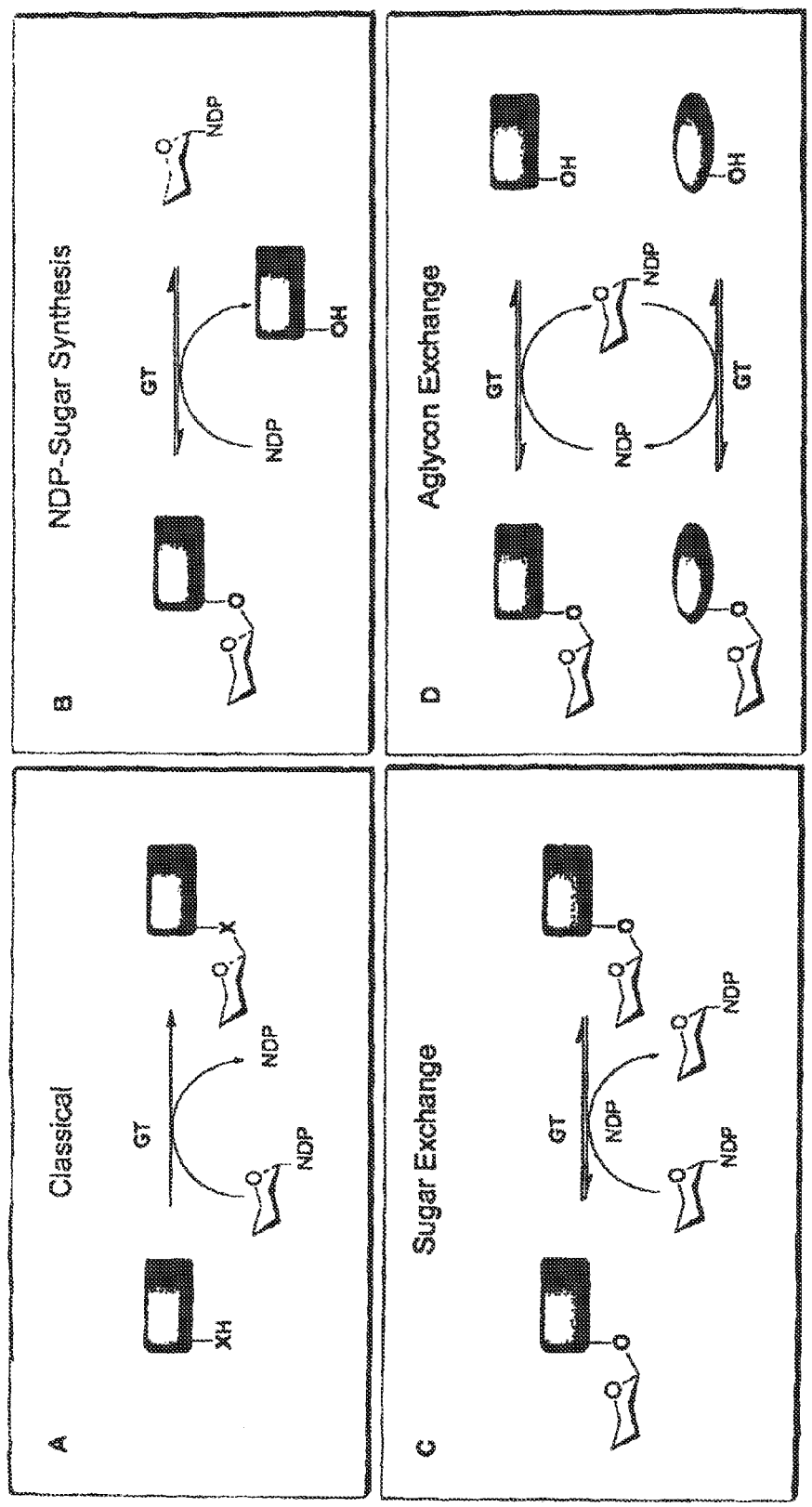
FIG. 4. Schematic of glycosyltransferase catalysis. (A) The 'classical' GT-catalyzed sugar transfer from an NDP-sugar donor to an acceptor to form a glycosidic bond. (B) NDP-sugar synthesis via reverse glycosyltransfer. (C) The GT-catalyzed sugar exchange reaction to exchange native natural product sugar appendages with alternative sugars supplied as exogenous NDP-sugars. (D) A generalized scheme for an aglycon exchange reaction wherein a sugar is excised from one natural product (as an NDP-sugar) and subsequently attached to a distinct aglycon acceptor. In this reaction, the interchange of aglycons from a single natural product class is generally accomplished via one GT while the interchange of aglycons from different compound classes requires multiple GTs.

Although Glaser and Brown described the reversibility of the native chitin synthetase reaction in one of the first reports of in vitro GT activity[23], the perception of GT catalysis has remained one of unidirectionality, transforming NDP-sugar and aglycon substrates into glycoside products (FIG. 4A)[25-29].

Cardini et al. first demonstrated the reversibility of the native sucrose synthetase reaction[25], which has subsequently been exploited to prepare UDP-glucose on large scale[26]. However, this enzyme is unique among Leloir GTs in that it catalyzes the formation of an unusually high energy sucrose glycosidic linkage ($\Delta G^\circ$−29.3 kJ/mol)[27]. The reversibility of a reaction catalyzed by macrolide resistance GT OleD was implicated by the measurement of its equilibrium constant ($K_{eq}$=156)[28]. Reversibility of the reaction catalyzed by macrolide GT VinC using a 3-fold molar excess of VinC was also recently reported[29].

In contrast, this study uncovered reversibility in reactions catalyzed by both previously uncharacterized GTs (CalG1 and CalG4) and well-studied GTs (GtfD and GtfE) (77-73). Consistent with an equilibrium only moderately favoring glycoside formation ($K_{eq}$=4.5 for GtfE), these model GT-catalyzed reactions could be modulated via simple adjustments in relative substrate concentrations. Glycosyltransfer reversibility could be exploited to synthesize valuable rare NDP-sugars (FIG. 4B), exchange one sugar on a core scaffold for another (FIG. 4C), or transfer sugars from one scaffold to another (FIG. 4D), suggesting GT catalysis to be of significantly greater versatility and utility than was previously appreciated.

Materials and Methods

Materials. E. coli DH5α and BL21(DE3) competent cells were purchased from Invitrogen (Carlsbad, Calif.). The pET-16b E. coli expression vector was purchased from Novagen (Madison, Wis.). Primers were purchased from Integrated DNA Technology (Coralville, Iowa). Pfu DNA polymerase was purchased from Stratagene (La Jolla, Calif.). Restriction enzymes and T4 DNA ligase were purchased from New England Biolabs (Ipswich, Mass.). Other chemicals were purchased from Sigma (St. Louis, Mo.). Calicheamicins $\alpha_3^I$, $\beta_1^I$, $\gamma_1^I$, $\gamma_2^I$, DMH Nac γ and Nac ε were provided by Wyeth Research (Pearl River, New York). TDP-α-L-rhamnose and TDP-β-L-rhamnose were gifts from Dr. Svetlana Borisova and Prof. Dr. Hung-wen Liu (University of Texas at Austin, Austin, Tex.). Analytical HPLC was run on a Varian Prostar 210/216 system connected to a Prostar 330 photodiode array detector (Varian, Walnut Creek, Calif.). Mass spectra (MS) were obtained by using electrospray ionization on Agilent 1100 HPLC-MSD SL quadrupole mass spectrometer (Agilent Technologies, Palo Alto, Calif.) connected with a UV/Vis diode array detector.

Chemoenzymatic Synthesis of TDP-sugars. The $E_p$ (glucose-1-phosphate thymidyltransferase) reaction was carried out in Tris-HCl buffer (50 mM, pH8.0) containing 5 mM $MgCl_2$, 1 U inorganic pyrophosphatase, 10 μM of purified $E_p$, 8 mM sugar-1-phosphate and 6 mM TTP, and incubated at 37° C. for 2 h. The formation of TDP-sugars was monitored by RP-HPLC (Phenomenex, Luna C18, 5 μm, 250×4.6 mm, 30 mM $KH_2PO_4$, pH 6.0, 5 mM tetrabutylammonium hydrogensulfate, 2% $CH_3CN$ with a gradient of 0-50% $CH_3CN$ over 30 min, 1 mL/min, $A_{254}$). The TDP-sugars tested in this study are highlighted in FIG. 6 and relevant literature citations are presented in the FIG. 6 legend.

Preparation of CLM 1. A concentrated methanolic solution of calicheamicin $\beta_1^I$ (4, 15.8 mg, 11.4 μmol) was loaded onto a Dowex 50W-X8 ($H^+$ form) column (10×1.5 cm) saturated with MeOH, and the column was then eluted with 1 L of MeOH. Chromatography was monitored by TLC ($CHCl_3$/MeOH 10/1 v/v—under these conditions the $R_f$ value of (4) is 0.2 and (1) is 0.42). The (1)-containing fractions were pooled and evaporated to dryness to give 9.2 mg (8.8 μmol, 77%) final product.

Preparation of 10. Compound 10 was produced by refluxing 10 mg of calicheamicin $\alpha_3^I$ (2) in 10 mL of wet acetone in the presence 0.1 equivalents pyridinium p-toluene-sulfonate. Progress of the reaction was monitored by RP-HPLC (Phenomenex, Luna C18, 5 μm, 250×4.6 mm, $H_2O$ with a 10%-90% $CH_3CN$ gradient over 20 min, 1 mL/min, A280—under these conditions, calicheamicin $\alpha_3^I$ eluted at 15.5 min and 10 eluted at 11.6 min). After 20 h, acetone was evaporated under pressure and 10 was purified from the remaining crude reaction mixture by preparative RP-HPLC (Discovery®BIO C18, 10 μm, 250 mm×21.2 mm, $H_2O$ with a 10%-90% $CH_3CN$ gradient over 20 min, 10 mL/min, A280). Product-containing fractions were pooled and lyophilized to give 0.8 mg (15%) of 10.

Preparation of 13 and 17[8].

Cloning, expression, and purification of GTs. The calG1 and calG4 genes from the calicheamicin producer, Micromonospora echinospora LL6600, were amplified from genomic DNA by using primer pairs: 5'-gccactgaagcttgact-tacccatatgctagatatg-3' (SEQ. ID NO: 1) (forward, NdeI) and 5'-gacggccagatctgagcggtc-3' (SEQ. ID NO:2) (reverse, BglII) for calC1; 5'-caccggagtgagcatatgcgccagc-3' (SEQ. ID NO:3) (forward, NdeI) and 5'-gtggacggcagggaatgatca agatctgggcgcgacc-3' (SEQ. ID NO:4) (reverse, BglII) for calG4, using Pfu DNA polymerase. PCR products were digested with NdeI/BglII and ligated into the pET16b expression vector (NdeI/BamHI—to generate the N-terminal MGHHHHHHHHHH fusion) to give plasmids pCAM2.2 (CalG1) and pCAM10.2 (CalG4), respectively. GtfD and GtfE were expressed according to literature procedures[16, 19].

For CalG1 expression, a single transformant of E. coli BL21 (DE3)/pCAM2.2 was inoculated into 4 mL LB medium supplemented with 100 μg/mL of ampicillin and grown at 37° C. overnight. The precultures were inoculated into 1 L LB medium with 100 μg/mL of ampicillin and grown at 28° C. to an $OD_{600}$ value of 0.5-0.7. Expression was induced with the addition of 0.4 mM of isopropyl-β-D-thiogalactopyranoside (IPTG) followed by an additional growth for 16 h. The cells obtained from 1 L of culture were pelleted, washed twice with buffer A (20 mM $NaH_2PO_4$, pH 7.5, 500 M NaCl, 10 M imidazole) and resuspended in 30 mL of buffer A supplemented with 1 mg/mL of lysozyme. After a 10 min incubation on ice, the proteins were released from the cells by three rounds of French-press (1,200 psi, Thermo IEC), and the insoluble material was removed by centrifugation at 30,000×g for 1 hr at 4° C. The supernatants were loaded onto a HisTrap HT column (1 mL, Amersham Biosciences), and the N-$(His)_{10}$-tagged CalG1 was eluted with a linear gradient of imidazole (10-500 mM) in buffer A via FPLC (Amersham Biosciences). The purified protein was desalted through a PD-10 column (Amersham Biosciences) and stored in buffer containing 10 mM Tris-HCl (pH 8.0), 100 mM NaCl, and 10% glycerol until use. Protein concentration was measured by Bradford assay[24]. N-$(His)_{10}$-tagged CalG4 and N-$(His)_6$-tagged GtfD, GtfE were purified following the same protocol from the appropriate E. coli overexpression strains.

CalG1/CalG4 Assays. CalG1/CalG4 assays were performed in a total volume of 1004 in Tris-HCl buffer (10 mM, pH 7.5) containing 1 mM of $MgCl_2$. CalG1-catalyzed reactions in the forward direction were carried out by incubating 50 μM PsAg (1) and 300 μM TDP-sugar (FIG. 6) at 30° C. for 3-12 h in the presence or absence of 10 μM CalG1. CalG1-CalG4-catalyzed reactions in the reverse direction were performed by co-incubating 50 μM CLMs (2, 4-10) and 0.2 mM or 2 mM TDP (or UDP, ADP, CDP, GDP) in the presence of 10 μM CalG1/CalG4. CalG1-catalyzed 'sugar exchange' reactions were performed by co-incubating 50 μM CLMs (4-10) and 300 μM TDP-sugar (FIG. 6A) in the presence of 10 μM CalG1. CalG1/CalG4-catalyzed 'aglycon exchange' reactions were performed by co-incubating 50 μM CLMs (4-10) and 50 μM PsAg (1) in the presence of 100 μM TDP and 10 μM CalG1/CalG4. Upon completion, reactions were quenched by the addition of 1004 MeOH, and denatured proteins removed by centrifugation. The formation of new CLM products was monitored by RP-HPLC (Phenomenex, Luna C18, 5 μm, 250×4.6 mm, 0.1% TFA in $H_2O$ with a 10%-100% $CH_3CN$ gradient over 20 min, 1 mL/min, $A_{280}$). Percent conversions were calculated by dividing the integrated area of glycosylated product by the sum of the integrated area of the product and that of the remaining substrate and products were confirmed by LC-MS (ESI). The formation of TDP-sugars in CalG1-catalyzed reverse reactions was monitored by anion exchange HPLC (SphereClone SAX, 5 μm, 250×4.60 mm, H$_2$O with 0%-100% 600 mM ammonium formate gradient over 25 min, 1 mL/min, A$_{254}$[30]. The peaks corresponding to TDP-3-O-methyl-β-L-rhamnose (3) in CalG1-catalyzed reverse reactions with (2) were collected evacuated under pressure and lyophilized twice to remove ammonium formate, prior to ESI-MS analysis.

GtfD/GtfE Assays. Generally, GtfD and GtfE assays were performed in a total volume of 100 μL Tricine-NaOH buffer (75 mM, pH 9.0) containing 2.5 mM MgCl$_2$, 2.5 M TCEP and 1 mg/mL BSA, as previously reported[8]. The GtfD-catalyzed reaction in the reverse direction was performed by co-incubating 100 μM vancomycin and 2 mM TDP at 30° C. for 4 h in the presence of 12 μM GtfD. The GtfD-catalyzed 'aglycon exchange' reaction was performed by co-incubating 100 μM vancomycin (11), 0.1 or 1 mM TDP and 100 μM (14) in the presence of 12 μM GtfD. GtfE-catalyzed reactions in the reverse direction were carried out by co-incubating 100 μM (14) and 2 mM TDP (or UDP) with 10 μM GtfE at 30° C. for 6 h. The two-GT-catalyzed aglycon exchange reaction was effected by co-incubating 100 μM (14), 0.1 mM TDP, 10 μM GtfE, 50 μM (1), and 10 μM CalG1 at 30° C. overnight in Tris-HCl (10 mM, pH7.5) containing 1 mM MgCl$_2$. The formation of new vancomycin-analogs was monitored by RP-HPLC using the conditions described previously for the analysis of CalG1/CalG4-catalyzed aglycon exchange reactions.

Measurement of equilibrium constant ($K_{eq}$) for the GtfE reaction. The time taken for the GtfE-catalyzed native reaction to reach equilibrium (6 h at 37° C.) was first established by measurement of the change in the concentration of vancomycin pseudoaglycon (13) over time. The $K_{eq}$ for GtfE was measured by fixing the ratio of (13)/(17) at 56/44 (a parallel experiment was fixed at 53/47) and varying the ratios of [TDP]/[TDP-Glc] from 1 to 10. The total concentration of (13)+(17) and [TDP] +[TDP-glucose] was kept at 80 μM and 1 mM, respectively. The reaction was performed in a total volume of 1004 in Tricine-NaOH buffer (75 mM, pH 9.0) containing 2.5 mM MgCl$_2$, 2.5 mM TCEP, 1 mg/mL BSA and 10 μM GtfE with incubation at 37° C. for 6 h. The change in (13) was monitored by RP-HPLC as described previously and plotted against the ratio of [TDP]/[TDP-glucose]. The equilibrium constant was subsequently determined from the equation $K_{eq}=3)/(17))\times([TDP]/[TDP-glucose])$.

LC-MS/MS analysis of CLM analogs. LC-ESI-QTOF-MS/MS analysis of the CLM analogs was performed using a capillary LC system (Waters Corp., Milford, Mass.) coupled to a QTOF Micro mass spectrometer (Waters Corp.). Chromatographic separations were performed on a reverse phase capillary column (Atlantis® dC18, 3 μm, 75 μm×100 mm). The mobile phases used were: (A) 5% acetonitrile and 0.1% formic acid in H$_2$O; (B) 5% H$_2$O and 0.1% formic acid in acetonitrile; (C) 0.1% formic acid in H$_2$O. Samples were loaded onto a trap column (PepMap™ C18, 300 μm×1 mm, 5 μm) using mobile phase C at a flow rate of 30 μL/min for 3 min to desalt the sample. A gradient of mobile phases A and B was then applied (1% B increase per min starting at 5% B) at a flow rate of 200 nL/min. The nanoflow electrospray ionization (ESI) source conditions were set as follows: capillary voltage 3800V, sample cone voltage 40V, extraction cone voltage 1V, source temperature 120° C., cone gas (N$_2$) 13 L/hr. The MS scan was from m/z 100 to 2000. The MS/MS scan was from m/z 50 to 2000 at a collision energy of 16 eV.

Referring now to FIG. 28, CalG2 and CalG3 have now been shown to also exhibit reversible reactivity and sugar flexibility. The reactions catalyzed by CalG2 and CalG3 are shown in FIG. 28(A), with product characterization by RP-HPLC illustrated in FIG. 28(C). In FIG. 29(B), the inventors demonstrate that CalG2 and CalG3 utilize the various sugar substrates shown therein.

EXAMPLE II

Tandem Sugar-Assembly by AveBI-Catalyzed Aglycon Exchange Reaction: Exploitation of a Macrolide Glycosyltransferase for Avermectin Glycorandomization Avermectins (AVMs, e.g. FIG. 21, 101) are 16-membered macrocyclic lactones produced by *Streptomyces avermectinius*. The avermectins, and the related C$_{22}$-C$_{23}$-reduced ivermectin (e.g. FIG. 21, 107), target the γ-aminobutyric acid (GABA)-related chloride ion channels unique to nematodes, insects, ticks and arachnids, with little or no mammalian toxicity.[34] The widespread commercial use of these remarkable anthelmintic agents began approximately twenty-five years ago as veterinary antiparasitic agents and has more recently expanded to clinical applications for the control of onchocerciasis, stongyloidiasis and lymphatic filariasis. From a biosynthetic perspective, AVMs are one of only a few known natural products postulated to derive from iterative glycosylation.[35] Specifically, a single glycosyltransferase (GT) is required for the attachment of the AVM oleandrosyl-disaccharide (AveBI), proposed to proceed in a stepwise, tandem manner (FIG. 21A).

Evidence in support of iterative glycosylation includes the existence of a single glycosyltransferase gene (aveBI) within the AVM gene locus,[39] in vivo studies suggestive of TDP-oleandrose (FIG. 21A, (104)) as an immediate precursor to the AVM oleandrose moiety,[37] and the production of a variety of glycosylated AVMs via in vivo pathway engineering.[38]

Accordingly, the present invention provides the first definitive in vitro biochemical verification of AveBI-catalyzed tandem glycosylation. Furthermore, consistent with the recent illumination of the reversibility of natural product GT-catalyzed reactions,[39] the AveBI-catalyzed reaction is shown to also be reversible, the utility of which is demonstrated by generating fifty AVM variants.

The aveBI gene was amplified from pWHM473[38] and assessed in several expression systems. However, the functional expression of aveBI was only achieved in *S. lividans* TK64 by the use of expression vectors pPWW49 and pPVVW50.[40] N-His$_6$-tagged AveBI was subsequently purified to greater than 90% purity using HisTrap FPLC purifying system (FIG. 22).

The sequence-confirmed aveBI PCR product was inserted into vector pPWW50 to give expression plasmid pCAM4.10, which was introduced into *Streptomyces lividans* TK64. The cells expressing N-(His)$_6$-AveBI were resuspended in 30 ml of buffer A (20 mM NaH$_2$PO$_4$, pH 7.5, 500 mM NaCl, 10 mM imidazole) supplemented with 1 mg/ml of lysozyme. The proteins were released from the cells by 3 rounds of French-press (1,200 psi). The supernatants were loaded onto the HisTrap HT column (1 ml) and the N-(His)$_6$-tagged AveBI was eluted with a linear gradient of imidazole (10-500 mM) in buffer A by a FPLC system.

After desalting through PD-10 column the purified AveBI was stored in the buffer containing 25 mM Tris-HCl (pH 8.0), 100 mM NaCl and 10% glycerol.

Aglycons 102, 103, 105, 106 and 108 (FIG. 21B) were prepared via selective acid-mediated hydrolysis of AVM B1a (101) and IVM (7).

Ivermectin (107, 460 mg, 0.525 mmol) was added to a solution of 10 ml 2% $H_2SO_4$ in isopropanol and stirred at room temperature under argon for 6 h. The reaction was stopped via addition of 0.1 ml of triethylamine ($NEt_3$). Sample was dried, dissolved in 500 μl methanol and loaded onto a silica column (3×30 cm) pre-equilibrated with petroleum. After elution with EtOAc/petroleum varying from 0/10, 1/9, 2/8, 3/7, 2/6 (ea. 100 ml), 105 (125.9 mg, 0.215 mmol, 41%) and 106 (182.7 mg, 0.250 mmol, 48%) were obtained with an overall yield of 89%. A small fraction of 108 (1 mg) was also recovered. Similarly, 102 (8.9 mg, 0.015 mmol, 17%) and 103 (39.0 mg, 0.053 mmol, 61%) were prepared from AVM B1a (101, 76 mg, 0.087 mmol) with an overall yield of 78%. 5. $^1$H-NMR (400 Hz, $CD_3OD$): δ 3.26 (d, J=1.8 Hz, 1H), 5.46 (d, J=1.8 Hz, 1H), 1.86 (s, 3H), 4.27 (d, J=5.6 Hz, 1H), 3.80 (d, J=5.6 Hz, 1H), 4.63, 4.70 (d, J=14 Hz, 2H), 5.83 (d, J=11.2 Hz, 1H), 5.92 (dd, J=11.2, 14.8 Hz, 1H), 5.72 (dd, 1=14.8, 10 Hz, 1H), 2.63 (m, 1H), 1.18 (d, J=6.8 Hz, 3H), 3.99 (br, 1H), 1.57 (s, 3H), 5.49 (t, J=8.0 Hz, 1H), 2.32 (t, J=8.0 Hz, 2H), 3.74 (m, 1H), 0.85, 1.95 (m, 2H), 5.03 (m, 1H), 2.24 (dd, 1=4.0, 12 Hz, 1H), 1.24 (t, J=12 Hz, 1H), 1.5-1.6 (m, 5H), 0.85 (d, J=5.6 Hz, 3H), 3.29 (m, 1H), 1.55 (m, 1H), 0.91 (d, J=6.8 Hz, 3H), 1.48 (m, 2H), 1.01 (t, 1=7.4 Hz, 3H); $^{13}$C-NMR ($CD_3OD$): δ 173.47, 47.10, 120.30, 137.17, 19.93, 69.01, 82.26, 81.90, 141.49, 68.71, 121.91, 126.24, 138.38, 41.54, 19.94, 78.43, 140.46, 14.96, 118.40, 35.27, 69.14, 37.78, 70.20, 42.98, 98.96, 36.95 (2C), 29.39, 18.01, 78.32, 32.59, 12.45, 28.65, 13.00. 106. $^1$H-NMR (400 Hz, $CD_3OD$): δ 3.25 (d, J=1.8 Hz, 1H), 5.46 (d, J=1.8 Hz, 1H), 1.85 (s, 3H), 4.26 (d, J=5.6 Hz, 1H), 3.80 (d, 1=5.6 Hz, 1H), 4.62, 4.67 (d, J=14 Hz, 2H), 5.85 (d, J=11.2 Hz, 1H), 5.91 (dd, J=11.2, 14.8 Hz, 1H), 5.74 (dd, J=14.8, 10 Hz, 1H), 2.68 (m, 1H), 1.20 (d, J=7.2 Hz, 3H), 4.02 (br, 1H), 1.57 (s, 3H), 5.20 (t, J=7.6 Hz, 1H), 2.33 (t, J=7.6 Hz, 2H), 3.74 (m, 1H), 0.83, 1.94 (m, 2H), 5.05 (m, 1H), 2.23 (dd, J=4.0, 12 Hz, 1H), 1.27 (m, 1H), 1.5-1.6 (m, 5H), 0.83 (d, J=5.0 Hz, 3H), 3.31 (m, 1H), 1.55 (m, 1H), 0.91 (d, J=6.4 Hz, 3H), 1.48 (m, 2H), 0.99 (t, 1=7.4 Hz, 3H), 4.83 (d, J=3.2 Hz, 1H), 1.5 (m, 2H), 3.55 (m, J=9.2 Hz, 1H), 3.07 (t, J=9.4 Hz, 1H), 3.87 (dd, J=6.2, 9.6 Hz, 1H), 1.25 (d, J=6.2 Hz, 3H), 3.48 (s, 3H); $^{13}$C-NMR ($CD_3OD$): δ 173.58, 47.09, 120.29, 136.63, 19.94, 69.05, 82.27, 82.04, 141.94, 68.74, 121.76, 126.67, 138.39, 41.17, 20.98, 83.27, 137.26, 15.39, 120.03, 35.08, 69.03, 37.98, 70.27, 42.95, 99.08, 36.94 (2C), 29.44, 17.97, 77.81, 32.60, 12.76, 28.45, 13.01, 96.55, 35.98, 79.57, 77.64, 70.00, 18.27, 57.67.

The reversibility of the AveBI reaction was examined using commercially-available 101 and TDP.

The chemoenzymatic synthesis of sugar nucleotide (TDP-β-L-olivose) required six linear steps with an overall reported yield of 20%.

RP-HPLC analysis of an in vitro assay containing 50 μM 101, 2 mM TDP and 12 μM AveBI revealed the formation of 103 from 101 (30%, FIG. 21A and FIG. 23), while 101 remained unchanged in control assays lacking either TDP or AveBI.

Generally, AveBI assays were performed in a total volume of 100 l in Tris-HCl buffer (50 mM, pH 8.0) containing 2 mM $MgCl_2$. Reversibility of AveBI reaction was assayed by co-incubation of 100 μM avermectin B1a (1) or ivermectin (7) and 2 mM TDP with 12 μM AveBI at 30° C. overnight.

The AveBI-catalyzed aglycon exchange reaction was assayed by co-incubation of 100 M (1), 100 μM (5) and 2 mM TDP with 12 μM AveBI at 30° C. overnight.

To assess whether AveBI was capable of catalyzing an 'aglycon exchange' reaction,[39] a reaction containing 100 μM (01), 100 μM (105), 2 mM TDP and 12 μM AveBI was subsequently analyzed. Examination of this reaction revealed the production of TDP-oleandrose (104) from (103) (63%) and the subsequent transfer of oleadrose to (105), to provide (106) (28%) and trace amounts of (107) (7%) (FIG. 21A, FIG. 23). Cumulatively, these studies unequivocally establish AveBI as the GT responsible for the stepwise tandem assembly of the AVM oleandrosyl disaccharide and reveal the AveBI-catalyzed reaction to be readily reversible and amenable to 'aglycon exchange' transglycosylation strategies.[39]

The AveBI sugar nucleotide specificity was subsequently probed with twenty-two NDP-sugars (generated chemically or chemoenzymatically, FIG. 24).[41] As a representative example, IVM aglycone (105) with TDP-6-deoxyglucose led to a new product (99% conversion, FIG. 20A), the LC-MS of which was consistent with the anticipated product (105a) (FIG. 21B).

The reaction contained 50 μM algycon (101-103, 105-108), approximate 300 μM TDP-sugar and 12 μM AveBI, and was incubated at 30° C. overnight.

Substituting TDP-6-deoxyglucose with UDP-6-deoxyglucose in the same assay gave (105a) in only 10% yield, indicating a preference for TDP-sugars. Further AveBI-IVM assays revealed that nine additional TDP-sugar substrates were converted to their corresponding IVM glycosides 105b-105j (FIG. 21B). In a similar fashion, the same set sugars were transferred to aglycons 102, 103, 106 and 108, producing glycosides 102a-102j, 103a-103j, 106a-106j and 108a-108j (FIG. 21, FIG. 20), respectively. The conversion rates for a-e glycosides ranged from 18% to 99% while only trace production (1%-10%) of f-j glycosides was observed, except for 106 h (25%) and 106g (19%). All products were confirmed by LC-MS (supporting information, Table 1). Consistent with the previous in vivo studies,[38] no tandem addition of D-configured sugars to aglycon (102) and (105) or trisacchride AVM derivatives was observed in this study.

TABLE 1

LC-MS characterization of AVM analogues.

| Compound No. | Conversion rate (%) | Retention time (min) | calcd | MS (m/z) [M + H]+ | [M + Na]+ | [M – H]− |
|---|---|---|---|---|---|---|
| 102 | / | 16.6 | 584.3 | 585.2 | 587.0 | 584.3 |
| 102a | 94.4% | 12.3 | 730.4 | 731.2 | | 729.4 |
| 102b | 52.9% | 17.1 | 714.4 | | 737.2 | 713.4 |
| 102c | 28.9% | 10.5 | 716.4 | | 739.2 | 715.4 |
| 102d | 13.6% | 7.7 | 729.4 | 730.4 | 768.2 | 728.2 |
| 102e | 22.0% | 7.4 | 729.4 | 730.2 | 768.2 | 729.0 |
| 102f | 2.5% | 13.4 | 771.4 | 772.2 | 794.2 | 770.4 |
| 102g | 7.2% | 14.2 | 728.4 | 729.2 | 751.2 | 727.4 |
| 102h | 6.1% | 10.2 | 730.4 | | 753.4 | 729.4 |
| 102i | 1.0% | 10.2 | 730.4 | | 753.4 | 729.4 |
| 102j | 1.0% | 13.2 | 771.4 | 772.2 | 794.2 | 770.4 |
| 103 | / | 21.2 | 728.4 | 729.0 | 751.0 | 727.4 |
| 103a | 93.1% | 18.5 | 874.5 | 875.3 | 897.2 | 873.4 |
| 103b | 84.7% | 25.1 | 858.5 | 859.2 | 881.2 | 857.5 |
| 103c | 86.5% | 15.9 | 860.5 | 861.2 | 883.2 | 859.5 |
| 103d | 18.8% | 8.7 | 873.5 | 874.2 | | 872.4 |
| 103e | 19.9% | 8.2 | 873.5 | 874.0 | 896.2 | 872.5 |
| 103f | 2.4% | 20.3 | 915.5 | 916.0 | 938.0 | 914.4 |
| 103g | 6.7% | 23.7 | 872.5 | 873.2 | 895.0 | 871.5 |

TABLE 1-continued

LC-MS characterization of AVM analogues.

| Compound No. | Conversion rate (%) | Retention time (min) | MS (m/z) calcd | [M + H]+ | [M + Na]+ | [M − H]− |
|---|---|---|---|---|---|---|
| 103h | 8.0% | 14.6 | 874.5 | | 897.0 | 874.4 |
| 103i | 5.7% | 14.6 | 874.5 | | 897.0 | 873.2 |
| 103j | 2.5% | 18.3 | 915.5 | | 938.0 | 914.4 |
| 105 | / | 22.1 | 586.4 | 587.2 | | 585.4 |
| 105a | 98.5% | 15.3 | 732.4 | 733.2 | 755.0 | 731.4 |
| 105b | 48.7% | 23.8 | 716.4 | 716.8 | 739.0 | 715.4 |
| 105c | 20.3% | 13.2 | 718.4 | 719.2 | | 717.4 |
| 105d | 20.8% | 8.7 | 731.4 | 732.0 | 754.0 | 730.4 |
| 105e | 24.4% | 8.1 | 731.4 | 732.0 | 754.0 | 730.4 |
| 105f | 9.6% | 21.4 | 773.4 | 774.2 | 796.0 | 772.4 |
| 105g | 22.4% | 18.8 | 730.4 | 731.2 | | 729.4 |
| 105h | 5.1% | 12.9 | 732.4 | | 755.0 | 731.4 |
| 105i | 1.6% | 14.2 | 732.4 | | 755.0 | 731.4 |
| 105j | 1.2% | 15.4 | 773.4 | | 796.0 | 772.4 |
| 106 | / | 29.5 | 730.4 | | 753.0 | 729.4 |
| 106a | 98.5% | 26.9 | 876.5 | | 899.0 | 875.4 |
| 106b | 85.2% | 34.4 | 860.5 | | 883.2 | 859.5 |
| 106c | 73.6% | 23.1 | 862.5 | | 885.0 | 861.4 |
| 106d | 18.2% | 8.1 | 875.5 | 876.2 | | 874.2 |
| 106e | 30.3% | 8.0 | 875.5 | 876.2 | 898.2 | 874.5 |
| 106f | 5.1% | 28.8 | 917.5 | | 940.2 | 916.4 |
| 106g | 18.7% | 33.1 | 874.5 | | 897.2 | 873.5 |
| 106h | 24.9% | 20.6 | 876.5 | | 899.2 | 875.4 |
| 106i | 9.2% | 20.7 | 876.5 | | 899.0 | 875.2 |
| 106j | 5.4% | 25 | 917.5 | | 940.0 | 916.4 |
| 108 | / | 26.1 | 716.4 | | 739.2 | 715.4 |
| 108a | 95.3% | 23.5 | 862.5 | | 885.2 | 861.4 |
| 108b | 90.5% | 31.6 | 846.5 | | 869.2 | 845.2 |
| 108c | 80.8% | 20.2 | 848.5 | | 871.2 | 847.4 |
| 108d | 27.4% | 9.5 | 861.5 | 862.2 | 884.2 | 860.4 |
| 108e | 17.8% | 8.8 | 861.5 | 862.2 | 884.2 | 860.4 |
| 108f | 5.1% | 25.6 | 903.5 | | 926.2 | 902.4 |
| 108g | 7.0% | 28.4 | 860.5 | 861.2 | 883.2 | 859.5 |
| 108h | 4.4% | 18.0 | 862.5 | | 885.2 | 861.5 |
| 108i | 11.6% | 18.1 | 862.5 | | 885.4 | 861.4 |
| 108j | 6.2% | 22.2 | 901.5 | 902.2 | 924.4 | 900.4 |

Materials and Methods

Materials. *E. coli* DH5a and BL21 (DE3) competent cells were purchased from Invitrogen. The *E. coli* expression vectors pET-11a, pET28a were purchased from Novagen. The plasmids, pPWW49 and pPWW50, for expression in *S. lividans*, were generous gifts from Dr. Udo F. Wehmeier and Prof. Dr. Wolfgang Piepersberg (Bergische University, Wuppertal, Germany). Primers were ordered from Integrated DNA Technology. Pfu DNA polymerase was purchased from Stratagene. Restriction enzymes and T4 DNA ligase were purchased from New England Biolabs. Other chemicals were purchased from Sigma (St. Louis, Mo.). TDP-α-L-rhamnose and TDP-β-L-rhamnose were gifts from Dr. Svetlana Borisova and Prof. Dr. Hung-wen Liu (University of Texas at Austin, Austin, USA). Ivermectin was purchased from Sigma (St. Louis, Mo.) and avermectin B1a was purchased from Supelco (Bellefonte, Pa.). $^1$H NMR, $^{13}$C NMR and two-dimensional correlation spectra (gCOSY, TOCXY, gHSQC and gHMBC) were recorded in $CD_3OD$ on a 400-MHz Varian INOVA model NMR spectrometer. Chemical shifts are reported in parts per million (ppm, δ) relative to $CD_3OD$ (0.00). $^1$H NMR splitting patterns with observed first-order coupling are designated as singlet (s), doublet (d), or triplet (t). Splitting patterns that could not be interpreted or easily visualized are designated as multiplet (m). Mass spectra (MS) were obtained by using electrospray ionization on Agilent 1100 HPLC-MSD SL quadrupole mass spectrometer connected with a UV/Vis diode array detector.

Chemoenzymatic Synthesis of TDP-sugars. The $E_p$ (glucose-1-phosphate thymidylyltransferase) reaction was carried out in Tris-HCl buffer (50 mM, pH8.0) containing 5 mM $MgCl_2$, 1U inorganic pyrophosphatase, 10 μM of purified $E_p$, 8 mM sugar-1-phosphate and 6 mM TTP, and incubated at 37° C. for 2 h. The formation of TDP-sugars was monitored by RP-HPLC (Phenomenex, Luna C18, 5 μm, 250×4.6 mm, 30 mM $KH_2PO_4$, pH 6.0, 5 mM tetrabutylammonium hydrogensulfate, 2% $CH_3CN$ with a gradient of 0-50% $CH_3CN$ over 30 min, 1 mL/min, $A_{254}$).

Chemical Preparation of Algycons. Ivermectin (107, 460 mg, 0.525 mmol) was added to a solution of 10 ml 2% $H_2SO_4$ in isopropanol and stirred at room temperature under argon for 6 h. The reaction was stopped via addition of 0.1 ml of triethylamine (NEt$_3$).[43] Sample was dried, dissolved in 500 μl methanol and loaded onto a silica column (3×30 cm) pre-equilibrated with petroleum. After elution with EtOAc/petroleum varying from 0/10, 1/9, 2/8, 3/7, 2/6 (ea. 100 ml), 105 (125.9 mg, 0.215 mmol, 41%) and 106 (182.7 mg, 0.250 mmol, 48%) were obtained with an overall yield of 89%. A small fraction of (108) (1 mg) was also recovered. Similarly, (102, 8.9 mg, 0.015 mmol, 17%) and (103, 39.0 mg, 0.053 mmol, 61%) were prepared from AVM B1a (101, 76 mg, 0.087 mmol) with an overall yield of 78%.

NMR data for (105) and (106). 105. $^1$H-NMR (400 Hz, $CD_3OD$): δ 3.26 (d, J=1.8 Hz, 1H), 5.46 (d, J=1.8 Hz, 1H), 1.86 (s, 3H), 4.27 (d, J=5.6 Hz, 1H), 3.80 (d, 1=5.6 Hz, 1H), 4.63, 4.70 (d, J=14 Hz, 2H), 5.83 (d, j=11.2 Hz, 1H), 5.92 (dd, J=11.2, 14.8 Hz, 1H), 5.72 (dd, 1==14.8, 10 Hz, 1H), 2.63 (m, 1H), 1.18 (d, J=6.8 Hz, 3H), 3.99 (br, 1H), 1.57 (s, 3H), 5.49 (t, J=8.0 Hz, 1H), 2.32 (t, J=8.0 Hz, 2H), 3.74 (m, 1H), 0.85, 1.95 (m, 2H), 5.03 (m, 1H), 2.24 (dd, 1=4.0, 12 Hz, 1H), 1.24 (t, J=12 Hz, 1H), 1.5-1.6 (m, 5H), 0.85 (d, J=5.6 Hz, 3H), 3.29 (m, 1H), 1.55 (m, 1H), 0.91 (d, J=6.8 Hz, 3H), 1.48 (m, 2H), 1.01 (t, 1=7.4 Hz, 3H); $^{13}$C-NMR ($CD_3OD$): δ 173.47, 47.10, 120.30, 137.17, 19.93, 69.01, 82.26, 81.90, 141.49, 68.71, 121.91, 126.24, 138.38, 41.54, 19.94, 78.43, 140.46, 14.96, 118.40, 35.27, 69.14, 37.78, 70.20, 42.98, 98.96, 36.95 (2C), 29.39, 18.01, 78.32, 32.59, 12.45, 28.65, 13.00.

(106). $^1$H-NMR (400 Hz, $CD_3OD$): δ 3.25 (d, J=10.8 Hz, 1H), 5.46 (d, J=1.8 Hz, 1H), 1.85 (s, 3H), 4.26 (d, J=5.6 Hz, 1H), 3.80 (d, J=5.6 Hz, 1H), 4.62, 4.67 (d, J=14 Hz, 2H), 5.85 (d, J=11.2 Hz, 1H), 5.91 (dd, J=11.2, 14.8 Hz, 1H), 5.74 (dd, 1=14.8, 10 Hz, 1H), 2.68 (m, 1H), 1.20 (d, J=7.2 Hz, 3H), 4.02 (br, 1H), 1.57 (s, 3H), 5.20 (t, 1=7.6 Hz, 1H), 2.33 (t, 1=7.6 Hz, 2H), 3.74 (m, 1H), 0.83, 1.94 (m, 2H), 5.05 (m, 1H), 2.23 (dd, J=4.0, 12 Hz, 1H), 1.27 (m, 1H), 1.5-1.6 (m, 5H), 0.83 (d, J=5.0 Hz, 3H), 3.31 (m, 1H), 1.55 (m, 1H), 0.91 (d, J=6.4 Hz, 3H), 1.48 (m, 2H), 0.99 (t, J=7.4 Hz, 3H), 4.83 (d, 1=3.2 Hz, 1H), 1.5 (m, 2H), 3.55 (m, 1=9.2 Hz, 1H), 3.07 (t, 1=9.4 Hz, 1H), 3.87 (dd, 1=6.2, 9.6 Hz, 1H), 1.25 (d, J=6.2 Hz, 3H), 3.48 (s, 3H); $^{13}$C-NMR ($CD_3OD$): δ 173.58, 47.09, 120.29, 136.63, 19.94, 69.05, 82.27, 82.04, 141.94, 68.74, 121.76, 126.67, 138.39, 41.17, 20.98, 83.27, 137.26, 15.39, 120.03, 35.08, 69.03, 37.98, 70.27, 42.95, 99.08, 36.94 (2C), 29.44, 17.97, 77.81, 32.60, 12.76, 28.45, 13.01, 96.55, 35.98, 79.57, 77.64, 70.00, 18.27, 57.67.

Cloning, expression and purification of AveBI. The aveBI gene was amplified from pWHM473 using primers 5'-ctagacagtgacatatgtcagatcattttctcttc-3' (SEQ. ID NO:5) (forward, NdeI) and 5'-aaccctgtgagatctactcaccgcccggc-3' (SEQ. ID NO:6) (reverse, BglII). The PCR products were cut with NdeI/BglII and inserted into pPCPU21 (NdeI/BglII), resulted in plasmid pCAM4.9. After confirmation by sequencing, the aveBI insert was cut with NdeI/BglII from pCAM4.9 and ligated to vectors pET11a, pET16b, pPWW49 and pPWW50 (NdeI/BamHI),[44] resulted in expression plasmids pCAM4.1, pCAM4.2, pCAM4.11 and pCAM4.10, respectively. Soluble expression of AveBI was only achieved in *Streptomyces lividans* TK64 harboring pCAM4.11 or pCAM4.10. Specifically, the plasmid pCAM4.10 was introduced into *S. lividans* TK64 by standard transformation,[45] for the expression of N-(His)$_6$-AveBI. The transformants were grown in liquid TSB media (thiostrepton 25 µg/ml) for three days at 28° C. and were transferred to YEME media (thiostrepton 25 µg/ml) containing 25% sucrose. The culture was incubated at 28° C. for two more days and cells were harvested. The pellets obtained from 300 mL of culture were washed twice with buffer A (20 mM NaH$_2$PO$_4$, pH 7.5, 500 mM NaCl, 10 mM imidazole) and resuspended in 30 ml of buffer A supplemented with 1 mg/ml of lysozyme. After a 10 min incubation on ice, the proteins were released from the cells by three rounds of French-press (1,200 psi, Thermo IEC) and the insoluble material was removed by centrifugation at 30,000 g for 1 hr (4° C.). The supernatants were loaded onto the HisTrap HT column (1 ml, Amersham Biosciences) and the N-(His)$_6$-tagged AveBI was eluted with a linear gradient of imidazole (10-500 mM) in buffer A by a FPLC system (Amersham Biosciences). The purified protein was desalted through PD-10 column (Amersham Biosciences) and stored in the buffer containing 25 mM Tris-HCl (pH 8.0), 100 mM NaCl and 10% glycerol until use. Protein concentration was measured by Bradford assay.[46]

AveBI assays. Generally, AveBI assays were performed in a total volume of 100 µl in Tris-HCl buffer (50 mM, pH 8.0) containing 2 mM MgCl$_2$. Reversibility of AveBI reaction was assayed by co-incubation of avermectin B1a (101, 100 µM) and TDP (2 mM) with 12 µM AveBI at 30° C. overnight. The AveBI-catalyzed aglycon exchange reaction was assayed by co-incubation of 100 µM (101), 100 µM (105) and 2 mM TDP with 12 µM AveBI at 30° C. overnight. To probe AveBI sugar substrate specificity, the reaction contained 50 µM algycon (101-103, 105-108) and approximate 300 µM TDP-sugar (directly from E$_p$ reactions) in the presence of 12 µM AveBI and was incubated at 30° C. overnight. The reactions were analyzed by HPLC using a reversed phase column Luna C18, 5 µm, 250×4.6 mm (Phenomenex) with UV detection at 243 nm. The following elution profile was used: solvent system (solvent A, 0.1% TFA in water; solvent B, acetonitrile), 30% B to 70% B (linear gradient, 0-5 min), 70% B to 100% B (linear gradient, 5-25 min); 100% B (25-30 min); 100% B to 30% B (linear gradient, 30-31 min) and 30% B (31-40 min).

In summary, the present invention provides indisputable evidence of the AveBI-catalyzed tandem sugar addition within AVM biosynthesis. Further, the demonstrated promiscuity of AveBI further highlights the inherent flexibility of many secondary metabolite GTs and provides a rapid one-pot strategy for the generation of 50 differentially-glycosylated AVMs. In contrast to the macrolide in vitro GT studies to date,[42] AveBI does not require a helper protein for activity. Finally, the recently established 'sugar/aglycon exchange' strategies,[39] and the concept of reversibility of GT-catalyzed reactions to provide exotic sugar nucleotides, are shown to apply to macrolides.

EXAMPLE III

Exploiting the Reversibility of Glycosyltransferase-catalyzed Reactions for Combinatorial Diversification of Macrolides Reversibility of EryBV-Catalyzed Reactions (FIG. 25)

As shown in FIG. 25, TDP mediated the reverse catalysis of EryBV to excise mycarose from 3-a-mycarosyl erythronolide B (206) to form erythronolide B (208). EryBV also catalyzed the transformation of erythromycin B (202) and erythromycin D (204) into (205), but had no reverse activity on erythromycin A (201) and erythromycin C (203). In an EryBV-catalyzed 'aglycon exchange' reaction, TDP-mycarose (207) was produced in a reverse catalysis from 206 and was subsequently transferred to 6-deoxyerythronolide B (209) to yield a new macrolide (210). The corresponding RP-HPLC analysis of this exchange reaction was depicted in FIG. 26.

Combinatorial 'Aglycon Exchange' Reactions

Figure 27A:
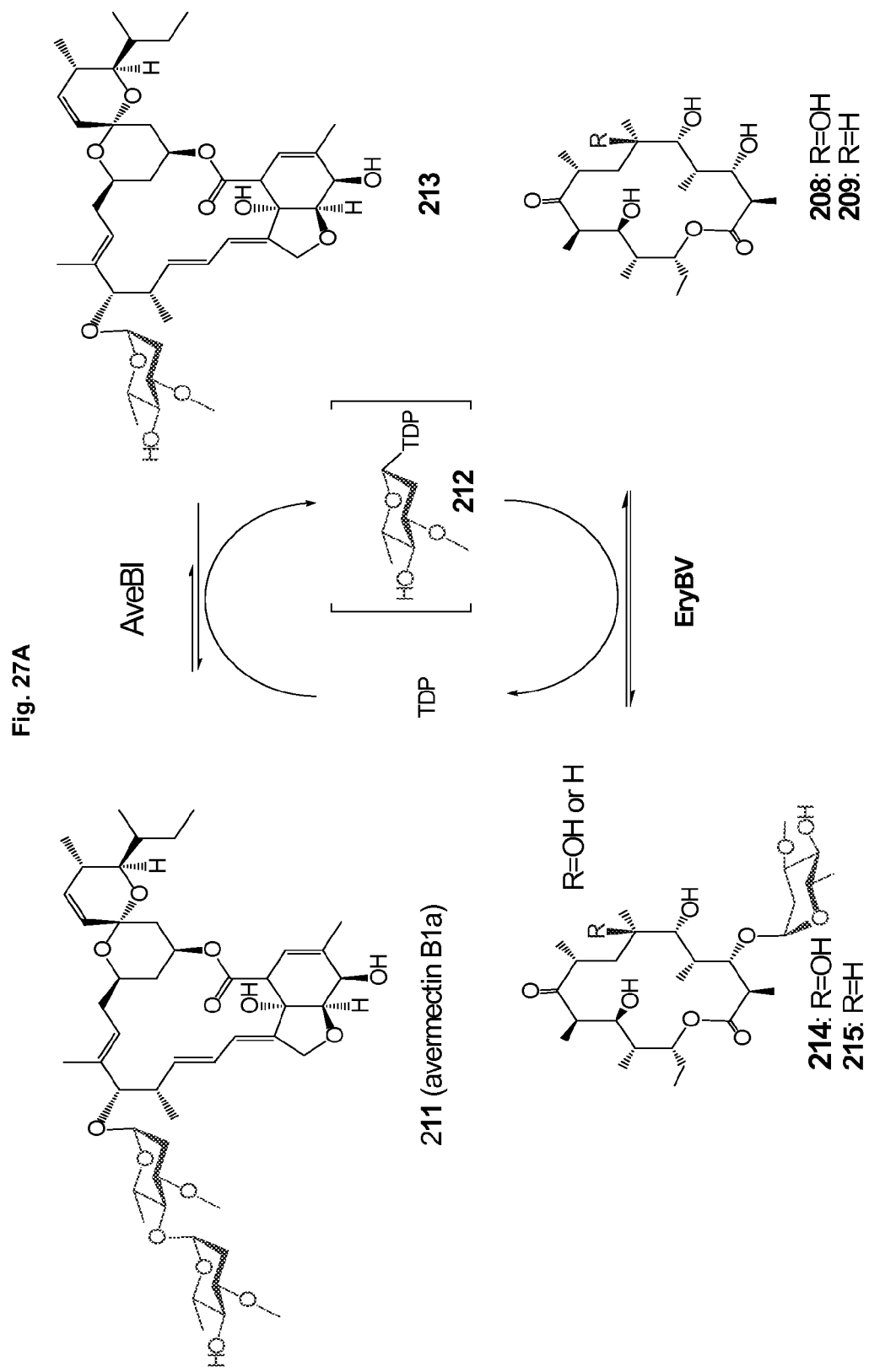
Figure 27B:
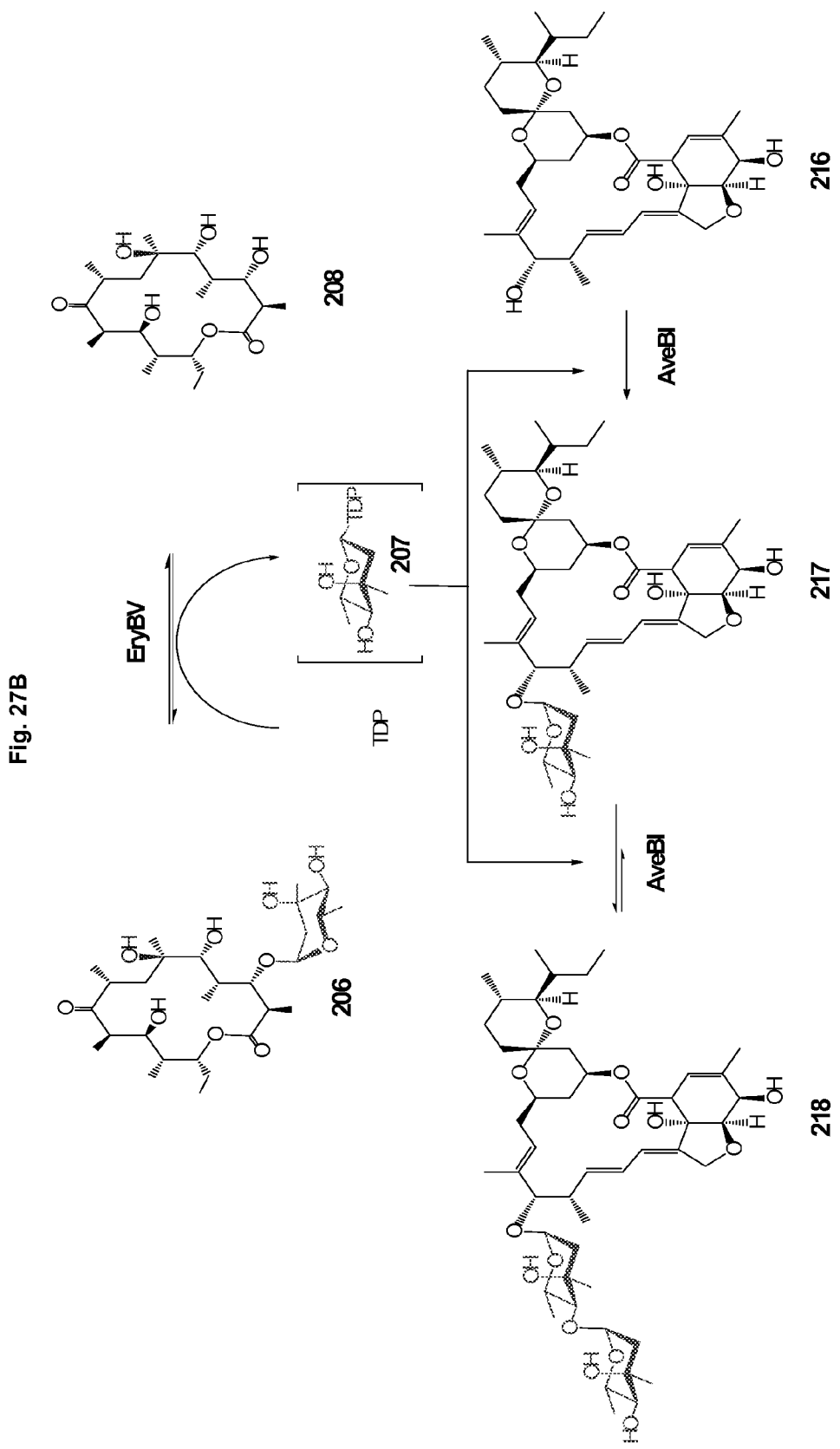

As shown in FIG. 27, 27A. TDP mediated the AveBI reverse catalysis to produce TDP-oleandrose (212) from (211), (212) was subsequently transferred by EryBV to (208) (or 209) to yield new macrolides (214) or (215). Further, as shown FIG. 27B, TDP mediated the EryBV reverse catalysis to produce TDP-mycarose (207) from (206), (207) was subsequently transferred by AveBI to (216) in a stepwise, tandem reaction to produce new avermectin derivatives (217) and (218).

EXAMPLE IV

Exploitation of Glycosyltransferase for Polyene Glycorandomization

FIG. 29 illustrates five polyene antibiotics which are acted upon by reversible glycosyltransferase NysD1. NysD1, the glycosyltransferase which glycosylates Nystatin A1, has been shown to exhibit flexibility in aglycon and sugar donor specificities. NysD1 has been shown capable of acting upon five different polyene aglycons and eight different NDP-sugars.

The present invention exploits the reversibility of glycosyltransferases to generate new, unnatural biomolecules. The broad utility of this invention is seen in FIGS. 30A-E, where five different scaffolds are shown, upon which various glycosyltransferases can act, and upon which reversible GTs act, each GT being capable of utilizing multiple aglycons and sugar donors.

Those skilled in the art will recognize, or be able to ascertain using no more then routine experimentation, numerous equivalents to the specific compounds, protocols, methods, assays and reagents described herein. Such equivalents are considered to be within the scope of this invention and covered by the following claims. All publications, patents, and patent applications cited herein are hereby incorporated by reference in their entirety for all purposes.

REFERENCES

1. C. Breton et al., Glycobiology 16, 29R (2006).
2. P. Sears et al., Science 291, 2344 (2001).
3. P. L. Deangelis, et al., j. Biol. Chem. 278, 35199 (2003).
4. M. Wacker et al., Science 298, 1790 (2002).
5. B. R. Griffith et al., Curr. Opin. Biotechnol. 16, 622 (2005).
6. K. M. Koeller et al., Chem. Rev. 100, 4465 (2000).

7. j. Ahlert et al., Science 297, 1173 (2002).
8. R. Nagarajan et al., J. Chem. Soc., Chem. Comm. 1306 (1988).
9. S. Walker et al., Proc. Natl. Acad. Sci. U.S.A. 89, 4608 (1992).
10. M. Oberthür et al., Org. Lett. 6, 2873 (2004).
11. H. C. Losey, et al., Biochemistry 15, 4745 (2001).
12. C. T. Walsh et al., Biochem. Soc. Trans., 31, 487 (2003).
13. X. Fu et al., Nat. Biotechnol. 21, 1467 (2003).
14. T. Bililign et al., ChemBioChem 3, 1143 (2002).
15. S. Blanchard et al., Curr. Opin. Chem. Biol. 10, 263 (2006).
16. H. C. Losey et al., Chem. Biol. 9, 1305 (2002).
17. K. C. Nicolaou et al., J. Am. Chem. Soc. 115, 7625 (1993).
18. S. A. Hitchcock et al., J. Am. Chem. Soc. 117, 5750 (1995).
19. X. Fu et al., Nat. Biotechnol. 21, 1467 (2003).
20. Y. Zhao et al., J. Org. Chem. 63, 7568 (1998).
21. K. Marumo et al., Eur. J. Biochem. 204, 539 (1992).
22. S. H. Kim et al., J. Am. Chem. Soc. 116, 1766 (1994).
23. L. Glaser et al., J. Biol. Chem. 228, 729 (1957).
24. M. M. Bradford, Anal. Biochem. 72, 248 (1976). 25. C. E. Cardini et al., J. Biol. Chem. 214, 149 (1955).
26. C. Rupprath et al., Curr. Med. Chem., 12, 1637 (2005).
27. E. F. Neufeld et al., Adv. Carb. Chem. 18, 309 (1963).
28. L. M. Quiros et al., J. Biol. Chem. 275, 11713 (2000).
29. A. Minami et al., Tetrahedron Lett. 46, 6187 (2005).
30. S. Pattathil et al., Planta 221, 538 (2005).
31. J. Jiang et al., J. Am. Chem. Soc. 122, 6803 (2000).
32. J. Jiang et al., Angew. Chem. Int. Ed. Engl. 40, 1502 (2001).
33. W. A. Barton, et al., Proc. Natl. Acad. Sci. U.S.A. 99, 13397 (2002).
34. (a) Geary, T. G. Trends Parasitol. 2005, 21, 530-532. (b) Omura, S. et al., Nat. Rev. Microbiol. 2004, 2, 984-989. (c) Dourmishev, A. L. et al., Int. J. Dermatol. 2005, 44, 981-988. (d) Ikeda, H. et al., Chem. Rev. 1997, 97, 2591-2610. (e) Yoon, Y. J. et al., Appl. Microbiol. Biotechnol. 2004, 63, 626-634.
35. Luzhetskyy A. et al., Chem. Biol. 2005, 12, 725-729.
36. Ikeda, H. et al., Proc. Natl. Acad. Sci. U.S.A. 1999, 96, 9509-9514.
37. Schulman, M. D. et al., J. Biol. Chem. 1990, 265, 16965-16970.
38. Wohlert, S. et al., Chem. Biol. 2001, 8, 681-700.
39. Zhang, C.; et al., J.S. Science 2006, manuscript in press.
40. Doumith, M. et al., Mol. Gen. Genet. 2000, 264, 477-485.
41. (a) Barton, W. A. et al., Proc. Natl. Acad. Sci. U.S.A. 2002, 99, 13397-13402. (b) Jiang, J. et al., Angew. Chem. Int. Ed. Engl. 2001, 40, 1502-1505. (c) Barton, W. A. et al., Nat. Struct. Biol. 2001, 8, 545-551. (d) Jiang J. et al., J. Am. Chem. Soc. 2000, 122, 6803-6804. (e) Albermann, C.; S et al. Org. Lett. 2003, 5, 933-936. (f) Fu, X. et al., Nat. Biotechnol. 2003, 21, 1467-1469. (g) Borisova, S. A. et al., Angew. Chem. Int. Ed. 2006, 45, 2748-2753.
42. (a) Borisova, S. A. et al., J. Am. Chem. Soc. 2004, 126, 6534-6535. (b) Yuan, Y.; et al., J. Am. Chem. Soc. 2005, 127, 14128-14129.
43. Wei, G. H. et al., Tetrahedron. Lett. 2004, 45, 6895-6898.
44. Doumith, M. et al., Mol. Gen. Genet. 2000, 264, 477-485.
45. Kieser, T. et al., Practical *Streptomyces* Genetics. The John Innes Foundation: Norwich, England, 2000.
46. Bradford, M. M. Anal. Biochem. 1976, 72, 248-254.
47. Amann, S. et al., Carbohydr. Res. 2001, 335, 23-32.

What is claimed is:

1. A method of generating a biomolecule A, in situ, having a sugar moiety X from a biomolecule B having the sugar moiety X, the method comprising the steps of:
 (a) incubating the biomolecule A, the biomolecule B, and a nucleotide diphosphate in the presence of a glycosyltransferase wherein
  (i) the sugar moiety X of the biomolecule B is excised from the biomolecule B, thereby generating an independent sugar moiety X and a biomolecule aglycon B, whereby a nucleotide diphosphate (NDP)-sugar intermediate is formed; and
  (ii) the independent sugar moiety X and the biomolecule A are ligated, thereby generating the biomolecule A having sugar moiety X; and
 (b) isolating the biomolecule A having sugar moiety X from step (a),
 wherein the glycotransferase is selected from the group consisting of *Micromonospora echinospora* calicheamicin glycosyltransferase 1 (CalG1), *Micromonospora echinospora* calicheamicin glycosyltransferase 2 (CalG2), *Micromonospora echinospora* calicheamicin glycosyltransferas 3 (CalG3), Micromonospora echinospora calicheamicin glycosyltransferase 4 (CalG4), *Amycolaotopsis orientalis* glycosyltransferase D (GtfD), *Amycolatopsis orientalis* glycosyltransferase E (GtfE), *Saccharopolyspora erythraea* erythromycin glycosyltransferase BV (EryBv), and *Streptmyces avermitilis* ayermectin glycosyltransferase (AveBI), and
 wherein the biomolecule is an enediyne, a vancomycin, a bleomycin, an anthracycline, a macrolide, a pluramycin an aureolic acid, an indolocarbazole, an aminglycoside, a glycopeptide, a polyene, a coumarin, a henzoisochro- mancquinone, a calicheamicin, an erythromycin, an avermectin, an ivermectin, an angucycline, a cardiac glycoside a steroid or a flavinoid.

2. The method of claim 1, wherein the hiomolecule A or biomolecule B is an enediyne, a yancomyein, a calieheamiein, an erythromycin, an avermectin, an ivermectin or combinations thereof.

3. The method of claim 1, wherein the method of generating biomolecule A having the sugar moiety X from the biomolecule B having the sugar moiety X is reversible, whereby incubating the biomolecule A having the sugar moiety X and the biomolecule aglycon B in the presence of a glycosyltransferase results in the biomolecule B having the sugar moiety X.

4. A method of generating a biomolecule A having a sugar moiety X and a biomolecule B having a sugar moiety Y from a hiomolecule B having the sugar moiety X and a biomolecule A having the sugar moiety Y comprising the steps of:
 (a) incubating the biomolecule A having the sugar moiety Y, biomolecule B having the sugar moiety X, and a nucleotide diphosphate in the presence of a glycosyltransferase wherein
  (i) the sugar inoiety X of the biomolecule B is excised from the biomolecule B, thereby generating a sugar moiety X-nucleotide diphosphate and a biomolecule aglycon B;
  (ii) the sugar moiety Y of the biomolecule A is excised from the biomolecule A, thereby generating sugar moiety Y-nucieotide diphosphate and a biomolecule aglycon A; and
  (iii) the sugar moiety X-nueleotide diphosphate and the biomolecule A are ligated and the sugar moiety Y-nueleotide diphosphate and the biomolecule B are ligated, thereby generating the biomolecule A having the sugar moiety X and biomolecule B having the sugar moiety Y; and (b) isolating the biomoleeule A having the sugar moiety X and the biomolecule B having from the sugar moiety Y from step (a)(iii), wherein the glygotransferase is selected from the group consisting of *Micromonospora echlnospora* calicheamicin glycosyltransferase 1 (CalG1), *Micromonospora echinospora* calicheamicin glycosyltransferase 2 (CalG2), *Micromonospora echinspora* calicheamicin glycosyltransferase 3 (CalG3), *Micromonospora echinospora* calicheamicin glycosyltransferase 4 (CalG4), *Amycolatopsis orientalis* glycosyltransferase D (GtfD), *Amycolatopsis orientalis* glycosyltransferase E (GtfE), *Saccharopolvspora erythraea* erythromycin glycosyltransferase BV (EryBV), and *Streptomyces avermitilis* avermectin glycosyltransferase (AveBI), and wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin a benzoisochromanequinone, a calicheamicin, an erythromycin, an avermectin, an ivermectin, an angueycline, a cardiac glycoside, a steroid or a flavinoid.

5. The method of claim 4, wherein the biomolecule A or biomolecule B is an enediyne, a vancomycin, a calicheamicin, an erythromycin, an avermectin, an ivermectin or combinations thereof.

6. The method of claim 4, wherein the method of generating the biomolecule A having the sugar moiety X and the biomolecule B having the sugar moiety Y is reversible, and whereby incubating the biomolecule A having the sugar moiety X and the biomolecule B having the sugar moiety Y in the presence of a glycosyltransferase results in the biomolecule B having the sugar moiety X and the biomolecule A having the sugar moiety Y.

7. A method of generating a library of isolated glycosylated biomolecules comprising a biomolecule A having sugar moiety X, wherein the method comprises transferring the sugar moiety X from a biomolecule B having sugar moiety X (a natural glycoside biomolecule or a natural biomolecule having sugar moiety X) to the biomolecule A, the method comprising the steps of:

(a) incubating the biomolecule A, the biomolecule B and a nucleotide diphosphate in the presence of a glycosyltransferase wherein (i) the sugar moiety X of the biomolecule B is excised from the biomolecule B, thereby generating an independent sugar moiety X and a biomolecule aglycon B, whereby a nucleotide diphosphate (NDP)-sugar intermediate is formed; and (ii) the independent sugar moiety X and the biomolecule A are ligated, thereby generating the biomolecule A having the sugar moiety X; and (b) isolating the biomolecule A having sugar moiety X from step (a), wherein glycosyltransferase selected from the group consisting of *Micromonospora echinospora* calicheamicin glycosyltransferase 1 (CalG1), *Micromonospora echinospora* calicheamicin glycosyltransferase 2 (CalG2), *Micromonospora echinospora* calicheamicin glycosyltransferase 3 (CalG3), *Micromonospora echinospora* calicheamicin glycosyltransferase 4 (CalG4), Amvcolatopsis orientalis glycosyltransferase D (GtfD), Amvcolatopsis orientalis glycosyltransferase E (GtfE), Saccharopolwpora erythraea erythromycin glycosyltransferase BV (EryBV), and Streptomvces avermitilis avermectin glycosyltransferase (AveBI) and wherein the biomolecule is an enediyne, a vancomycin, a bleomycin, an anthracycline, a macrolide, a pluramycin, an aureolic acid, an indolocarbazole, an aminglycoside, a glycopeptide, a polyene, a coumarin, a benzoisochromanequinone, a calicheamicin, an erythromycin, an avermectin, an ivermectin, an anguecycline, a cardiac glycoside, a steroid or a flavonoid.

8. The method of claim 7, wherein the first and the second glycosylated biomolecule backbones are independently selected from: an enediyne, a vancomycin, a calicheamicin, an avermectin, an ivermectin, an erythromycin or combinations thereof.

9. The method of claim 7, wherein the sugar moiety is selected from:

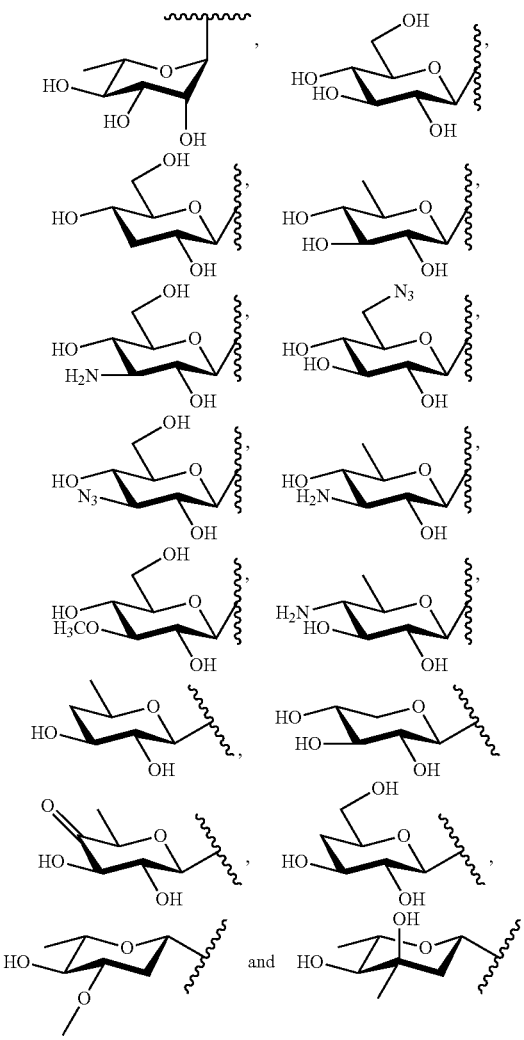

* * * * *